(12) United States Patent
Takeda et al.

(10) Patent No.: US 9,395,625 B2
(45) Date of Patent: Jul. 19, 2016

(54) ACRYLIC ACID ESTER DERIVATIVE AND METHOD FOR PRODUCING SAME, INTERMEDIATE AND METHOD FOR PRODUCING SAME, HIGH-MOLECULAR-WEIGHT COMPOUND, AND PHOTORESIST COMPOSITION

(71) Applicant: KURARAY CO., LTD., Kurashiki-shi (JP)

(72) Inventors: Akinobu Takeda, Tainai (JP); Takashi Fukumoto, Tainai (JP); Osamu Nakayama, Tainai (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 14/381,352

(22) PCT Filed: Feb. 25, 2013

(86) PCT No.: PCT/JP2013/054829
§ 371 (c)(1),
(2) Date: Aug. 27, 2014

(87) PCT Pub. No.: WO2013/129342
PCT Pub. Date: Sep. 6, 2013

(65) Prior Publication Data
US 2015/0037733 A1    Feb. 5, 2015

(30) Foreign Application Priority Data

Feb. 27, 2012 (JP) ................................ 2012-039630
Oct. 23, 2012 (JP) ................................ 2012-234163

(51) Int. Cl.

| | |
|---|---|
| C07D 275/04 | (2006.01) |
| C07D 275/06 | (2006.01) |
| G03F 7/038 | (2006.01) |
| C08F 20/38 | (2006.01) |
| G03F 7/039 | (2006.01) |
| C08F 228/02 | (2006.01) |
| C08F 128/06 | (2006.01) |

(52) U.S. Cl.
CPC .............. *G03F 7/038* (2013.01); *C07D 275/04* (2013.01); *C07D 275/06* (2013.01); *C08F 20/38* (2013.01); *C08F 128/06* (2013.01); *C08F 228/02* (2013.01); *G03F 7/0397* (2013.01)

(58) Field of Classification Search
None
See application file for complete search history.

(56) References Cited

U.S. PATENT DOCUMENTS

| 4,828,603 | A | * | 5/1989 | Patel | ....................... | A01N 43/90 504/196 |
|---|---|---|---|---|---|---|
| 2010/0136478 | A1 | | 6/2010 | Kawaue et al. | | |
| 2011/0117497 | A1 | | 5/2011 | Sato et al. | | |
| 2012/0009519 | A1 | | 1/2012 | Kim et al. | | |

FOREIGN PATENT DOCUMENTS

| JP | 2002-234882 | * | 8/2002 |
|---|---|---|---|
| JP | 2007-093910 | * | 4/2007 |
| JP | 2008/081768 | * | 7/2008 |
| JP | 2010-210796 | * | 9/2010 |
| JP | 2011-051945 | | 3/2011 |
| JP | 2011-085878 | | 4/2011 |
| JP | 2011-252145 | | 12/2011 |
| JP | 2012-017264 | | 1/2012 |
| WO | 2010/001913 | | 1/2010 |
| WO | 2012/033019 | | 3/2012 |
| WO | 2012/043102 | | 4/2012 |
| WO | 2012/098952 | | 7/2012 |

OTHER PUBLICATIONS

International Search Report issued Apr. 9, 2013 in PCT/JP13/054829, filed Feb. 25, 2013.
Iwama, T. et al., "Reactions of a β-sultam Ring with Lewis Acids via the C—S Bond Cleavage", Tetrahedron, vol. 54, No. 31, pp. 8941-8974, 1998.
Extended European Search Report issued Jul. 3, 2015 in Patent Application No. 13754838.4.

* cited by examiner

*Primary Examiner* — Laura L. Stockton
(74) *Attorney, Agent, or Firm* — Oblon, McClelland, Maier & Neustadt, L.L.P

(57) ABSTRACT

Provided is an acrylic acid ester derivative which, when used as a constituent unit of a polymer which is included in a photoresist composition for a semiconductor, exhibits excellent lithography characteristics such as LWR and the like. Specifically, provided is an acrylic acid ester derivative represented by the following general formula (1). Furthermore, provided are an intermediate of the acrylic acid ester derivative and a process for producing the same; a polymer containing the acrylic acid ester derivative as a constituent unit; and a photoresist composition for a semiconductor containing the polymer.

(1)

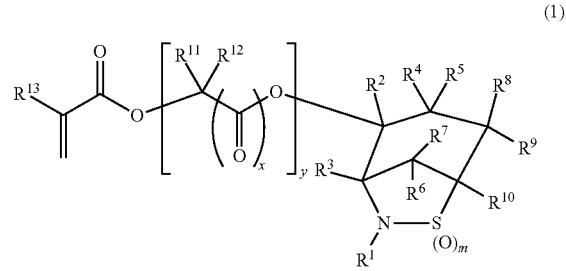

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, m, x, and y are as defined in the text of Description.

4 Claims, No Drawings

ACRYLIC ACID ESTER DERIVATIVE AND METHOD FOR PRODUCING SAME, INTERMEDIATE AND METHOD FOR PRODUCING SAME, HIGH-MOLECULAR-WEIGHT COMPOUND, AND PHOTORESIST COMPOSITION

TECHNICAL FIELD

The present invention relates to an acrylic acid ester derivative which becomes a constituent unit of a polymer included in a photoresist composition for a semiconductor, and a process for producing the same. Further, the present invention relates to an intermediate of the acrylic acid ester derivative and a process for producing the same. Furthermore, the present invention relates to a polymer obtained by polymerizing the acrylic acid ester derivative as at least one of raw materials, and a photoresist composition for a semiconductor containing the polymer as a component.

BACKGROUND ART

In a lithography process using short wavelength such as an ArF excimer laser and extreme ultraviolet rays (EUV), problems are cited in relation to performance of a photoresist for a semiconductor including improvement of such properties as resolution, sensitivity, a pattern shape, and the like. In order to solve these problems, there has been reported improvement of various properties by a photoresist composition for a semiconductor containing a polymer having a (meth)acrylic acid ester derivative as a constituent unit wherein, the (meth)acrylic acid ester derivative has a sulfur-containing ring introduced into an alicyclic structure (see Patent Literature 1). Furthermore, it is also reported that, as a photo-acid generator used in a photoresist for a semiconductor, a compound having a moiety in which a sulfur-containing ring is introduced into an alicyclic structure exhibits good performance (see Patent Literature 1).

CITATION LIST

Patent Literature

Patent Literature 1: Japanese Patent Laid-Open Publication No. 2011-85878

SUMMARY OF INVENTION

Technical Problem

In the days ahead, in an expectation of further progress, expansion of application areas, and the like of lithography technique, development of novel materials which can be used in the field of lithography is desired. With progress in pattern miniaturization, there has been a strong desire for photoresist materials for a semiconductor which may improve, more than ever, various lithography characteristics such as resolution, line width roughness (LWR), and the like; and a pattern shape.

Accordingly, objects of the present invention are to provide a novel acrylic acid ester derivative which, when incorporated into a polymer as one of the constituents thereof, wherein the polymer is included in a photoresist composition for a semiconductor, exhibits excellent lithography characteristics such as LWR and the like and high resolution; and an economically and/or industrially superior process for producing the acrylic acid ester derivative.

Further, objects of the present invention are to provide an intermediate of the acrylic acid ester derivative and an economically and/or industrially superior process for producing the intermediate.

Furthermore, objects of the present invention are to provide a polymer, which contains the acrylic acid ester derivative as a constituent unit and a photoresist composition for a semiconductor containing the polymer.

Solution to Problem

According to the present invention, the objects can be accomplished by providing:

[1] An acrylic acid ester derivative represented by the following general formula (1) (hereinafter, referred to as the acrylic acid ester derivative (1)):

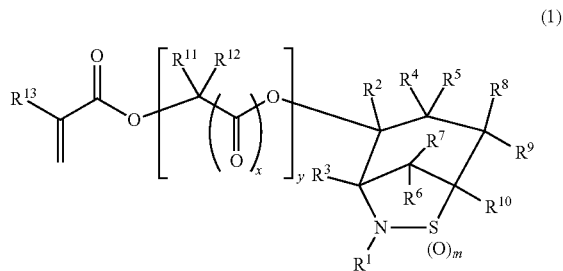

(1)

(wherein, $R^1$ represents a hydrogen atom, an alkyl group having 1 to 10 carbon atoms or a cycloalkyl group having 3 to 10 carbon atoms; $R^2$, $R^3$, $R^5$, $R^6$, $R^8$, $R^9$, and $R^{10}$ each independently represent a hydrogen atom, an alkyl group having 1 to 6 carbon atoms, a cycloalkyl group having 3 to 6 carbon atoms, or an alkoxy group having 1 to 4 carbon atoms; $R^4$ and $R^7$ each independently represent a hydrogen atom, an alkyl group having 1 to 6 carbon atoms, a cycloalkyl group having 3 to 6 carbon atoms, or an alkoxy group having 1 to 4 carbon atoms, or the two bind together to represent an alkylene group having 1 to 3 carbon atoms, —O—, or —S—; $R^{11}$ and $R^{12}$ each independently represent a hydrogen atom, an alkyl group having 1 to 6 carbon atoms, or a cycloalkyl group having 3 to 6 carbon atoms; $R^{13}$ represents a hydrogen atom, a methyl group, or a trifluoromethyl group; m represents 0, 1, or 2; x represents 0 or 1; and y represents 0 or 1);

[2] An acrylic acid ester derivative represented by the following general formula (1-a) (hereinafter, referred to as the acrylic acid ester derivative (1-a)):

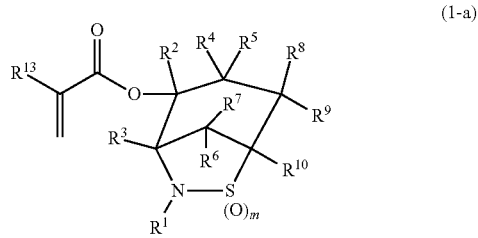

(1-a)

(wherein, $R^1$, $R^2$, $R^3$, $R^4$, $R^5$, $R^6$, $R^7$, $R^8$, $R^9$, $R^{10}$, and m are as defined previously; and $R^{13}$ represents a hydrogen atom, a methyl group, or a trifluoromethyl group);

[3] A process for producing the acrylic acid ester derivative (1-a), wherein an alcohol derivative represented by the following general formula (2) (hereinafter, referred to as the alcohol derivative (2)) and an acrylic acid esterifying agent are reacted:

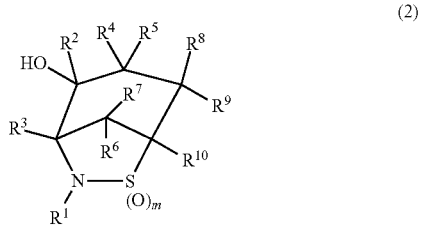
(2)

(In the formula, $R^1$, $R^2$, $R^3$, $R^4$, $R^5$, $R^6$, $R^7$, $R^8$, $R^9$, $R^{10}$, and m are as defined previously);

[4] An acrylic acid ester derivative represented by the following general formula (1-b) (hereinafter, referred to as the acrylic acid ester derivative (1-b)):

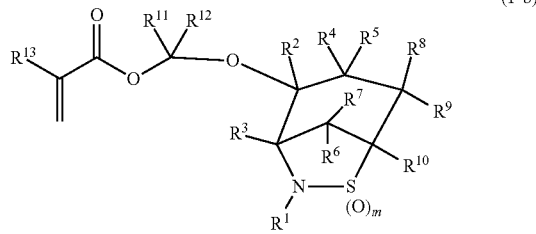
(1-b)

(wherein $R^1$, $R^2$, $R^3$, $R^4$, $R^5$, $R^6$, $R^7$, $R^8$, $R^9$, $R^{10}$, $R^{13}$, and m are as defined previously, and $R^{11}$ and $R^{12}$ represent each independently hydrogen atom, an alkyl group having 1 to 6 carbon atoms or a cycloalkyl having 3 to 6 carbon atoms);

[5] A process for producing the acrylic acid ester derivative (1-b), wherein the alcohol derivative (2), a carbonyl compound represented by the following general formula (3):

(3)

(wherein, $R^{11}$ and $R^{12}$ are as defined previously), and hydrogen halide is reacted to obtain an ether derivative represented by the following general formula (4) (hereinafter referred to as the ether derivative (4)):

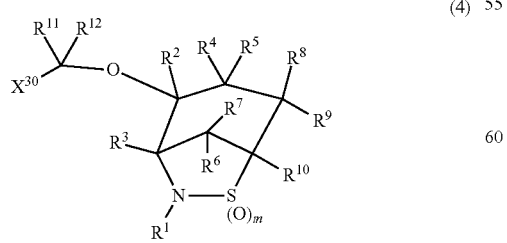
(4)

(wherein, $R^1$, $R^2$, $R^3$, $R^4$, $R^5$, $R^6$, $R^7$, $R^8$, $R^9$, $R^{10}$, $R^{11}$, and $R^{12}$, and m are as defined previously; and $X^{30}$ represents a chlorine atom, a bromine atom, or an iodine atom), and subsequently the ether derivative (4) (hereinafter, referred to as the ether derivative (4)) obtained and an acrylic acid represented by the general formula (5) (hereinafter, referred to as the acrylic acid (5)) are reacted:

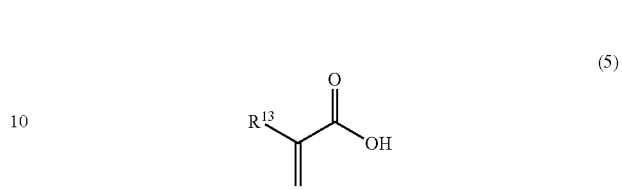
(5)

(wherein, $R^{13}$ is as defined previously);

[6] An acrylic acid ester derivative represented by the following general formula (1-c) (hereinafter, referred to as the acrylic acid ester (1-c)):

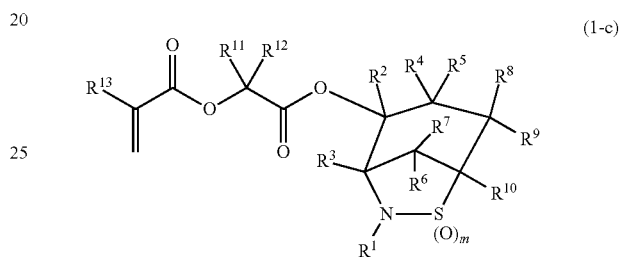
(1-c)

(wherein $R^1$, $R^2$, $R^3$, $R^4$, $R^5$, $R^6$, $R^7$, $R^8$, $R^9$, $R^{10}$, $R^{13}$, and m are as defined previously);

[7] A process for producing the acrylic acid ester derivative (1-c), wherein the alcohol derivative (2) and a haloesterifying agent represented by the following general formula (6) (hereinafter, referred to as the haloesterifying agent (6)):

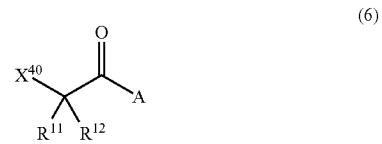
(6)

(wherein, A represents —OH, a chlorine atom, a bromine atom, an iodine atom, —O—C(=O)—C($X^{40}$)($R^{11}$)($R^{12}$) (wherein, $R^{11}$, $R^{12}$, and m are as defined previously; and $X^{40}$ represents a chlorine atom, a bromine atom, or an iodine atom), —O—(C=O)—$^t$Bu, —O—C(=O)-2,4,6-trichlorophenyl, —O—SO$_2$—CH$_3$, or a —O—SO$_2$-p-tolyl group)) are reacted to obtain a haloester derivative represented by the following general formula (7) (hereinafter referred to as the haloester derivative (7)):

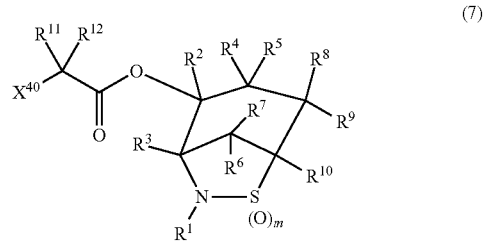
(7)

(wherein, $R^1$, $R^2$, $R^3$, $R^4$, $R^5$, $R^6$, $R^7$, $R^8$, $R^9$, $R^{10}$, $R^{11}$, and $R^{12}$, $X^{40}$, and m are as defined previously), and subsequently the haloester derivative (7) obtained and the acrylic acid (5) are reacted;

[8] An alcohol derivative (2);

[9] A process for producing the alcohol derivative (2), wherein an epoxy derivative represented by the following general formula (8) (hereinafter, referred to as the epoxy derivative (8)):

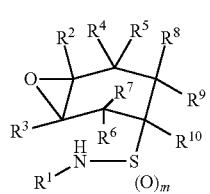

(wherein, $R^1$, $R^2$, $R^3$, $R^4$, $R^5$, $R^6$, $R^7$, $R^8$, $R^9$, $R^{10}$, and m are as defined previously) is cyclized in the presence of an acid or a base;

[10] An ether derivative (4);

[11] A process for producing the ether derivative (4), wherein the alcohol derivative (2), the carbonyl compound (3), and hydrogen halide are reacted;

[12] A haloester derivative (7);

[13] A process for producing the haloester derivative (7), wherein the alcohol derivative (2) and the haloesterifying agent (6) are reacted;

[14] A polymer obtained by polymerizing any of the acrylic acid ester derivative (1), the acrylic acid ester derivative (1-a), the acrylic acid ester derivative (1-b), or the acrylic acid ester derivative (1-c) as at least one of raw materials; and

[15] A photoresist composition comprising the polymer according to [14] and a photo-acid generator.

Advantageous Effect of Invention

A photoresist composition for a semiconductor using a polymer containing the acrylic acid ester derivative (1) of the present invention as a constituent unit can form a high-resolution photoresist pattern having improved LWR than before. The reason why this effect of the present invention is obtained is not clear, but it is presumed that, because the acrylic acid ester derivative (1) possesses a cyclic sulfonamide group as a polar group in the molecule, the polymer containing this constituent unit acquires adequate alkali solubility and, at the time of alkali development, resulting in uniform dissolution in a developing solution.

DESCRIPTION OF EMBODIMENTS

When the acrylic acid ester derivative (1) of the present invention is incorporated as a constituent unit of a polymer which is included in a photoresist composition for a semiconductor, a photoresist pattern can be obtained having excellent lithography characteristics such as LWR and the like, and high resolution. Hereinafter, the acrylic acid ester derivative (1) and an intermediate thereof, and processes for producing them will be described in detail.

In the present description, the definition referring to "favorable" can be chosen optionally, and a combination of the definitions referring to "favorable" is said to be more preferable.

[Acrylic Acid Ester Derivative (1)]

The acrylic acid ester derivative (1) of the present invention is represented by the following general formula (1):

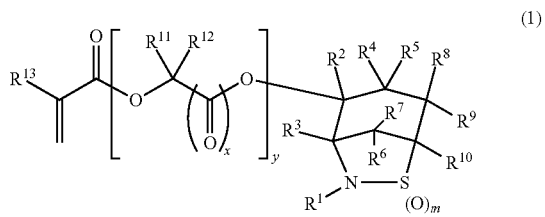

(wherein, $R^1$ represents a hydrogen atom, an alkyl group having 1 to 10 carbon atoms, or a cycloalkyl group having 3 to 10 carbon atoms; $R^2$, $R^3$, $R^5$, $R^6$, $R^8$, $R^9$, and $R^{10}$ each independently represent a hydrogen atom, an alkyl group having 1 to 6 carbon atoms, a cycloalkyl group having 3 to 6 carbon atoms, or an alkoxy group having 1 to 4 carbon atoms; $R^4$ and $R^7$ each independently represent a hydrogen atom, an alkyl group having 1 to 6 carbon atoms, a cycloalkyl group having 3 to 6 carbon atoms, or an alkoxy group having 1 to 4 carbon atoms, or the two bind together to represent an alkylene group having 1 to 3 carbon atoms, —O—, or —S—; $R^{11}$ and $R^{12}$ each independently represent a hydrogen atom, an alkyl group having 1 to 6 carbon atoms, or a cycloalkyl group having 3 to 6 carbon atoms; $R^{13}$ represents a hydrogen atom, a methyl group, or a trifluoromethyl group; m represents 0, 1, or 2; x represents 0 or 1; and y represents 0 or 1).

The alkyl group having 1 to 10 carbon atoms represented by $R^1$ may be either linear or branched and includes, for example, a methyl group, an ethyl group, a n-propyl group, an isopropyl group, a n-butyl group, an isobutyl group, a s-butyl group, a t-butyl group, a linear or branched pentyl group (hereinafter, "linear or branched" will be collectively denoted as "various." Hereafter, the same applies), various hexyl groups, various heptyl groups, various octyl groups, various decyl groups, and the like. Furthermore, the cycloalkyl group having 3 to 10 carbon atoms represented by $R^1$ includes, for example, a cyclopropyl group, a cyclobutyl group, a cyclopentyl group, a cyclohexyl group, a cyclooctyl group, and the like.

The alkyl group having 1 to 6 carbon atoms represented by $R^2$, $R^3$, $R^4$, $R^5$, $R^6$, $R^7$, $R^8$, $R^9$, $R^{10}$, $R^{11}$, and $R^{12}$ may be either linear or branched and includes, for example, a methyl group, an ethyl group, a n-propyl group, an isopropyl group, various butyl groups, various pentyl groups, various hexyl groups, and the like. Further, the cycloalkyl group having 3 to 6 carbon atoms represented by $R^2$, $R^3$, $R^4$, $R^5$, $R^6$, $R^7$, $R^8$, $R^9$, $R^{10}$, $R^{11}$, and $R^{12}$ includes, for example, a cyclopropyl group, a cyclobutyl group, a cyclopentyl group, a cyclohexyl group, and the like.

The alkoxy group having 1 to 4 carbon atoms represented by $R^2$, $R^3$, $R^4$, $R^5$, $R^6$, $R^7$, $R^8$, $R^9$, and $R^{10}$ includes, for example, a methoxy group, an ethoxy group, a n-propoxy group, an isopropoxy group, a n-butoxy group, an isobutoxy group, a t-butoxy group, and the like.

The alkylene group having 1 to 3 carbon atoms represented by bonding of $R^4$ and $R^7$ includes, for example, a methylene group, an ethane-1,1-diyl group, an ethane-1,2-diyl group, a propane-1,1-diyl group, a propane-1,2-diyl group, a propane-1,3-diyl group, and the like.

$R^{13}$ represents a hydrogen atom, a methyl group, and a trifluoromethyl group, among which a hydrogen atom and a methyl group are preferable.

The symbol m represents 0, 1, or 2, among which 2 is preferable. Further, x represents 0 or 1; wherein, when x is 0, it means that the bond is a single bond. Furthermore, y represents 0 or 1; wherein, when y is 0, it means that the bond is a single bond.

In addition, $X^{30}$ in the ether derivative (4) described below and $X^{40}$ in the haloester derivative (7) described below represent a chlorine atom, a bromine atom, or an iodine atom.

[Process for Producing Acrylic Acid Ester Derivative (1)]

The process for producing the acrylic acid ester derivative (1) of the present invention is not particularly limited. However, the acrylic acid ester derivative (1-a), the acrylic acid ester derivative (1-b), and the acrylic acid ester derivative (1-c) can be produced, for example, by the following processes:

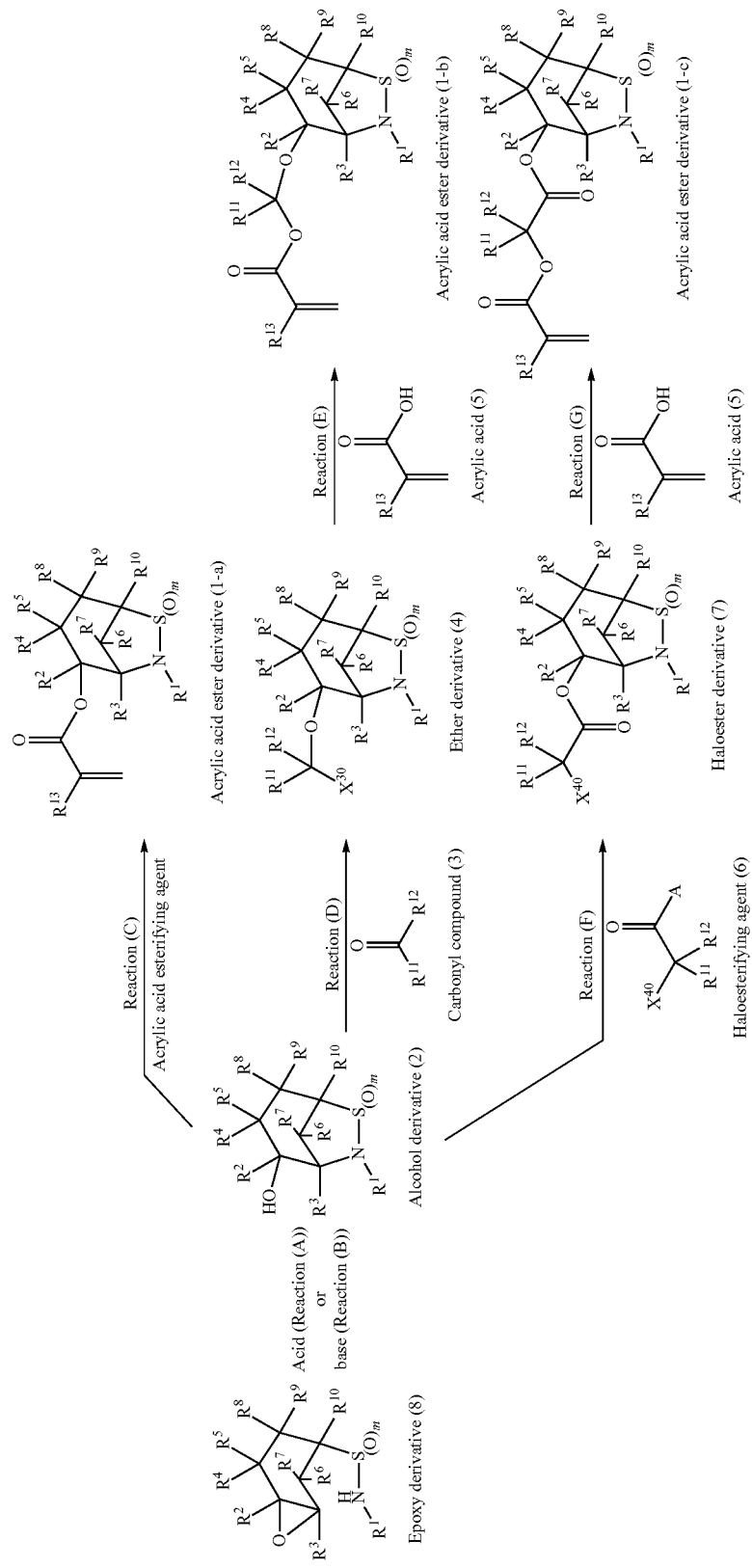

(wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, $X^{30}$, and $X^{40}$, and m are as defined previously. In the haloesterifying agent (6), A represents —OH, a chlorine atom, a bromine atom, an iodine atom, —O—(C=O)—C($X^{40}$)($R^{11}$)($R^{12}$) (wherein, $R^{11}$, $R^{12}$, and $X^{40}$ are as defined previously), —O—(C=O)—$^t$Bu, —O—C(=O)-2,4,6-trichlorophenyl, —O—$SO_2$—$CH_3$, or a —O—$SO_2$-p-tolyl group).

Hereinafter, a process of cyclizing the epoxy derivative (8) in the presence of an acid to obtain the alcohol derivative (2) is referred to as Reaction (A), and a process of cyclizing the epoxy derivative (8) in the presence of a base to obtain the alcohol derivative (2) is referred to as Reaction (B).

A process of reacting the alcohol derivative (2) with an acrylic acid esterifying agent to obtain the acrylic acid ester derivative (1-a) is referred to as Reaction (C).

A process of reacting the alcohol derivative (2) with the carbonyl compound (3) to obtain the ether derivative (4) is referred to as Reaction (D), and a subsequent process of reacting the ether derivative (4) with the acrylic acid (5) to obtain the acrylic acid derivative (1-b) is referred to as Reaction (E).

A process of reacting the alcohol derivative (2) with the haloesterifying agent (6) to obtain a haloester derivative (7) is referred to as Reaction (F), and a subsequent process of reacting the haloester derivative (7) with the acrylic acid (5) to obtain the acrylic acid ester derivative (1-c) is referred to as Reaction (G).

A method of obtaining the epoxy derivative (8) is not particularly limited, and, for example, it can be produced by reacting a norbornene sulfonyl fluoride derivative, obtained by a cycloaddition reaction of ethylene sulfonyl fluoride and the like with cyclopentadiene and the like, with ammonia and the like, followed by epoxidation with a percarboxylic acid (see, for example, U.S. Pat. No. 3,136,787).

(Reaction (A))

Hereinafter, Reaction (A) will be described.

The acid, which can be used in Reaction (A), includes, for example, mineral acids such as hydrochloric acid, sulfuric acid, and the like; organic acids such as methanesulfonic acid, p-toluenesulfonic acid, trifluoromethanesulfonic acid, and the like; Lewis acids such as boron trifluoride, aluminum trichloride, dibutyltin dilaurate, and the like. Among these, the mineral acids or the organic acids are preferable, and sulfuric acid or p-toluenesulfonic acid is more preferable. The acid may be used singly or in a combination of two or more kinds. The amount of the acid used is not particularly limited, but, from the viewpoint of reaction rate, economic efficiency, and ease of after-treatment, it is usually preferably 0.001 mole to 5 moles relative to 1 mole of the epoxy derivative (8), more preferably 0.001 mole to 3 moles, and even more preferably 0.001 mole to 1 mole.

Reaction (A) can be carried out in the presence or absence of a solvent. The solvent is not particularly limited as long as it does not interfere with the reaction. For example, there may be mentioned aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; alcohols such as methanol, ethanol, t-butanol, and the like; esters such as ethyl acetate, butyl acetate, and the like. Among these, the ethers are preferable and tetrahydrofuran is more preferable. The solvent may be used singly or by mixing two or more kinds. When a solvent is used, the amount thereof used is, from the viewpoint of economic efficiency and ease of after-treatment, preferably 0.1 mass times to 100 mass times based on the epoxy derivative (8), and more preferably 0.1 mass times to 10 mass times.

A reaction temperature of Reaction (A) varies depending on the kinds of the epoxy derivative (8), the acid, and the solvent used, but it is usually preferably −30° C. to 200° C., more preferably, from the viewpoint of economic efficiency and reaction rate, −30° C. to 150° C., and even more preferably −30 to 70° C. A reaction pressure of Reaction (A) is not particularly limited, but it is usually preferable to carry out the reaction under ordinary pressure. A reaction time of Reaction (A) varies depending on the kinds of the epoxy derivative (8), the acid, and the solvent used, but it is usually preferably 0.5 hour to 48 hours, and more preferably, from the viewpoint of economic efficiency, 0.5 hour to 24 hours.

Reaction (A) can be stopped by the addition of a base. Such a base includes metal alkoxides such as sodium methoxide, potassium t-butoxide, and the like; alkali metal hydrides such as sodium hydride, potassium hydride, and the like; alkaline earth metal hydrides such as magnesium hydride, calcium hydride, and the like; alkali metal hydroxides such as sodium hydroxide, potassium hydroxide, and the like; alkaline earth metal hydroxides such as magnesium hydroxide, calcium hydroxide, and the like; alkali metal carbonates such as sodium carbonate, potassium carbonate, and the like; alkaline earth metal carbonates such as magnesium carbonate, calcium carbonate, and the like; alkali metal bicarbonates such as sodium bicarbonate, potassium bicarbonate, and the like; tertiary amines such as triethylamine, tributylamine, diisopropylethylamine, 1,4-diazabicyclo[2.2.2]octane, and the like; and nitrogen-containing heterocyclic aromatic compounds such as pyridine, 2-picoline, 2,6-lutidine, and the like. The amount of the base added is preferably 0.1 mole to 100 moles relative to 1 mole of an acid used in Reaction (A), and, from the viewpoint of economic efficiency, more preferably 0.1 mole to 10 moles.

(Reaction (B))

Hereinafter, Reaction (B) will be described.

The base, which can be used in Reaction (B) includes, for example, metal alkoxides such as sodium methoxide, potassium t-butoxide, and the like; alkali metal hydrides such as sodium hydride, potassium hydride, and the like; alkaline earth metal hydrides such as magnesium hydride, calcium hydride, and the like; alkali metal hydroxides such as sodium hydroxide, potassium hydroxide, and the like; alkaline earth metal hydroxides such as magnesium hydroxide, calcium hydroxide, and the like; alkali metal carbonates such as sodium carbonate, potassium carbonate, and the like; alkaline earth metal carbonates such as magnesium carbonate, calcium carbonate, and the like; alkali metal bicarbonates such as sodium bicarbonate, potassium bicarbonate, and the like; tertiary amines such as triethylamine, tributylamine, diisopropylethylamine, 1,4-diazabicyclo[2.2.2]octane, and the like; and nitrogen-containing heterocyclic aromatic compounds such as pyridine, 2-picoline, 2,6-lutidine, and the like. Among these, the metal alkoxides, the alkali metal hydrides, the alkali metal hydroxides, and the tertiary amines are preferable, and potassium t-butoxide, sodium hydride, potassium hydride, and 1,4-diazabicyclo[2.2.2]octane are more preferable. The amount of the base used is not particularly limited, but, from the viewpoint of reaction rate, economic efficiency, and ease of after-treatment, it is preferably 0.5 mole to 20 moles relative to the epoxy derivative (8), more preferably 0.5 mole to 10 moles, and even more preferably 0.5 mole to 5 moles.

Reaction (B) can be carried out in the presence or absence of a solvent. The solvent is not particularly limited as long as it does not interfere with the reaction. For example, there may be mentioned aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; alcohols such as methanol, ethanol, t-butanol, and the like; esters such as ethyl acetate, butyl acetate, and the like. Among these, the alcohols are preferable and t-butanol is more preferable. The solvent may be used singly or by mixing two or more kinds. When a solvent is used, the amount thereof used is, from the viewpoint of economic efficiency and ease of after-treatment, preferably 0.1 mass times to 100 mass times based on the epoxy derivative (8), and more preferably 0.1 mass times to 35 mass times.

The reaction temperature of Reaction (B) varies depending on the kinds of the epoxy derivative (8), the base, and the solvent used, but it is usually preferably −30° C. to 200° C., more preferably, from the viewpoint of economic efficiency and reaction rate, −30° C. to 150° C., and even more preferably −30° C. to 85° C. The reaction pressure of Reaction (B) is not particularly limited, but it is usually preferable to carry out the reaction under ordinary pressure. The reaction time of Reaction (B) varies depending on the kinds of the epoxy derivative (8), the base, and the solvent used, but it is usually preferably 0.5 hour to 48 hours, and more preferably, from the viewpoint of economic efficiency, 0.5 hour to 24 hours.

Reaction (B) can be stopped by the addition of an acid. Such an acid includes mineral acids such as hydrochloric acid, sulfuric acid, and the like; organic acids such as methanesulfonic acid, p-toluenesulfonic acid, trifluoromethanesulfonic acid, and the like; and Lewis acids such as boron trifluoride, aluminum trichloride, dibutyltin dilaurate, and the like. The amount of the acid added is preferably 0.1 mole to 100 moles relative to 1 mole of the base used in Reaction (B), and more preferably, from the viewpoint of economic efficiency and reaction yield, 0.1 mole to 10 moles.

(Isolation and Purification of Alcohol Derivative (2))

Isolation and purification of the alcohol derivative (2) from a reaction mixture obtained in the above-described Reaction (A) or the above-described Reaction (B) can be carried out by a method generally used in isolation and purification of an organic compound. For example, after stopping the reaction, water is added to the reaction mixture, the mixture is thereafter separated into an organic layer and an aqueous layer, and the organic layer is washed with water. Further, if necessary, the aqueous layer is extracted using an organic solvent and the latter is combined with the organic layer. Subsequently, by concentrating the organic layer obtained, the alcohol derivative (2) can be isolated. And, if necessary, the alcohol derivative (2) of high purity can be obtained by a usual purification means such as recrystallization, distillation, silica gel column chromatography, and the like.

Specific examples of the alcohol derivative (2) which can be produced by the above-described process are shown in the following, but the present invention is not particularly limited to these:

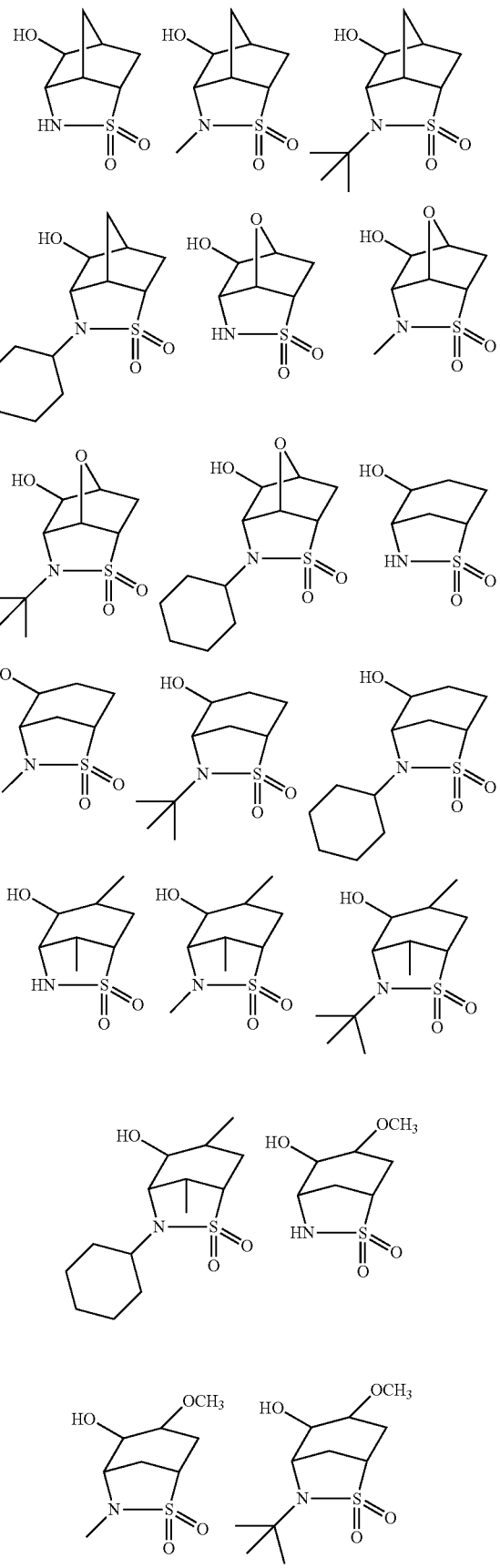

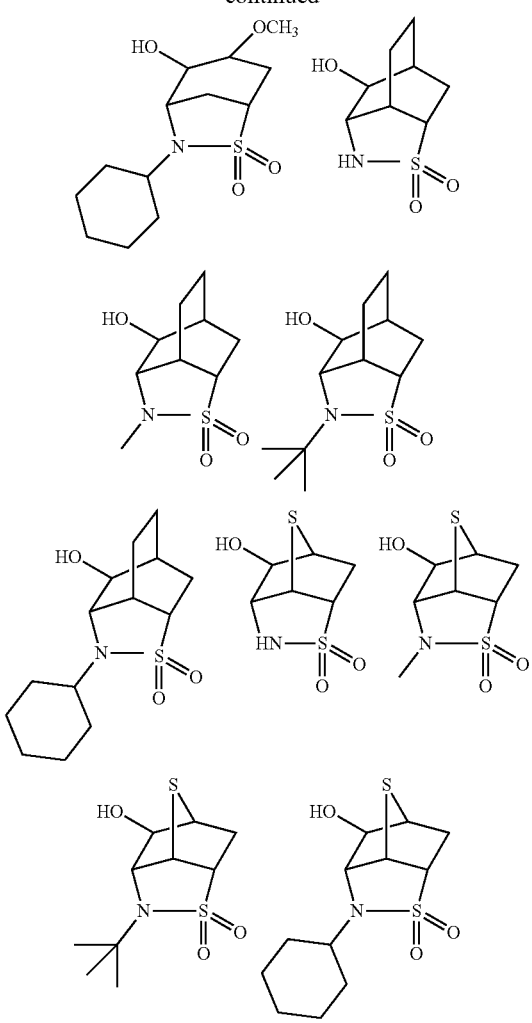

(Reaction (C))

Hereinafter, Reaction (C) will be described.

The acrylic acid esterifying agent which can be used in Reaction (C) includes, for example, compounds represented by the following general formula (5), (9), (10), (11), (12), or the like:

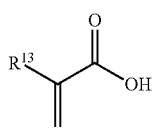

(5)

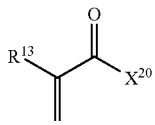

(9)

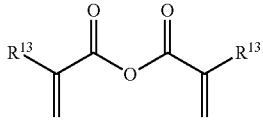

(10)

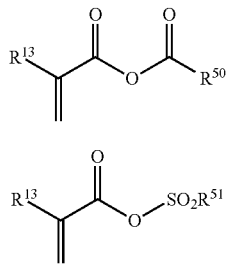

(11)

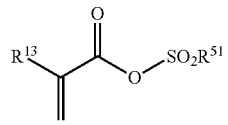

(12)

(wherein, $R^{13}$ is as defined previously; $R^{50}$ represents a t-butyl group or a 2,4,6-trichlorophenyl group; $R^{51}$ represents a methyl group or a p-tolyl group; and $X^{20}$ represents a chlorine atom, a bromine atom, or an iodine atom.)

The amount of the acrylic acid esterifying agent used is not particularly limited, but, from the viewpoint of economic efficiency and ease of after-treatment, it is usually preferably 0.8 to 20 moles relative to 1 mole of the alcohol derivative (2), and more preferably 0.8 mole to 10 moles.

In Reaction (C), when an acrylic acid (a compound represented by the general formula (5)) is used as the acrylic acid esterifying agent, the reaction is preferably carried out in the presence of an acid from the viewpoint of making the reaction proceed smoothly. When an acid halide (a compound represented by the general formula (9)), an acid anhydride (a compound represented by the general formula (10)), or a compound represented by the general formula (11) or (12) is used as the acrylic acid esterifying agent, the reaction is preferably carried out in the presence of a base from the viewpoint of making the reaction proceed smoothly.

The acid includes, for example, mineral acids such as hydrochloric acid, sulfuric acid, and the like; organic acids such as methanesulfonic acid, p-toluenesulfonic acid, trifluoromethanesulfonic acid, and the like; Lewis acids such as boron trifluoride, aluminum trichloride, dibutyltin dilaurate, and the like. Among these, the mineral acids or the organic acids are preferable, and sulfuric acid or p-toluenesulfonic acid is more preferable. The acid may be used singly or in a combination of two or more kinds. The amount of the acid used is not particularly limited, but, from the viewpoint of reaction rate, economic efficiency, and ease of after-treatment, it is usually preferably 0.001 mole to 5 moles relative to 1 mole of the alcohol derivative (2), more preferably 0.001 mole to 3 moles, and even more preferably 0.001 mole to 1 mole.

The base includes alkali metal hydrides such as sodium hydride, potassium hydride, and the like; alkali metal hydroxides such as sodium hydroxide, potassium hydroxide, and the like; alkali metal carbonates such as sodium carbonate, potassium carbonate, and the like; tertiary amines such as triethylamine, tributylamine, 1,4-diazabicyclo[2.2.2]octane, and the like; and nitrogen-containing heterocyclic aromatic compounds such as pyridine, 2,6-lutidine, and the like. Among these, the tertiary amines and the nitrogen-containing heterocyclic aromatic compounds are preferable, and triethylamine, 1,4-diazabicyclo[2.2.2]octane, pyridine, and 2,6-lutidine are more preferable. The amount of the base used is not particularly limited, but, from the viewpoint of economic efficiency and ease of after-treatment, it is usually preferably 0.1 to 10 moles relative to 1 mole of the alcohol derivative (2), and more preferably 0.2 to 6 moles.

Reaction (C) can be carried out in the presence or absence of a solvent. The solvent is not particularly limited as long as it does not interfere with the reaction and includes, for example, aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; esters such as ethyl acetate, butyl acetate, and the like. Among these, the ethers are preferable, and tetrahydrofuran is more preferable. The solvent may be used in one kind singly or by mixing two or more kinds. When a solvent is used, the amount thereof used is, from the viewpoint of economic efficiency and ease of after-treatment, preferably 0.1 mass times to 100 mass times based on the alcohol derivative (2), and more preferably 0.1 mass times to 20 mass times.

Reaction (C) can be carried out in the presence or absence of a polymerization inhibitor. The polymerization inhibitor is not particularly limited and includes, for example, quinone compounds such as hydroquinone, methoxyphenol, benzoquinone, toluquinone, and the like; alkylphenol compounds such as p-tert-butylcatechol, 2,6-di-tert-butylphenol, 2,4-di-tert-butylphenol, 2-tert-butyl-4,6-dimethylphenol, and the like; amine compounds such as phenothiazine and the like. The polymerization inhibitor may be used singly or in combination of two or more kinds. When a polymerization inhibitor is used, the amount thereof used is preferably 0.001 mass ppm to 5 mass % relative to the mass of the whole reaction mixture, more preferably 0.001 mass ppm to 1 mass %, and even more preferably 0.001 mass ppm to 0.5 mass %.

The reaction temperature of Reaction (C) varies depending on the kinds of the alcohol derivative (2) and the solvent used, but it is usually preferably −30° C. to 200° C., more preferably, from the viewpoint of economic efficiency and reaction rate, −30° C. to 150° C., and even more preferably −30 to 50° C. The reaction pressure of Reaction (C) is not particularly limited, but it is usually preferable to carry out the reaction under ordinary pressure or reduced pressure. The reaction time of Reaction (C) varies depending on the kinds of the alcohol derivative (2) and the solvent used, but it is usually preferably 0.5 hour to 48 hours, and more preferably, from the viewpoint of economic efficiency, 0.5 hour to 24 hours.

Isolation and purification of the acrylic acid ester derivative (1-a) from a reaction mixture obtained in Reaction (C) can be carried out by a method generally used in isolation and purification of an organic compound. For example, after stopping the reaction, water is added to the reaction mixture, the mixture is thereafter separated into an organic layer and an aqueous layer, and the organic layer is washed with water. Further, if necessary, the aqueous layer is extracted with an organic solvent and the latter is combined with the organic layer. Subsequently, by concentrating the organic layer obtained, the acrylic acid ester derivative (1-a) can be isolated. And, if necessary, the acrylic acid ester derivative (1-a) of high purity can be obtained by a usual purification means such as recrystallization, distillation, silica gel column chromatography, and the like.

Specific examples of the acrylic acid ester derivative (1-a) obtained by Reaction (C) are shown in the following, but the present invention is not particularly limited to these:

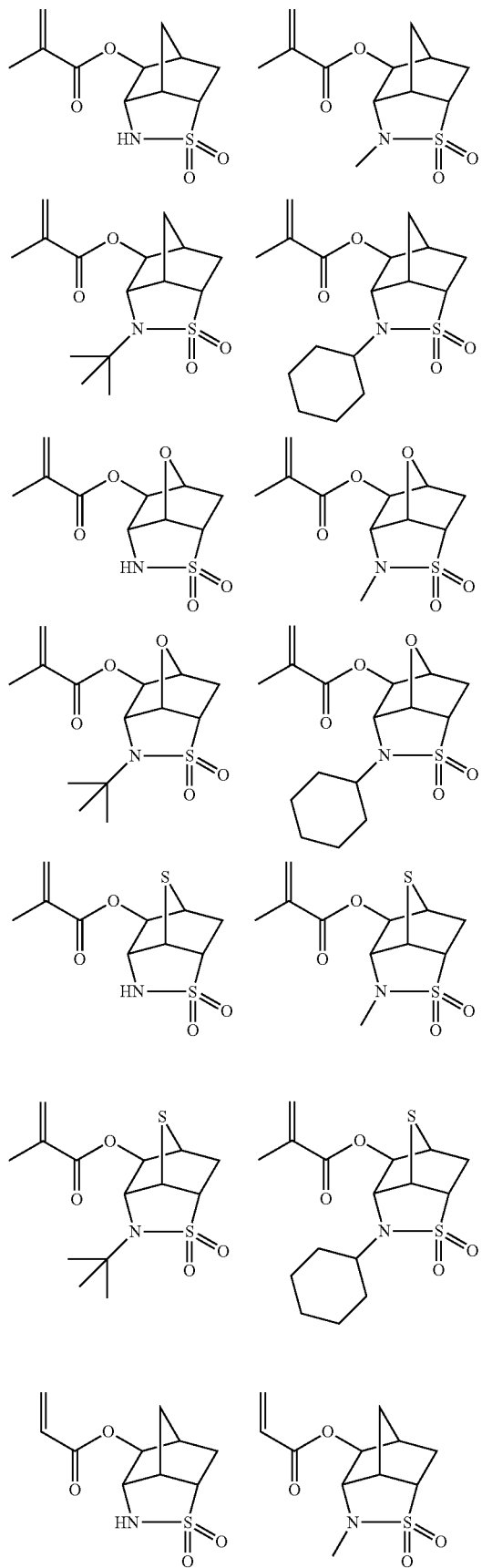

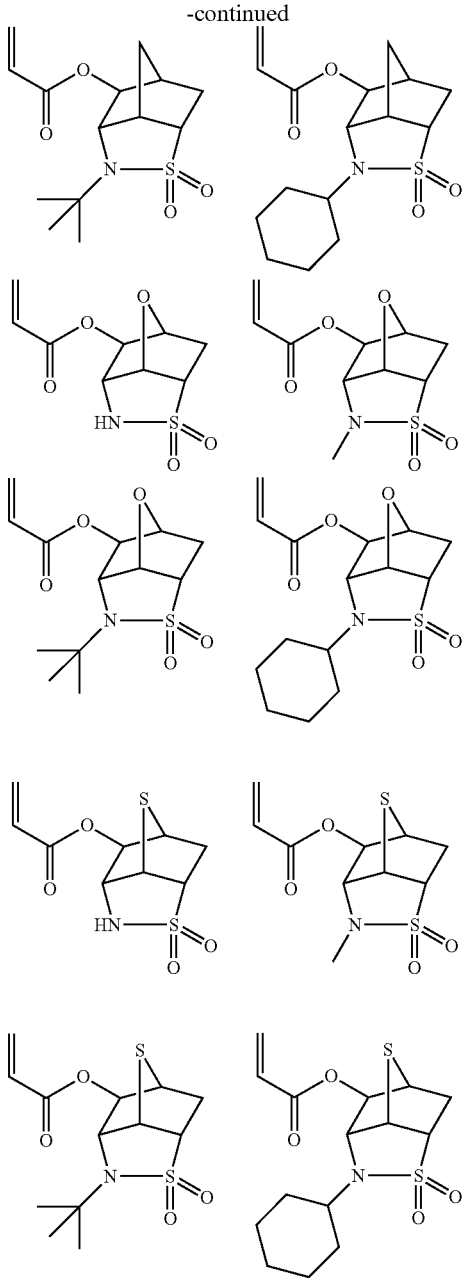

(Reaction (D))

Hereinafter, Reaction (D) will be described.

The carbonyl compound (3) used in Reaction (D) includes, for example, aldehyde compounds such as formaldehyde, acetaldehyde, propionaldehyde, butylaldehyde, and the like; and ketone compounds such as acetone, methyl ethyl ketone, diethyl ketone, methyl isopropyl ketone, methyl isobutyl ketone, and the like.

The amount of the carbonyl compound (3) used is not particularly limited, but, from the viewpoint of economic efficiency and ease of after-treatment, it is usually preferably 0.8 to 20 moles relative to 1 mole of the alcohol derivative (2), and more preferably 0.8 mole to 10 moles.

Reaction (D) is carried out in the presence of hydrogen halide. Such a hydrogen halide includes, for example, gaseous hydrogen halide such as a hydrogen chloride gas, a hydrogen bromide gas, a hydrogen iodide gas, and the like; and hydrohalic acid such as hydrochloric acid, hydrobromic acid, hydroiodic acid, and the like. Among these, from the viewpoint of making the reaction proceed smoothly, the gaseous hydrogen halide is preferable and, from the viewpoint of stability of the ether derivative (4) produced, the hydrogen chloride gas is more preferable.

The amount of the hydrogen halide used is usually preferably 1 to 100 moles relative to 1 mole of the alcohol derivative (2), and more preferably 3 to 15 moles. When performing Reaction (D), it is even more preferable to add the hydrogen halide into the reaction system until the alcohol derivative (2) disappears. Furthermore, the hydrogen halide may be introduced into the reaction system continuously or intermittently from the start of the reaction. As a method of introducing the hydrogen halide, preferably mentioned is a method of bubbling the same into the reaction solution. Meanwhile, disappearance of the alcohol derivative (2) can be easily confirmed by gas chromatography.

Reaction (D) is usually preferably carried out in the presence of a solvent. The solvent is not particularly limited as long as it does not interfere with the reaction and includes, for example, aliphatic hydrocarbons such as pentane, hexane, heptane, octane, and the like; aromatic hydrocarbons such as toluene, xylene, cymene, and the like; halogenated hydrocarbons such as dichloromethane, 1,2-dichloroethane, chloroform, carbon tetrachloride, and the like. Among these, the halogenated hydrocarbons are preferable; dichloromethane, 1,2-dichloroethane, and chloroform are more preferable; and dichloromethane is even more preferable. The solvent may be used singly or in combination of two or more kinds. The amount of the solvent used is, from the viewpoint of economic efficiency and ease of after-treatment, preferably 0.1 mass times to 100 mass times based on the alcohol derivative (2), and more preferably 0.1 mass times to 50 mass times.

The reaction temperature of Reaction (D) varies depending on the kinds and the like of the alcohol derivative (2), the carbonyl compound (3), the hydrogen halide, and the solvent used, but, from the viewpoint of solubility of the raw materials and the hydrogen halide, it is usually preferably −80° C. to 100° C., more preferably, −50° C. to 70° C., and even more preferably −30° C. to 50° C. The reaction pressure of Reaction (D) is not particularly limited, but it is easy and preferable to carry out the reaction under ordinary pressure. The reaction time of Reaction (D) is not particularly limited. Usually, the reaction is preferably carried out until disappearance of the alcohol derivative (2) is confirmed.

Isolation and purification of the ether derivative (4) from a reaction mixture obtained in Reaction (D) can be carried out by a method generally used in isolation and purification of an organic compound. For example, a crude ether derivative (4) can be isolated by, after completion of the reaction, separating water generated as a byproduct and concentrating the organic layer. And, if necessary, the ether derivative (4) of high purity can be obtained by a usual purification means such as recrystallization, distillation, silica gel column chromatography, and the like. In addition, for the next step, Reaction (E), the organic layer obtained in Reaction (D) may be used as is, the above-described crude ether derivative (4) may be used, or the ether derivative (4) after purification may be used.

Specific examples of the ether derivative (4) obtained by Reaction (D) are shown in the following, but the present invention is not particularly limited to these:

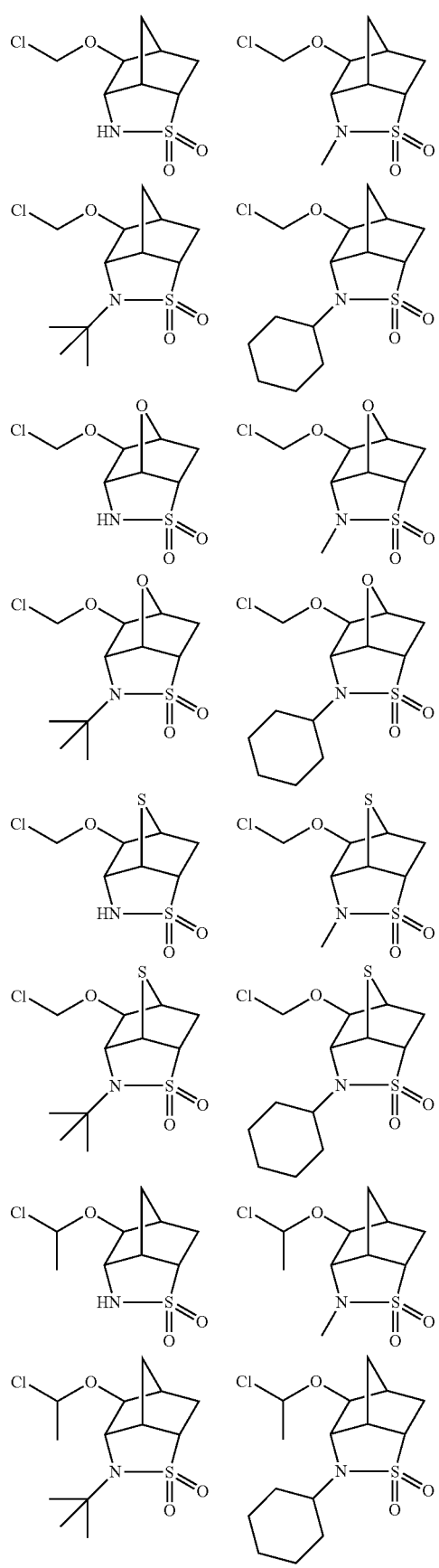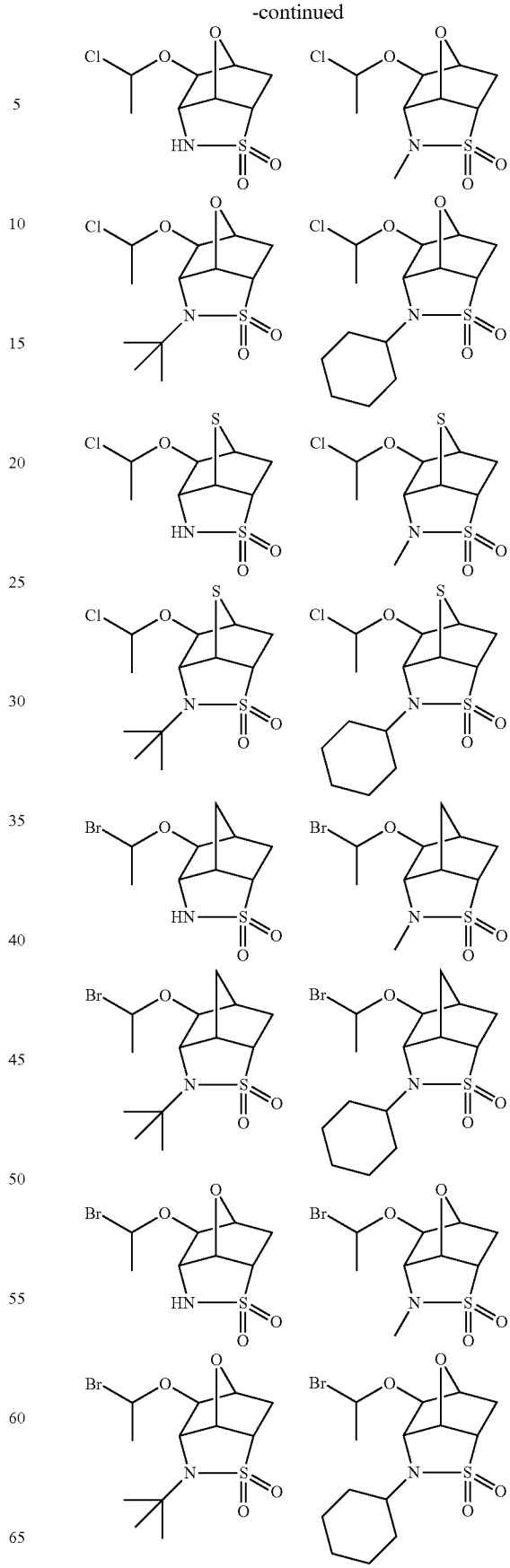

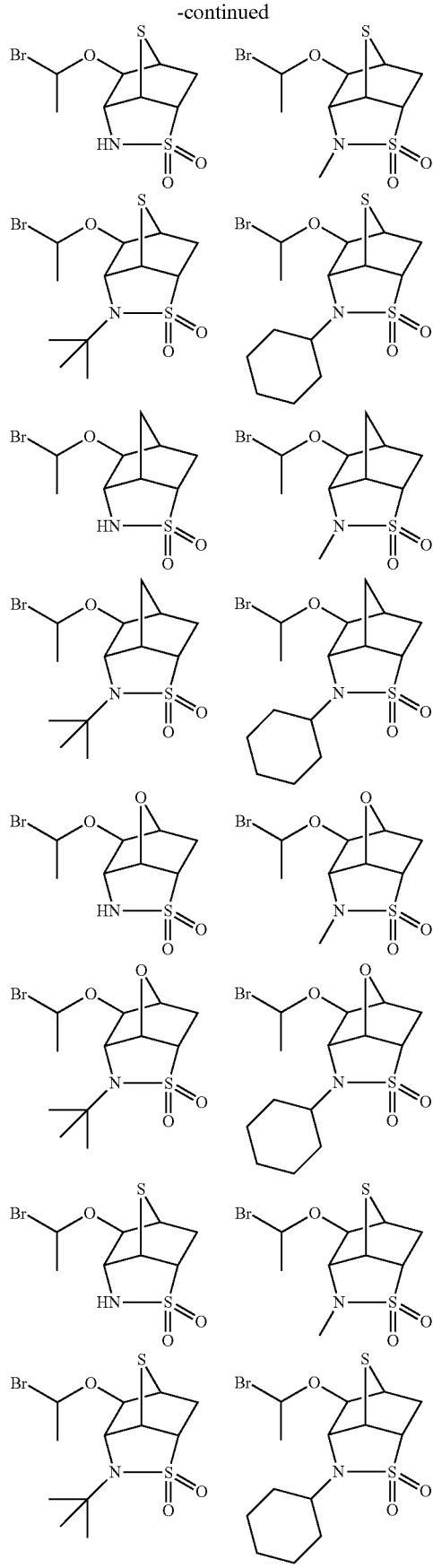
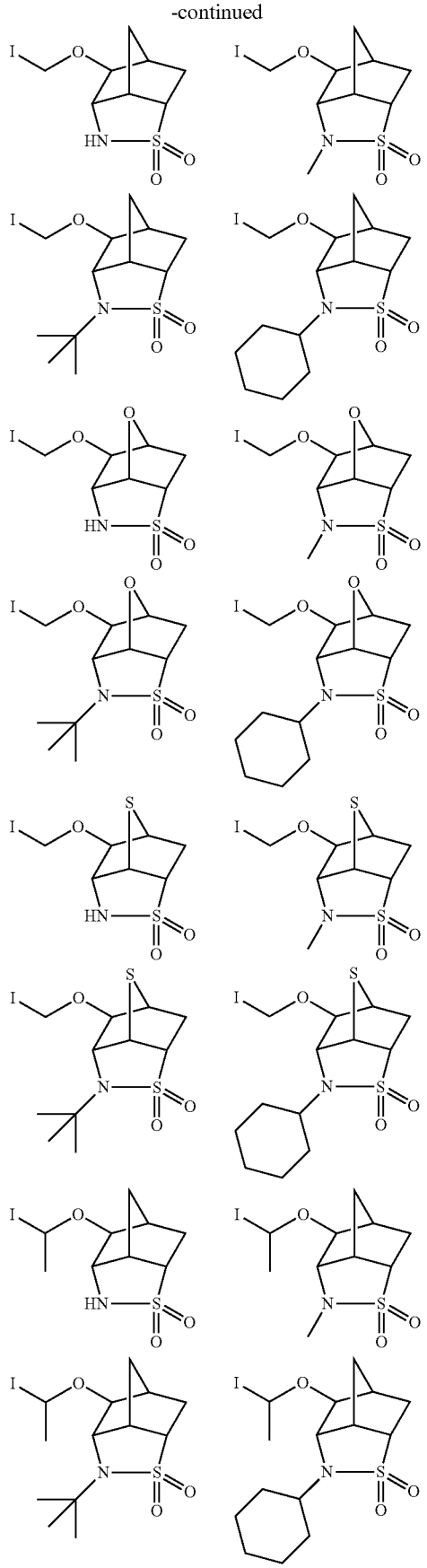

-continued

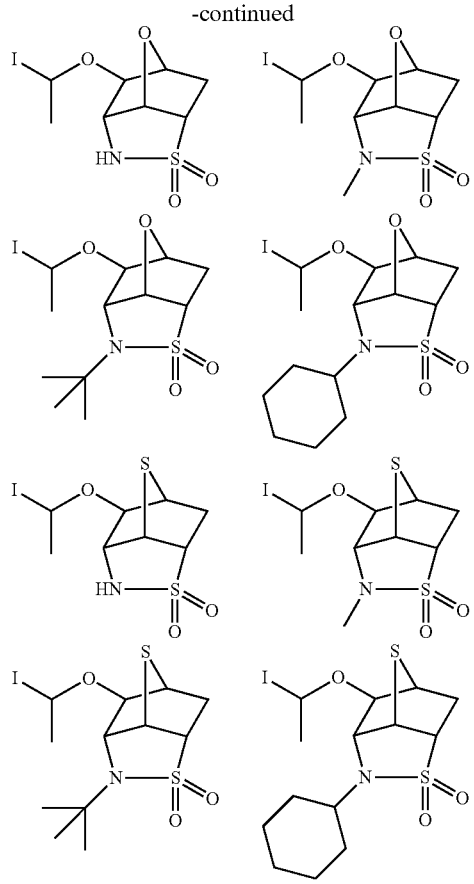

(Reaction (E))

Hereinafter, Reaction (E) will be described.

The acrylic acid (5) used in Reaction (E) includes, for example, acrylic acid, methacrylic acid, 2-(trifluoromethyl) acrylic acid, and the like. The amount of the acrylic acid (5) used is, from the viewpoint of economic efficiency and ease of after-treatment, usually preferably 0.7 to 20 moles relative to 1 mole of the ether derivative (4), more preferably 0.7 to 5 moles, and even more preferably 1 to 5 moles.

Reaction (E) is preferably carried out in the presence of a base. Such a base includes, for example, alkali metal hydrides such as sodium hydride, potassium hydride, and the like; alkali metal hydroxides such as sodium hydroxide, potassium hydroxide, and the like; alkali metal carbonates such as sodium carbonate, potassium carbonate, and the like; tertiary amines such as triethylamine, tributylamine, 1,4-diazabicyclo[2.2.2]octane, 4-dimethylaminopyridine, and the like; and nitrogen-containing heterocyclic aromatic compounds such as pyridine, 2,6-lutidine, and the like. Among these, the tertiary amines and the nitrogen-containing heterocyclic compounds are preferable; triethylamine, 1,4-diazabicyclo[2.2.2] octane, pyridine, and 2,6-lutidine are more preferable; and triethylamine is even more preferable. The amount of the base used is, from the viewpoint of economic efficiency and ease of after-treatment, usually preferably 0.1 mole to 10 moles relative to 1 mole of the ether derivative (4), and more preferably 0.2 to 6 moles.

Reaction (E) can be carried out in the presence or absence of a solvent. The solvent is not particularly limited as long as it does not interfere with the reaction. For example, there may be mentioned aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; alcohols such as methanol, ethanol, t-butanol, and the like; esters such as ethyl acetate, butyl acetate, and the like. Among these, the halogenated hydrocarbons are preferable and dichloromethane, 1,2-dichloroethane, chloroform are more preferable; and dichloromethane is even more preferable. The solvent may be used singly or by mixing two or more kinds. When a solvent is used, the amount thereof used is, from the viewpoint of economic efficiency and ease of after-treatment, preferably 0.1 mass times to 100 mass times based on the ether derivative (4), and more preferably 0.1 mass times to 50 mass times.

Reaction (E) can be carried out in the presence or absence of a polymerization inhibitor. The polymerization inhibitor is not particularly limited and includes, for example, quinone compounds such as hydroquinone, methoxyphenol, benzoquinone, toluquinone, and the like; alkylphenol compounds such as p-tert-butylcatechol, 2,6-di-tert-butylphenol, 2,4-di-tert-butylphenol, 2-tert-butyl-4,6-dimethylphenol, and the like; amine compounds such as phenothiazine and the like. The polymerization inhibitor may be used singly or in combination of two or more kinds. When a polymerization inhibitor is used, the amount thereof used is preferably 0.001 mass ppm to 5 mass % relative to the mass of the whole reaction mixture, more preferably 0.001 mass ppm to 1 mass %, and even more preferably 0.001 mass ppm to 0.5 mass %.

The reaction temperature of Reaction (E) varies depending on the kinds of the ether derivative (4), the acrylic acid (5), the base, and the solvent used, but it is preferably −80° C. to 200° C., more preferably, from the viewpoint of inhibition of polymerization of the acrylic acid (5) and the acrylic acid ester derivative (1-b) obtained in the reaction system and from the viewpoint of solubility of the raw materials, the base, and the like in the solvent, −80° C. to 150° C., even more preferably −50° C. to 100° C., and especially preferably −30° C. to 40° C. The reaction pressure of Reaction (E) is not particularly limited, but it is easy and preferable to carry out the reaction under ordinary pressure. The reaction time of Reaction (E) varies depending on the kinds of the ether derivative (4), the acrylic acid (5), the base, and the solvent used, but it is usually preferably 0.5 hour to 48 hours, and more preferably 1 hour to 24 hours.

Isolation and purification of the acrylic acid ester derivative (1-b) from a reaction mixture obtained in Reaction (E) can be carried out by a method generally used in isolation and purification of an organic compound. For example, after completion of the reaction, water is added to the reaction mixture, the mixture is thereafter separated into an organic layer and an aqueous layer, and the organic layer is washed with water. And, if necessary, the aqueous layer is extracted using an organic solvent, and by combining and concentrating the organic layers, there can be isolated the acrylic acid ester derivative (1-b). And, if necessary, the acrylic acid ester derivative (1-b) of high purity can be obtained by a usual purification means such as recrystallization, distillation, silica gel column chromatography, and the like.

Specific examples of the acrylic acid ester derivative (1-b) are shown in the following, but the present invention is not particularly limited to these:

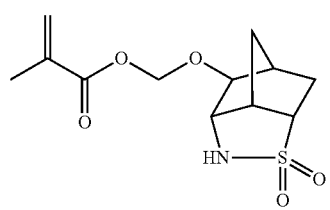
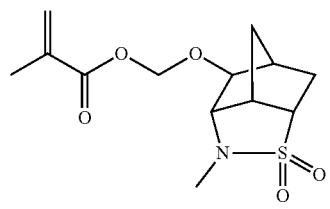
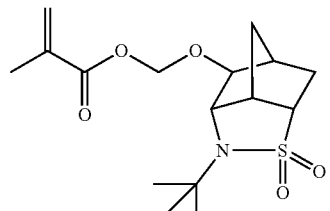
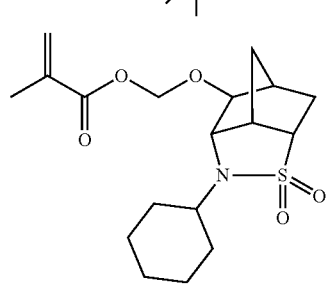
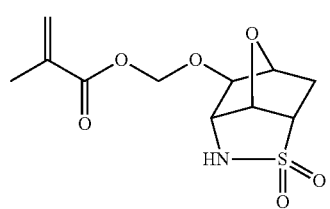
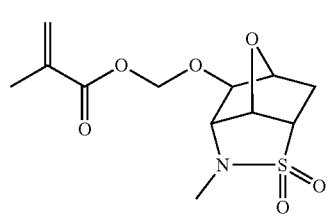
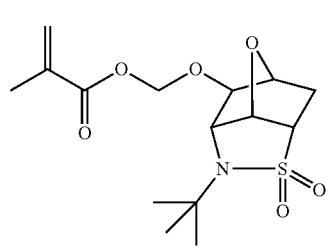
-continued
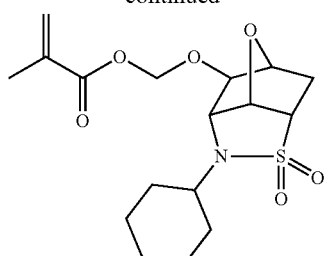
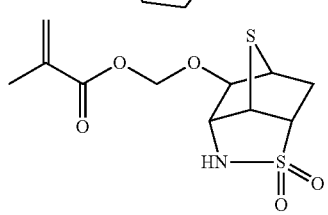
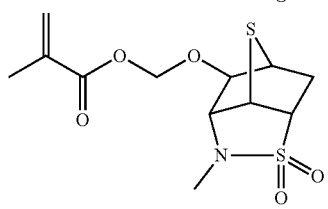
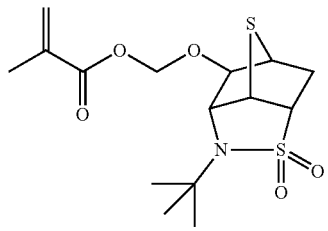
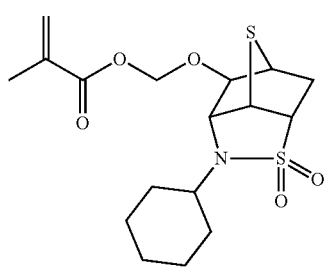
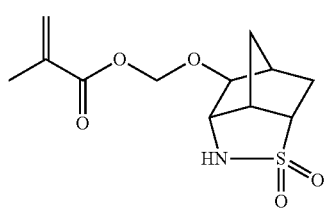
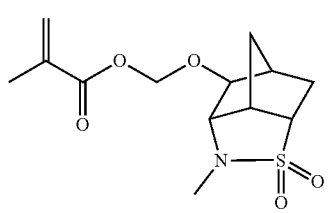

-continued

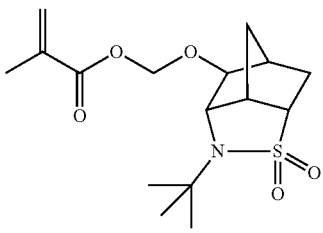
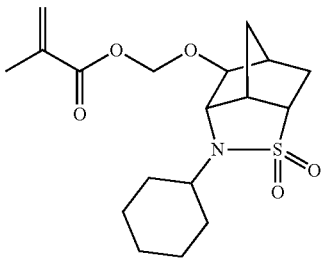
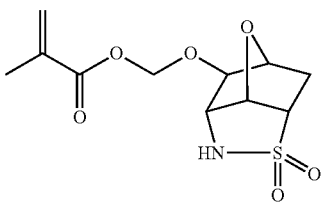
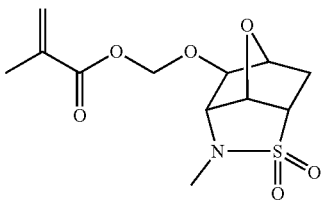
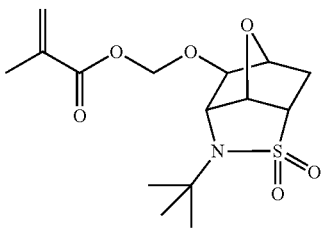
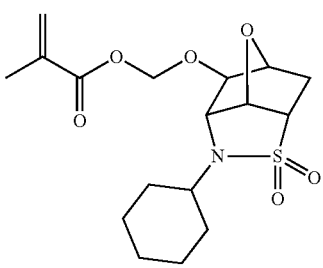
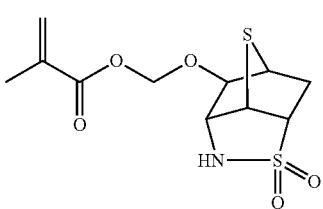

-continued

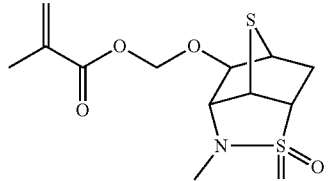
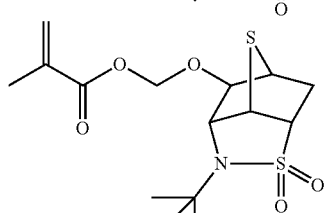
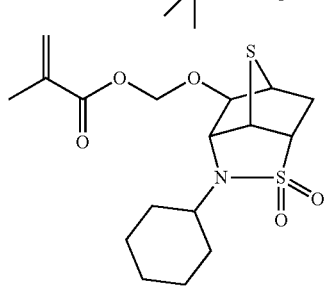

(Reaction (F))

Hereinafter, Reaction (F) will be described.

The amount of the haloesterifying agent (6) used in Reaction (F) is, from the viewpoint of economic efficiency and ease of after-treatment, usually preferably 0.8 to 20 moles relative to 1 mole of the alcohol derivative (2), and more preferably 0.8 mole to 10 moles.

In Reaction (F), when a compound wherein A is —OH is used as the haloesterifying agent (6), the reaction is preferably carried out in the presence of an acid from the viewpoint of making the reaction proceed smoothly. On the other hand, when a compound wherein A is other than —OH is used as the haloesterifying agent (6), the reaction is preferably carried out in the presence of a base from the viewpoint of making the reaction proceed smoothly.

The acid includes, for example, mineral acids such as hydrochloric acid, sulfuric acid, and the like; organic acids such as methanesulfonic acid, p-toluenesulfonic acid, trifluoromethanesulfonic acid, and the like; Lewis acids such as boron trifluoride, aluminum trichloride, dibutyltin dilaurate, and the like. Among these, the mineral acids or the organic acids are preferable, and sulfuric acid or p-toluenesulfonic acid is more preferable. The acid may be used singly or in a combination of two or more kinds. The amount of the acid used is not particularly limited, but, from the viewpoint of reaction rate, economic efficiency, and ease of after-treatment, it is usually preferably 0.001 mole to 5 moles relative to 1 mole of the alcohol derivative (2), more preferably 0.001 mole to 3 moles, and even more preferably 0.001 mole to 1 mole.

The base includes, for example, alkali metal hydrides such as sodium hydride, potassium hydride, and the like; alkali metal hydroxides such as sodium hydroxide, potassium hydroxide, and the like; alkali metal carbonates such as sodium carbonate, potassium carbonate, and the like; tertiary amines such as triethylamine, tributylamine, 1,4-diazabicyclo[2.2.2]octane, and the like; and nitrogen-containing heterocyclic aromatic compounds such as pyridine, 2,6-lutidine, and the like. Among these, the tertiary amines and the nitrogen-containing heterocyclic aromatic compounds are preferable; and triethylamine and pyridine are more preferable.

The amount of the base used is not particularly limited, but, from the viewpoint of economic efficiency and ease of after-treatment, it is usually preferably 0.8 mole to 10 moles relative to 1 mole of the alcohol derivative (2), and more preferably 0.8 to 6 moles.

Reaction (F) can be carried out in the presence or absence of a solvent. The solvent is not particularly limited as long as it does not interfere with the reaction and includes, for example, aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; esters such as ethyl acetate, butyl acetate, and the like. Among these, the ethers are preferable and tetrahydrofuran is more preferable. The solvent may be used singly or by mixing two or more kinds. When a solvent is used, the amount thereof used is, from the viewpoint of economic efficiency and ease of after-treatment, preferably 0.1 mass times to 100 mass times based on the alcohol derivative (2), and more preferably 0.1 mass times to 25 mass times.

The reaction temperature of Reaction (F) varies depending on the kinds of the alcohol derivative (2), the haloesterifying agent (6), the acid or the base, and the solvent used, but is usually preferably −30° C. to 200° C., more preferably, from the viewpoint of economic efficiency and rate of the reaction, −30° C. to 150° C., and even more preferably −30° C. to 70° C. The reaction pressure of Reaction (F) is not particularly limited, but it is preferable to carry out the reaction under ordinary pressure or reduced pressure. The reaction time of Reaction (F) varies depending on the kinds of the alcohol derivative (2), the haloesterifying agent (6), the acid or the base, and the solvent used, but it is usually preferably 0.5 hour to 48 hours, and, from the viewpoint of economic efficiency, more preferably 0.5 hour to 24 hours.

Isolation and purification of the haloester derivative (7) from a reaction mixture obtained in Reaction (F) can be carried out by a method generally used in isolation and purification of an organic compound. For example, after completion of the reaction, water is added to the reaction mixture, the mixture is thereafter separated into an organic layer and an aqueous layer, and, if necessary, the aqueous layer is extracted with an organic solvent. By combining, washing with water, and concentrating the organic layers, there can be isolated a crude haloester derivative (7). And, if necessary, the haloester derivative (7) of high purity can be obtained by a usual purification means such as recrystallization, distillation, silica gel column chromatography, and the like. In addition, for the next step, Reaction (G), the organic layer after washing with water, obtained in Reaction (F), may be used as is, the above-described crude haloester derivative (7) may be used, or the haloester derivative (7) after purification may be used.

Specific examples of the haloester derivative (7) obtained in Reaction (F) are shown in the following, but the present invention is not particularly limited to these:

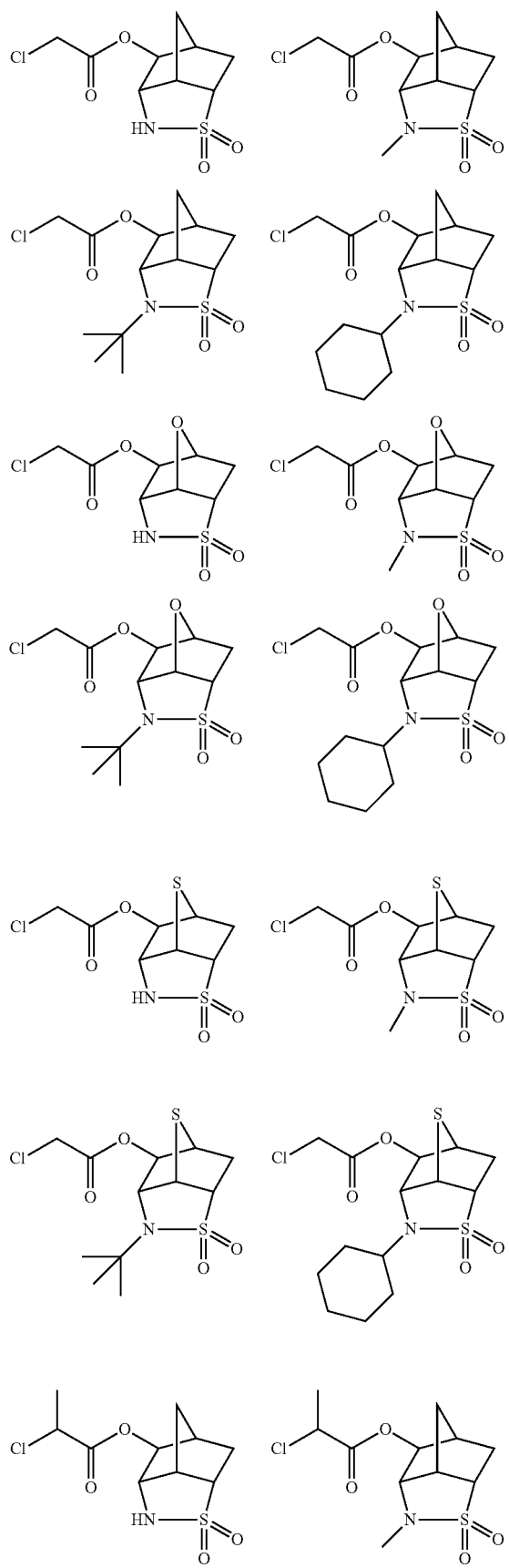

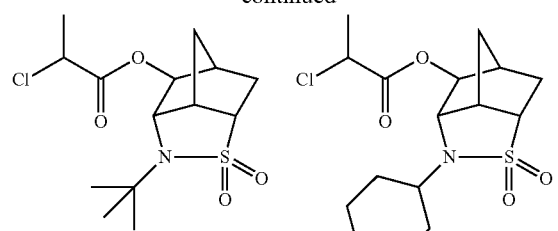
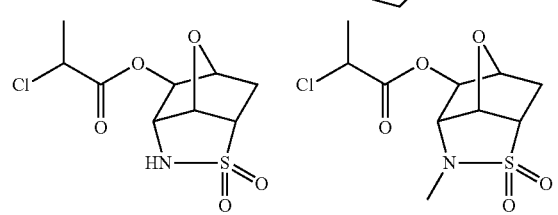
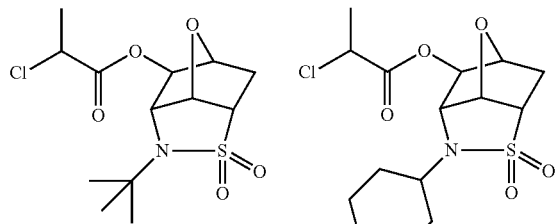
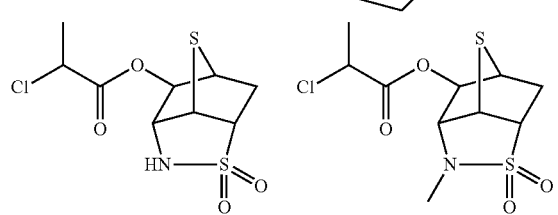
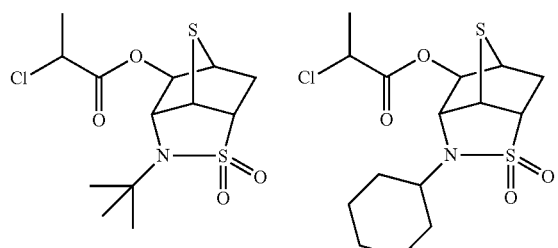
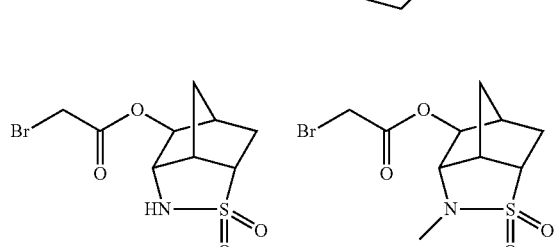
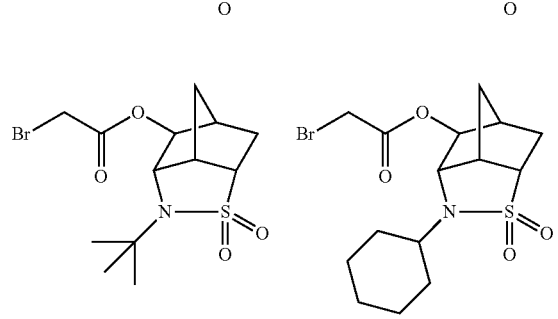
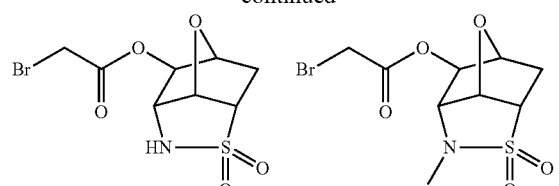
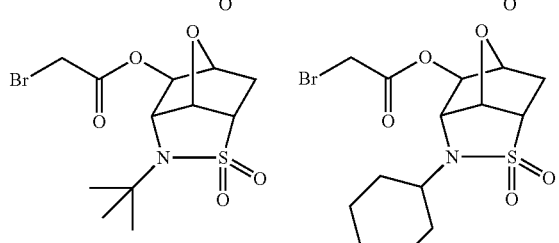
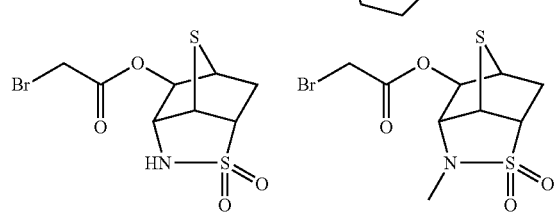
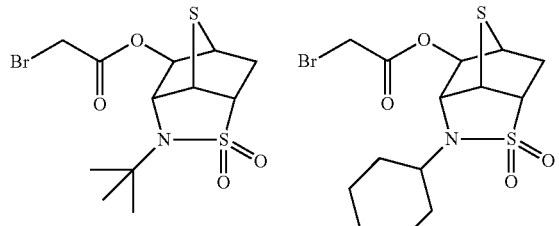
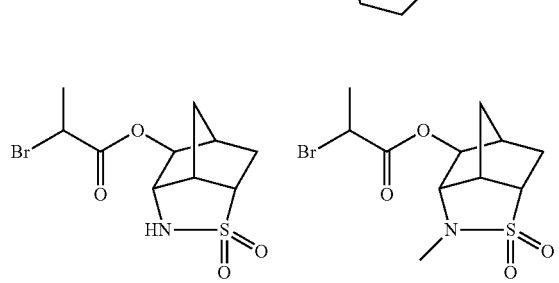
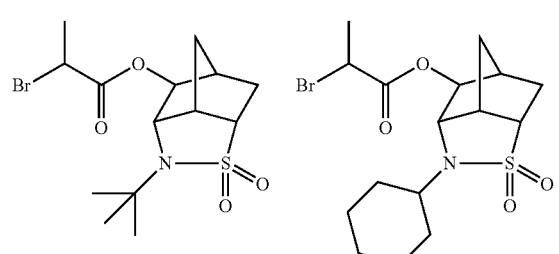
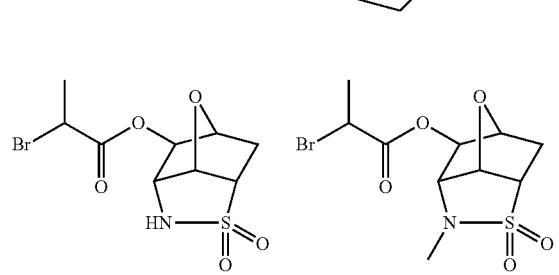

-continued
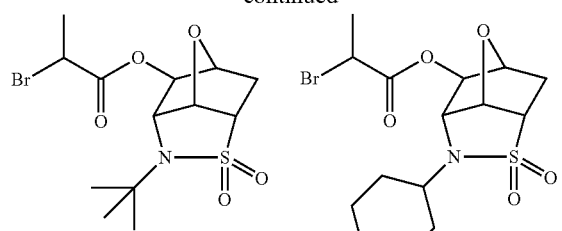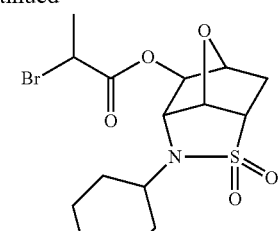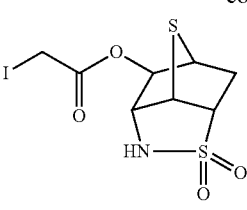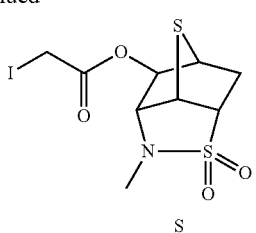
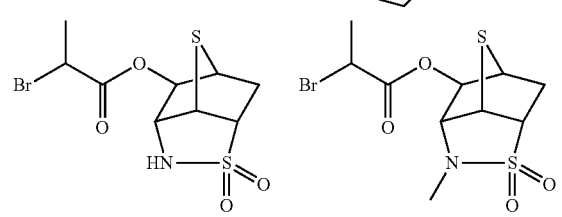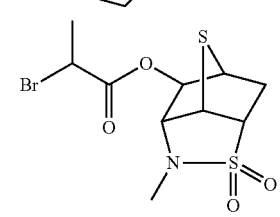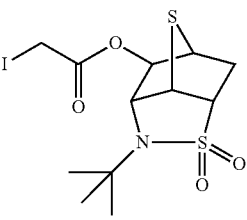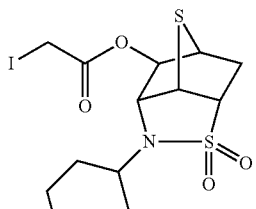
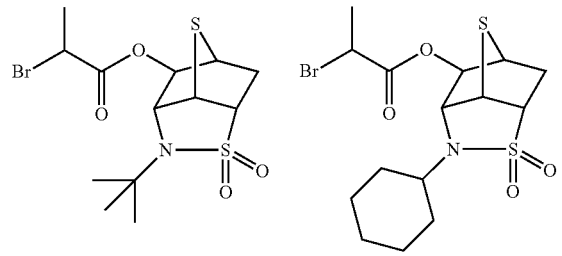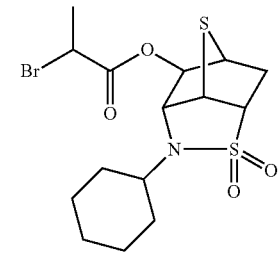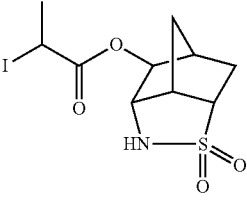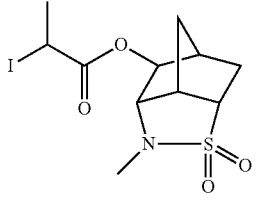
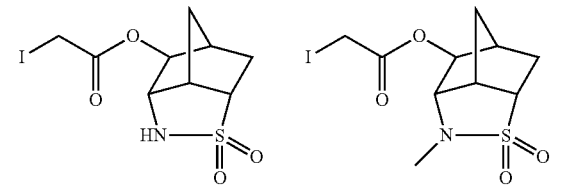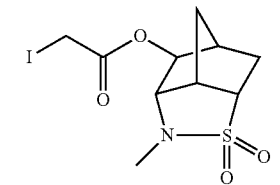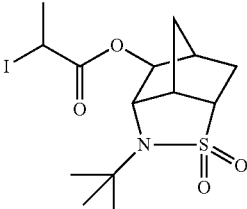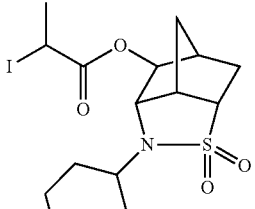
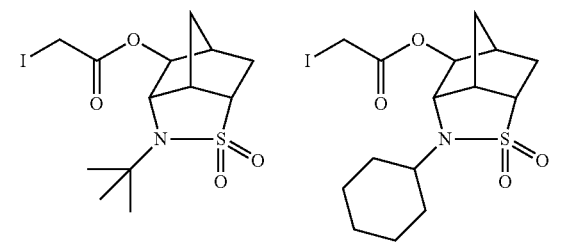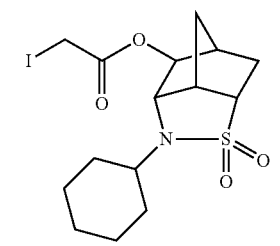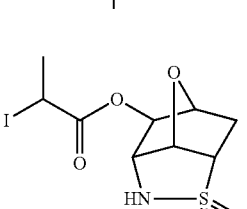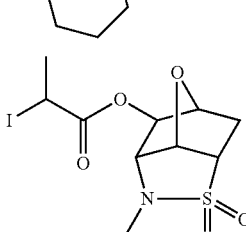
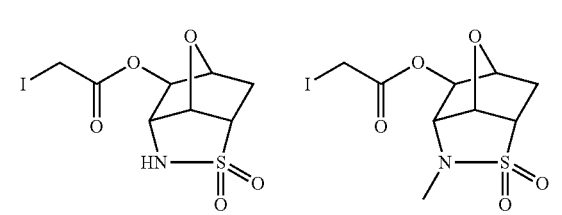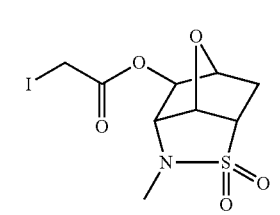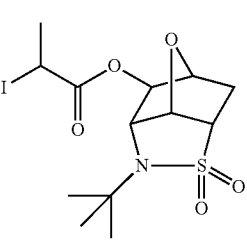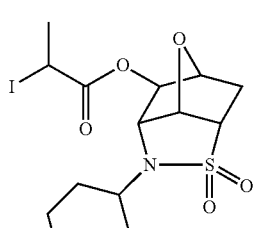
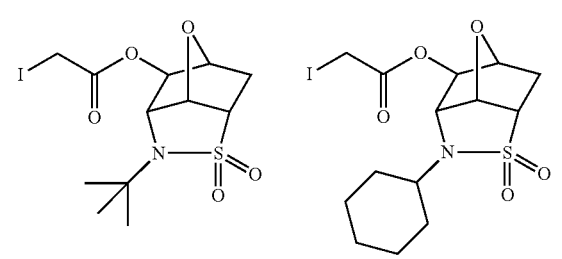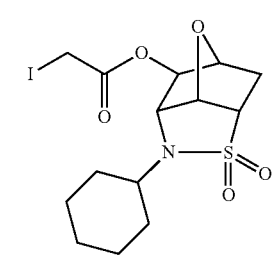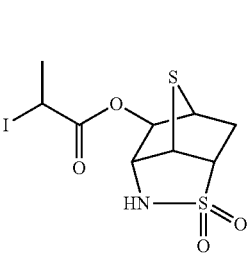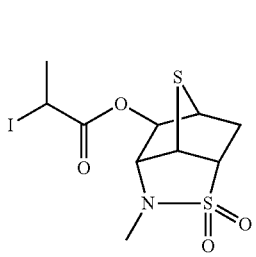

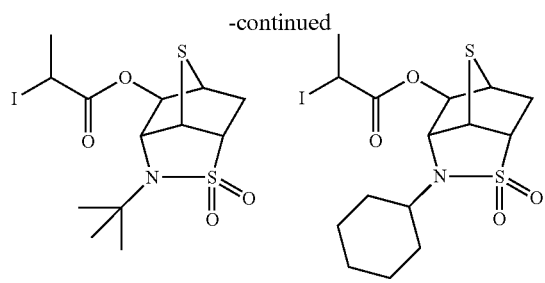

(Reaction (G))

Hereinafter, Reaction (G) will be described.

The acrylic acid (5) used in Reaction (G) includes, for example, acrylic acid, methacrylic acid, 2-(trifluoromethyl) acrylic acid, and the like. The amount of the acrylic acid (5) used is, from the viewpoint of economic efficiency and ease of after-treatment, usually preferably 0.7 to 20 moles relative to 1 mole of the haloester derivative (7), more preferably 0.7 to 5 moles, and even more preferably 1 to 5 moles.

Reaction (G) is preferably carried out in the presence of a base. Such a base includes, for example, alkali metal hydrides such as sodium hydride, potassium hydride, and the like; alkali metal hydroxides such as sodium hydroxide, potassium hydroxide, and the like; alkali metal carbonates such as sodium carbonate, potassium carbonate, and the like; tertiary amines such as triethylamine, tributylamine, 4-dimethylaminopyridine, and the like; and nitrogen-containing heterocyclic compounds such as pyridine, and the like. Among these, the tertiary amines, the nitrogen-containing heterocyclic aromatic compounds, and the alkali metal carbonates are preferable, and the alkali metal carbonates are more preferable.

The amount of the base used is, from the viewpoint of economic efficiency and ease of after-treatment, usually preferably 0.1 mole to 10 moles relative to 1 mole of the haloester derivative (7), and more preferably 0.2 to 6 moles.

Meanwhile, in order to facilitate a reaction between the haloester derivative (7) and the acrylic acid (5), Reaction (G) may be and is preferably carried out in the presence of a metal iodide. The metal iodide includes, for example, alkali metal iodides such as lithium iodide, sodium iodide, potassium iodide, and the like. Among these, potassium iodide is preferable. In this way, by carrying out Reaction (G) in the presence of the alkali metal iodide, $X^{40}$ possessed by the haloester derivative (7) is converted to an iodine atom which is easy to eliminate.

When the alkali metal iodide is used, the amount thereof used is usually preferably 0.001 to 1 mole relative to 1 mole of the haloester derivative (7), more preferably 0.005 to 0.5 mole, and even more preferably 0.01 to 0.3 mole.

Reaction (G) can be carried out in the presence or absence of a solvent. The solvent is not particularly limited as long as it does not interfere with the reaction. For example, there may be mentioned aliphatic hydrocarbons such as hexane, heptane, octane, and the like; aromatic hydrocarbons such as toluene, xylene, cymene, and the like; halogenated hydrocarbons such as dichloromethane, 1,2-dichloroethane, and the like; ethers such as tetrahydrofuran, diisopropyl ether, and the like; nitriles such as acetonitrile, benzonitrile, and the like; amides such as N,N-dimethylformamide, N-methylpyrrolidone, and the like; alcohols such as methanol, ethanol, t-butanol, and the like; esters such as ethyl acetate, butyl acetate, and the like. Among these, the amides are preferable and N,N-dimethylformamide is more preferable. The solvent may be used singly or by mixing two or more kinds. When a solvent is used, the amount thereof used is, from the viewpoint of economic efficiency and ease of after-treatment, preferably 0.1 mass times to 100 mass times based on the haloester derivative (7), and more preferably 0.1 mass times to 30 mass times.

Reaction (G) can be carried out in the presence or absence of a polymerization inhibitor. The polymerization inhibitor is not particularly limited and includes, for example, quinone compounds such as hydroquinone, methoxyphenol, benzoquinone, toluquinone, and the like; alkylphenol compounds such as p-tert-butylcatechol, 2,6-di-tert-butylphenol, 2,4-di-tert-butylphenol, 2-tert-butyl-4,6-dimethylphenol, and the like; amine compounds such as phenothiazine and the like. The polymerization inhibitor may be used singly or in combination of two or more kinds. When a polymerization inhibitor is used, the amount thereof used is preferably 0.001 mass ppm to 5 mass % relative to the mass of the whole reaction mixture, more preferably 0.001 mass ppm to 1 mass %, and even more preferably 0.001 mass ppm to 0.5 mass %.

The reaction temperature of Reaction (G) varies depending on the kinds of the haloester derivative (7), the acrylic acid (5), the base, and the solvent used, but is usually preferably −50 to 200° C., more preferably, from the viewpoint of suppression of polymerization of the acrylic acid (5) and the acrylic acid ester derivative (1-c) obtained and from the viewpoint of solubility of the raw materials, the base, and the like in a solvent, −80° C. to 150° C., even more preferably −50° C. to 150° C., and especially preferably −50 to 120° C. The reaction pressure of Reaction (G) is not particularly limited, but it is easy and preferable to carry out the reaction under ordinary pressure. The reaction time of Reaction (G) varies depending on the kinds of the haloester derivative (7), the acrylic acid (5), the base, and the solvent used, but it is usually preferably 0.5 hour to 48 hours, and more preferably 1 hour to 24 hours.

Isolation and purification of the acrylic acid ester derivative (1-c) from a reaction mixture obtained in Reaction (G) can be carried out by a method generally used in isolation and purification of an organic compound. For example, after completion of the reaction, water is added to the reaction mixture, and the mixture is separated into an organic layer and an aqueous layer. The organic layer is washed with water, and, if necessary, the aqueous layer is extracted with an organic solvent. By combining the organic layers obtained and concentrating the same, the acrylic acid ester derivative (1-c) can be isolated. And, if necessary, the acrylic acid ester derivative (1-c) of high purity can be obtained by a usual purification means such as recrystallization, distillation, silica gel column chromatography, and the like.

Specific examples of the acrylic acid ester derivative (1-c) are shown in the following, but the present invention is not particularly limited to these:

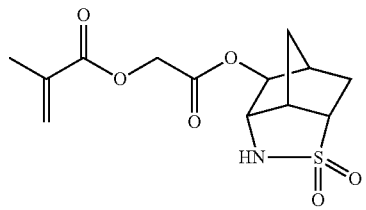

39
-continued
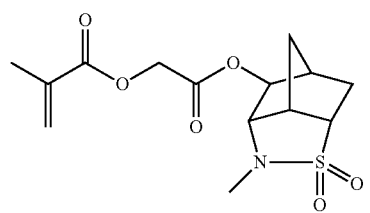
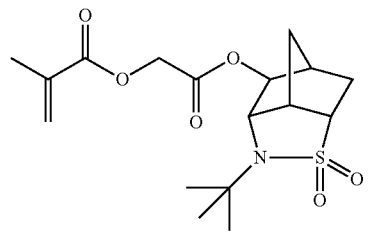
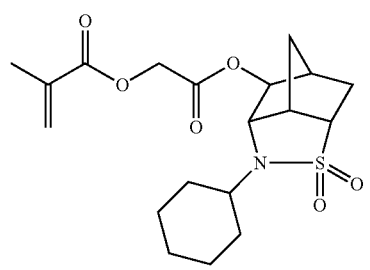
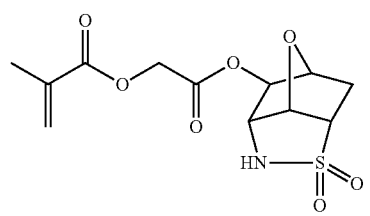
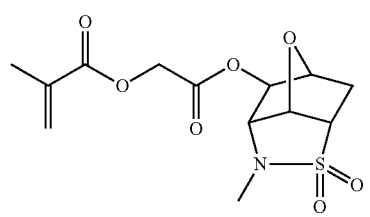
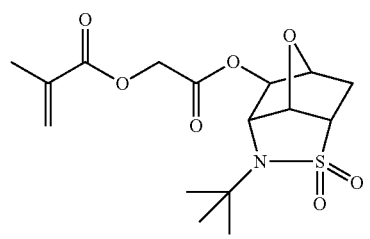
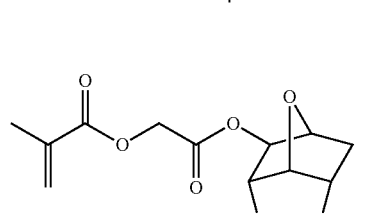
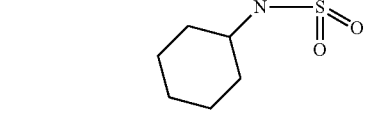
40
-continued
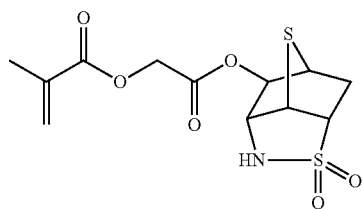
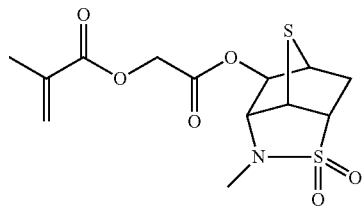
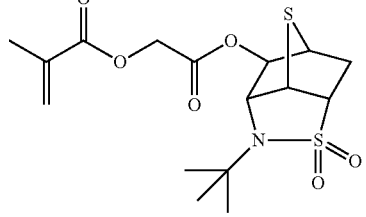
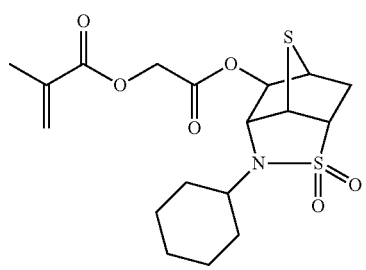
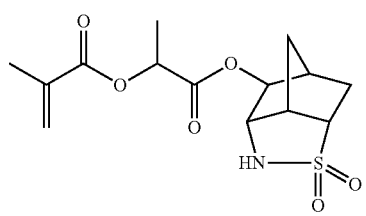
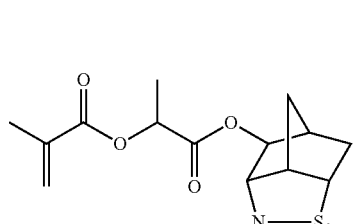
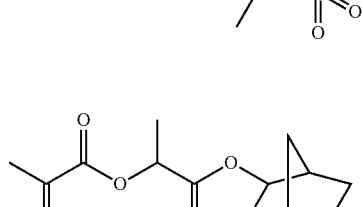
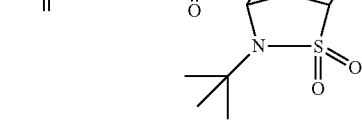

41
-continued
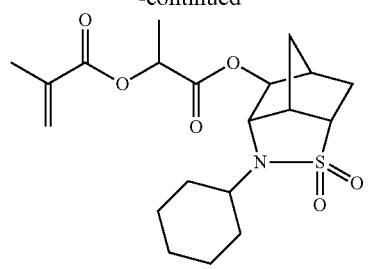
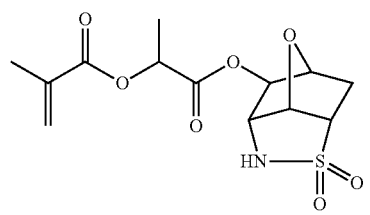
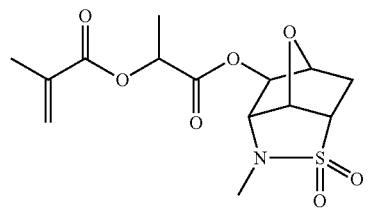
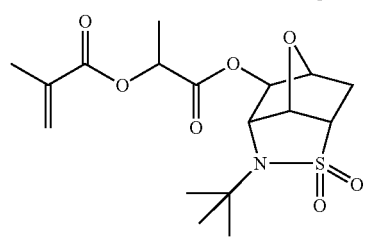
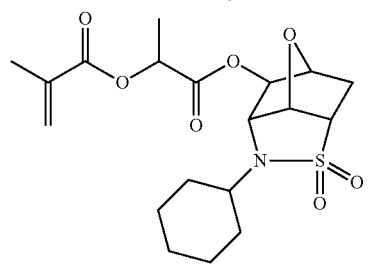
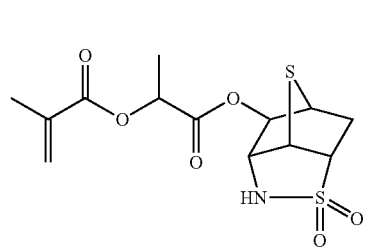
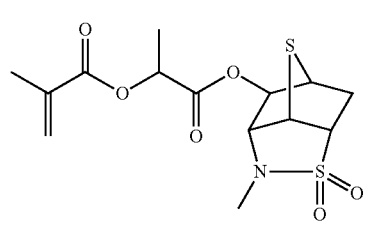
42
-continued
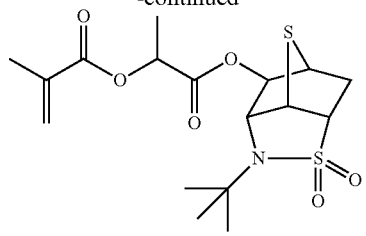
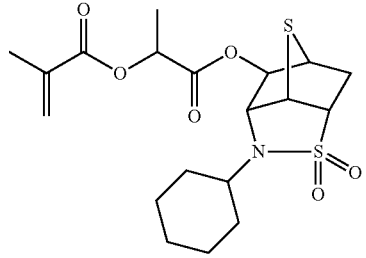
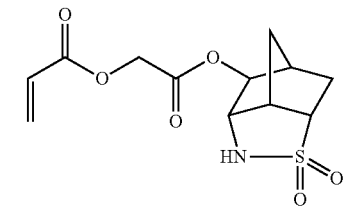
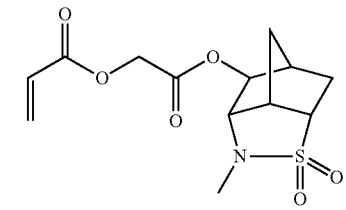
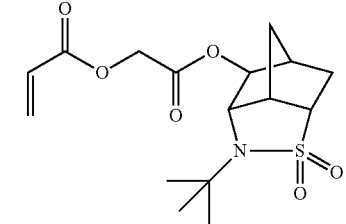
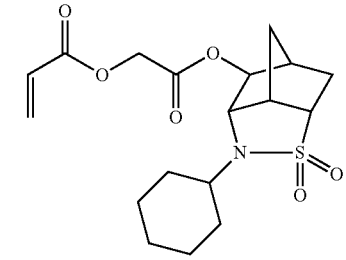
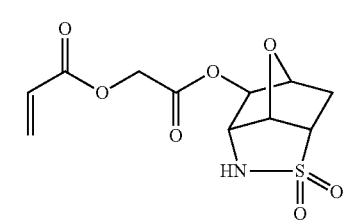

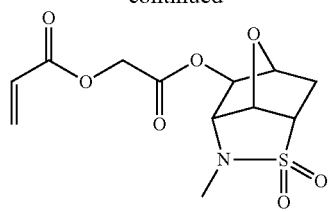
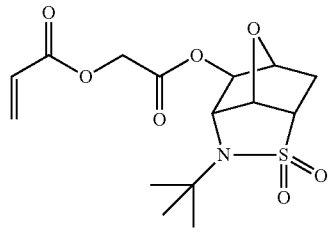
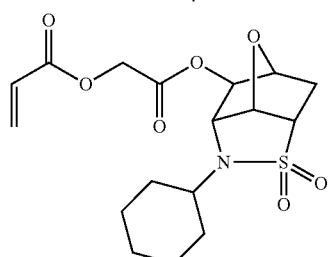
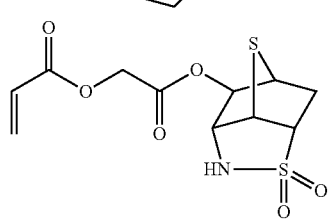
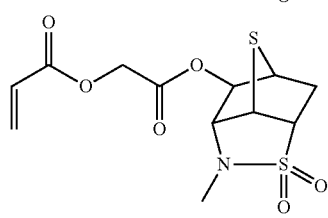
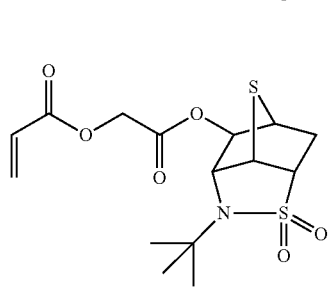
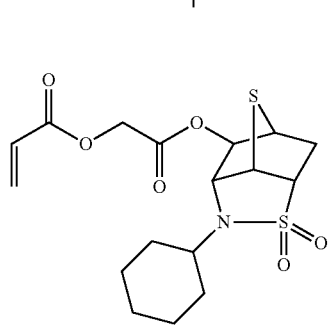
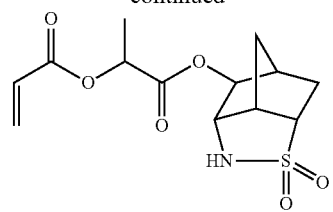
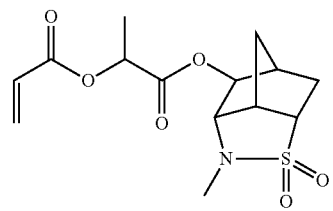
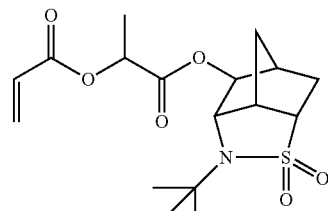
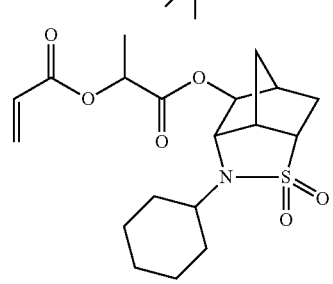
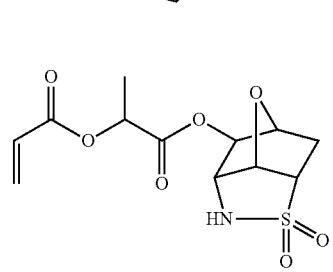

-continued

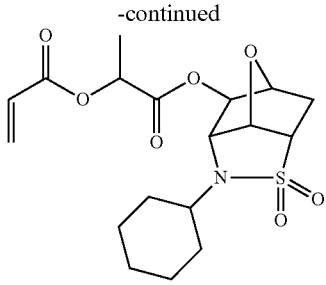

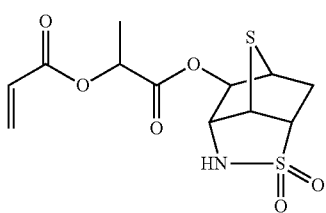

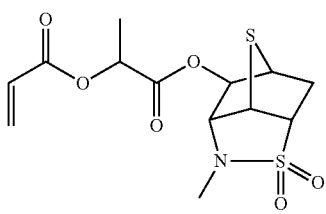

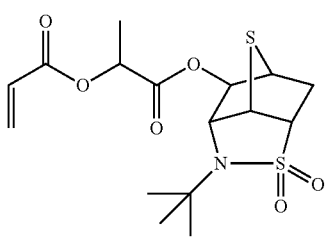

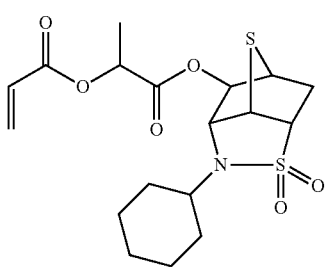

(Polymer)

A polymer containing the acrylic acid ester derivative (1) as a constituent unit, that is, a polymer obtained by polymerizing the acrylic acid ester derivative (1) singly or a copolymer obtained by polymerizing the acrylic acid ester derivative (1) and other polymerizable compounds is useful as a polymer for a photoresist composition for a semiconductor.

The polymer has a constituent unit (a0) represented by the following general formula (a0):

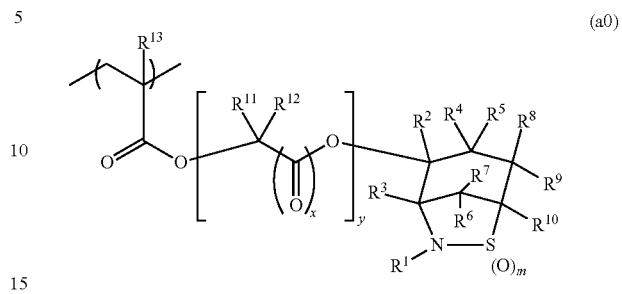

(wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, m, x, and y are as defined previously.)

Specific examples of the constituent unit (a0) are shown in the following. In each of the following formulae, $R^{13}$ represents a hydrogen atom, a methyl group, or a trifluoromethyl group as defined previously.

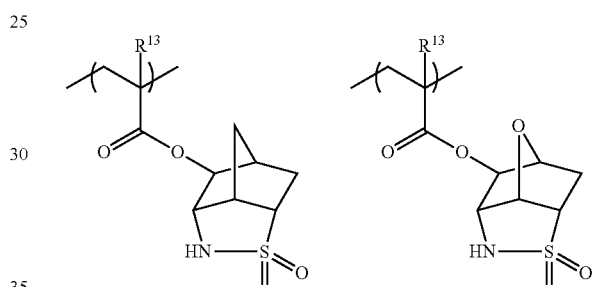

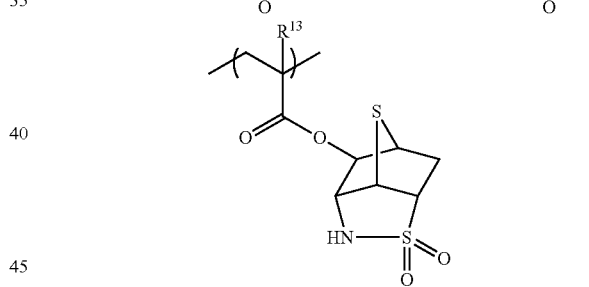

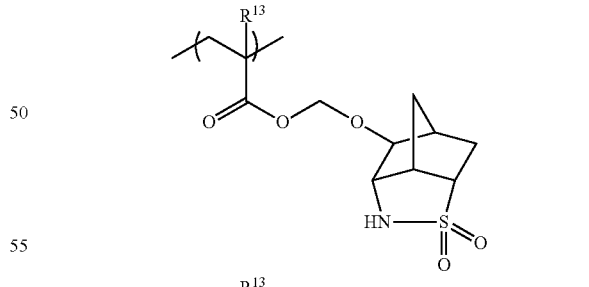

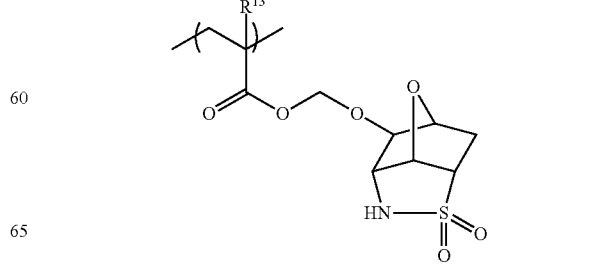

-continued
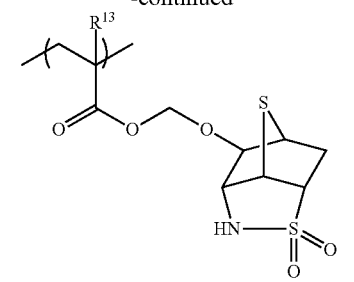
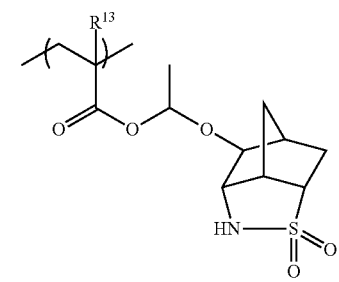
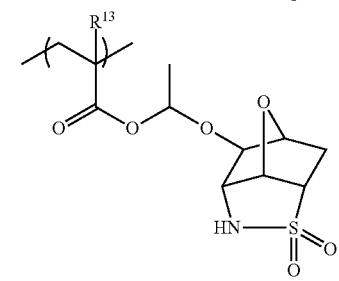
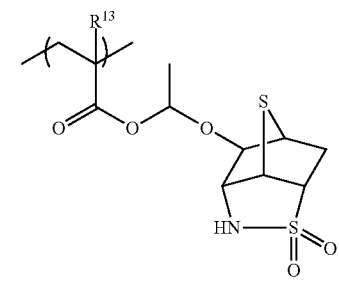
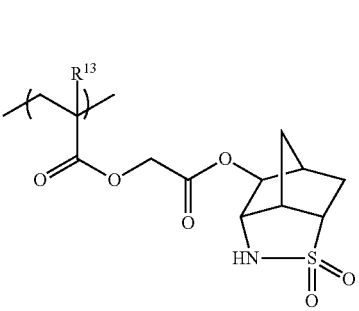
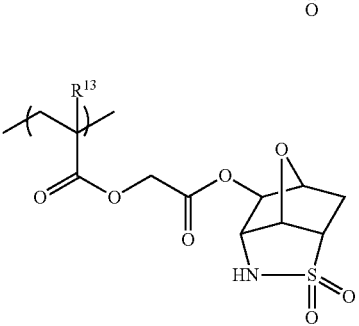
-continued
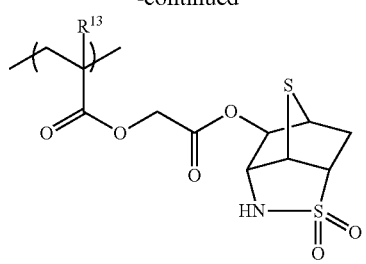
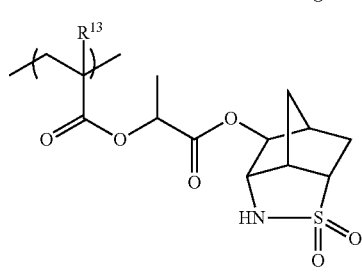
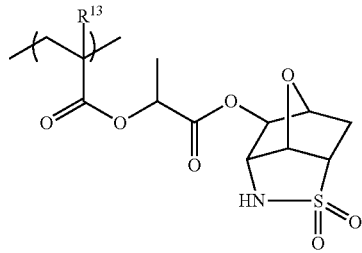
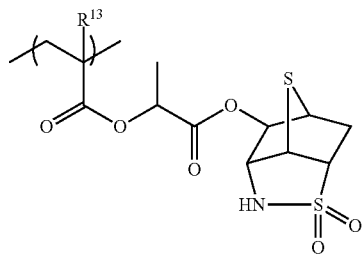
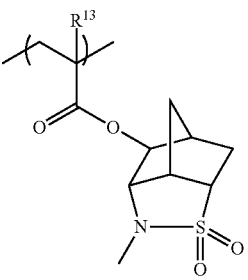 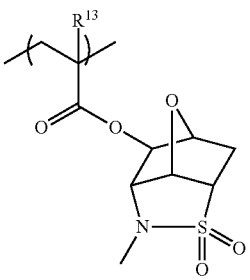

49
-continued
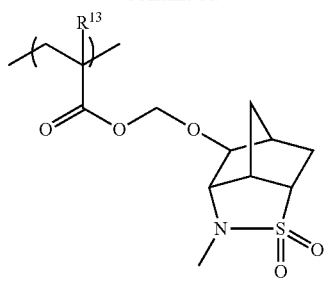
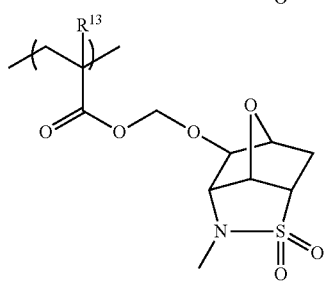
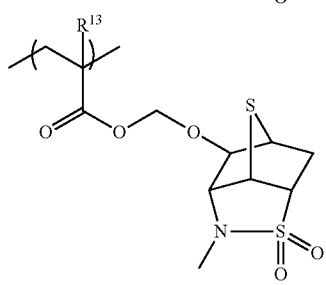
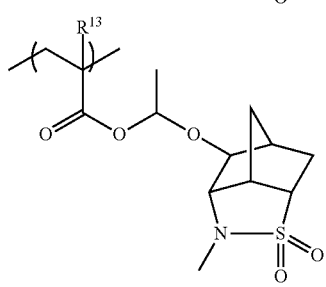
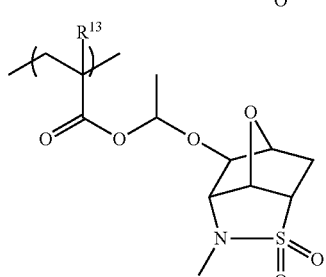
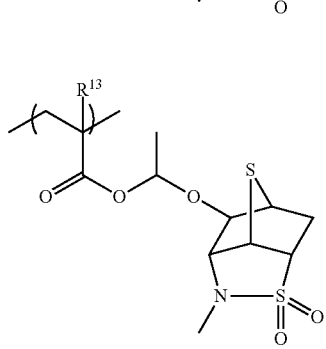
50
-continued
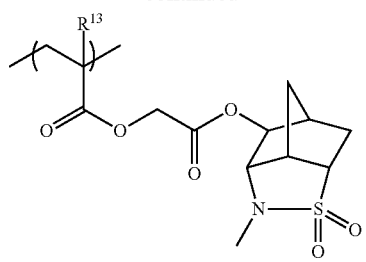
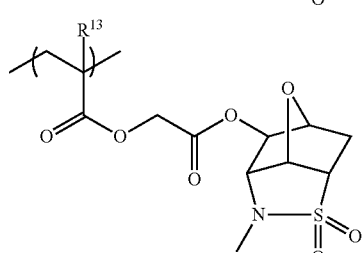
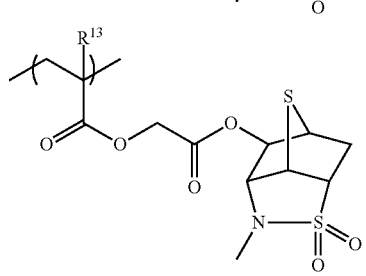
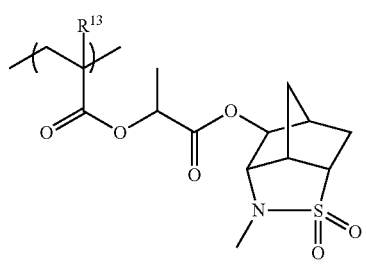
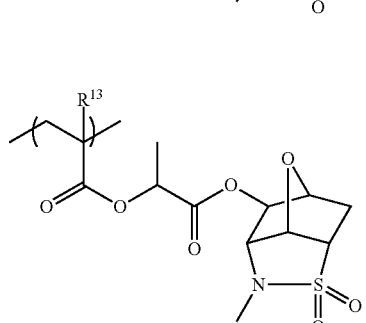
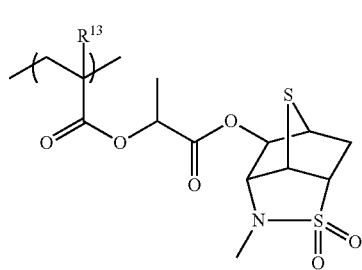

51
-continued
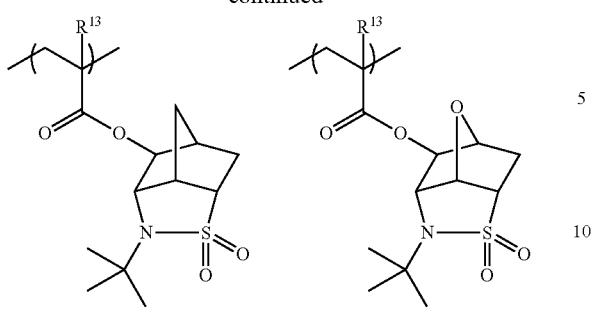
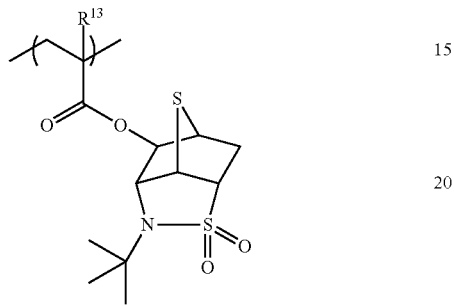
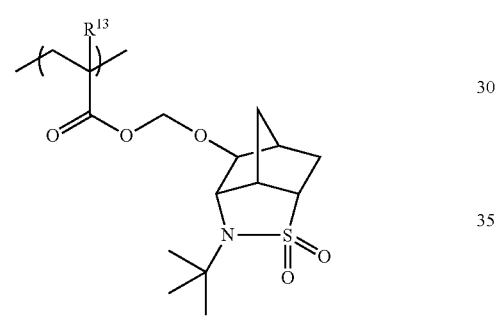
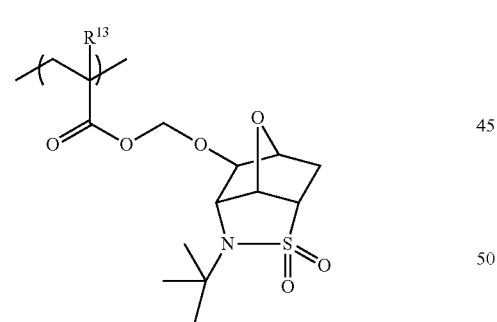
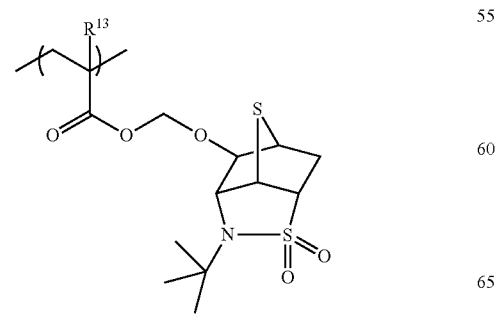
52
-continued
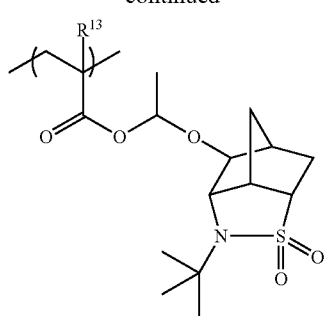
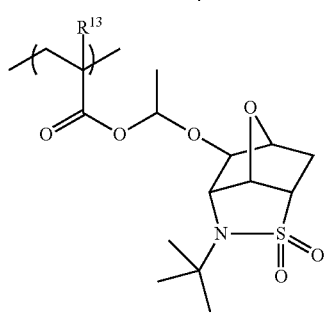
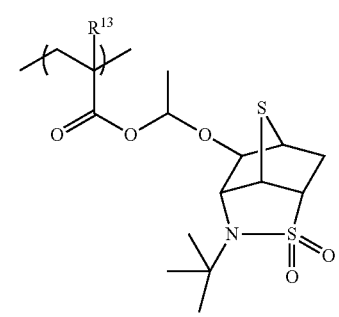
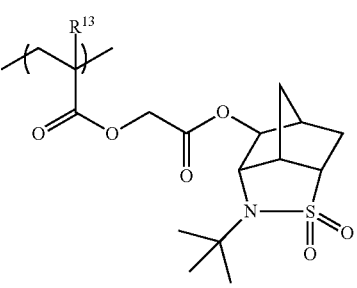
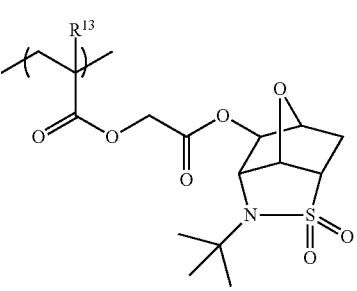

53
-continued
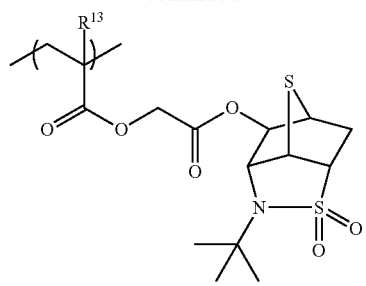
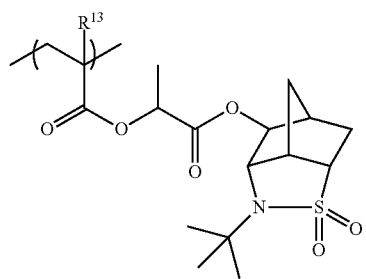
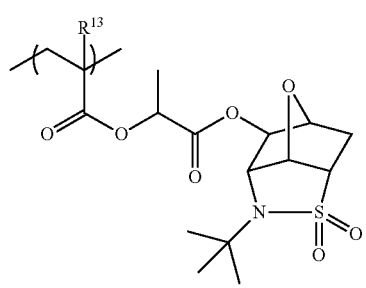
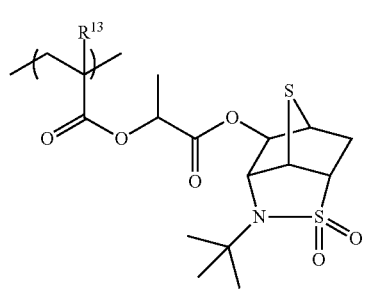
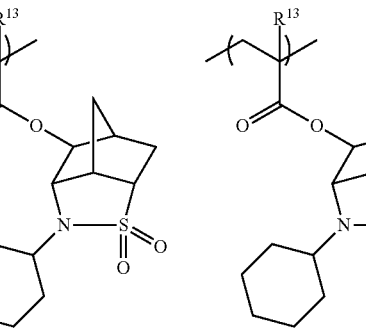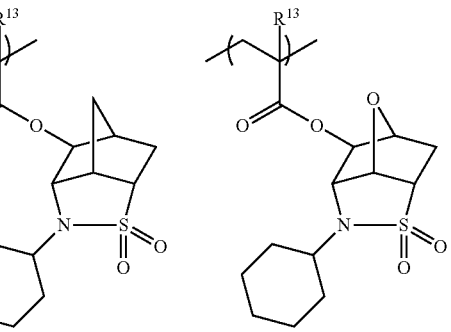
54
-continued
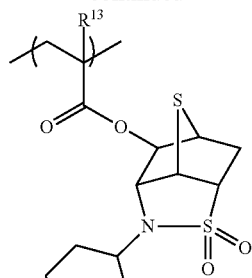
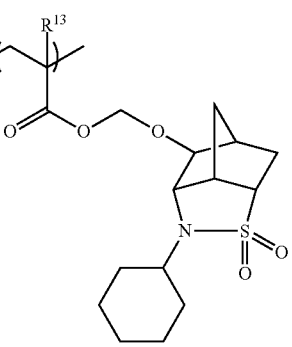
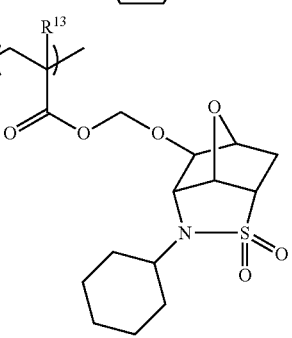
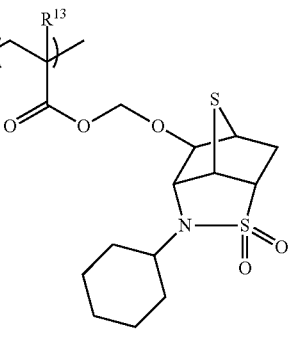
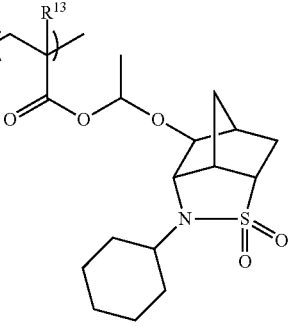

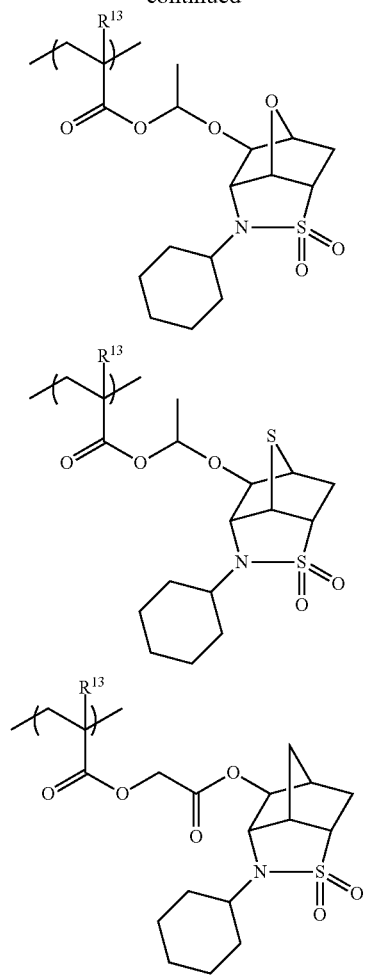

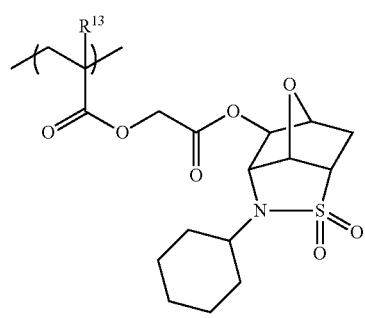

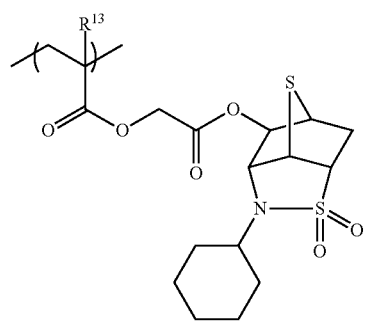

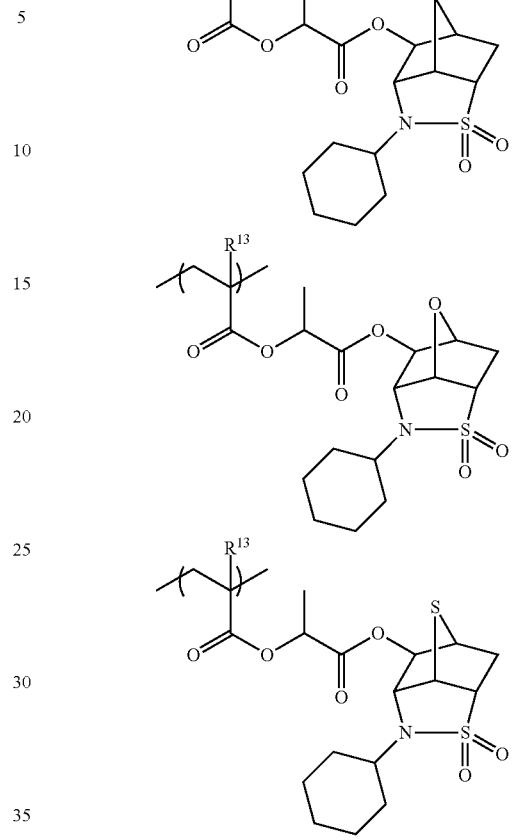

The polymer contains the constituent unit (a0) based on the acrylic acid ester derivative (1) in a range of more than 0 mole % and no more than 100 mole % and, from the viewpoint of obtaining an improvement effect of LWR and a photoresist pattern of high resolution, preferably contains the constituent unit (a0) in a range of 5 to 80 mole %, more preferably 10 to 70 mole %, and even more preferably 10 to 50 mole %.

Specific examples of other polymerizable compounds which can be copolymerized with the acrylic acid ester derivative (1) (hereinafter, referred to as the copolymerizable monomers) include, for example, compounds represented by the following chemical formulae. However, the present invention is not particularly limited to these.

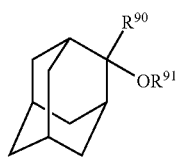

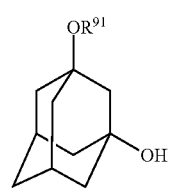

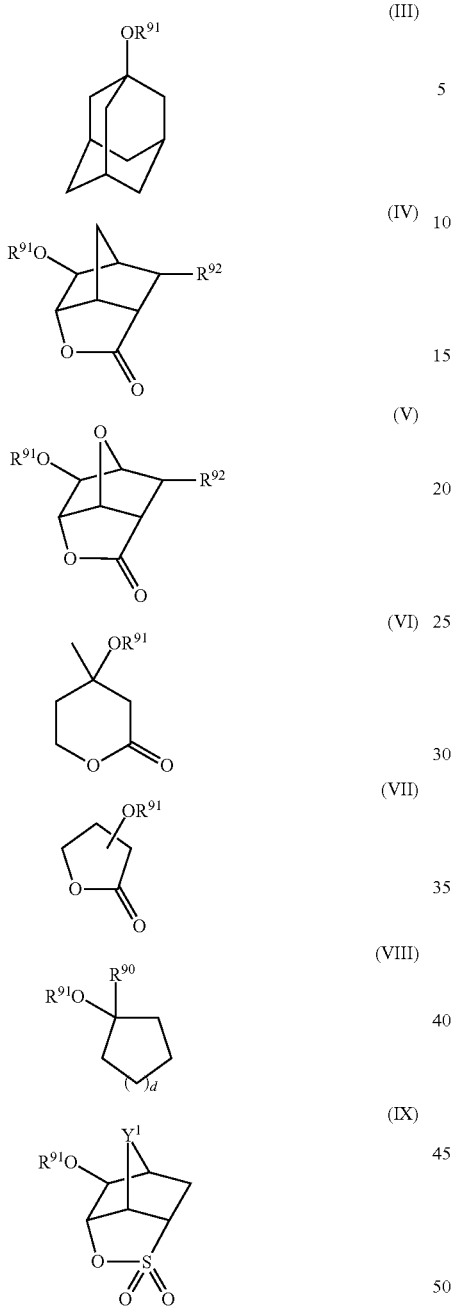

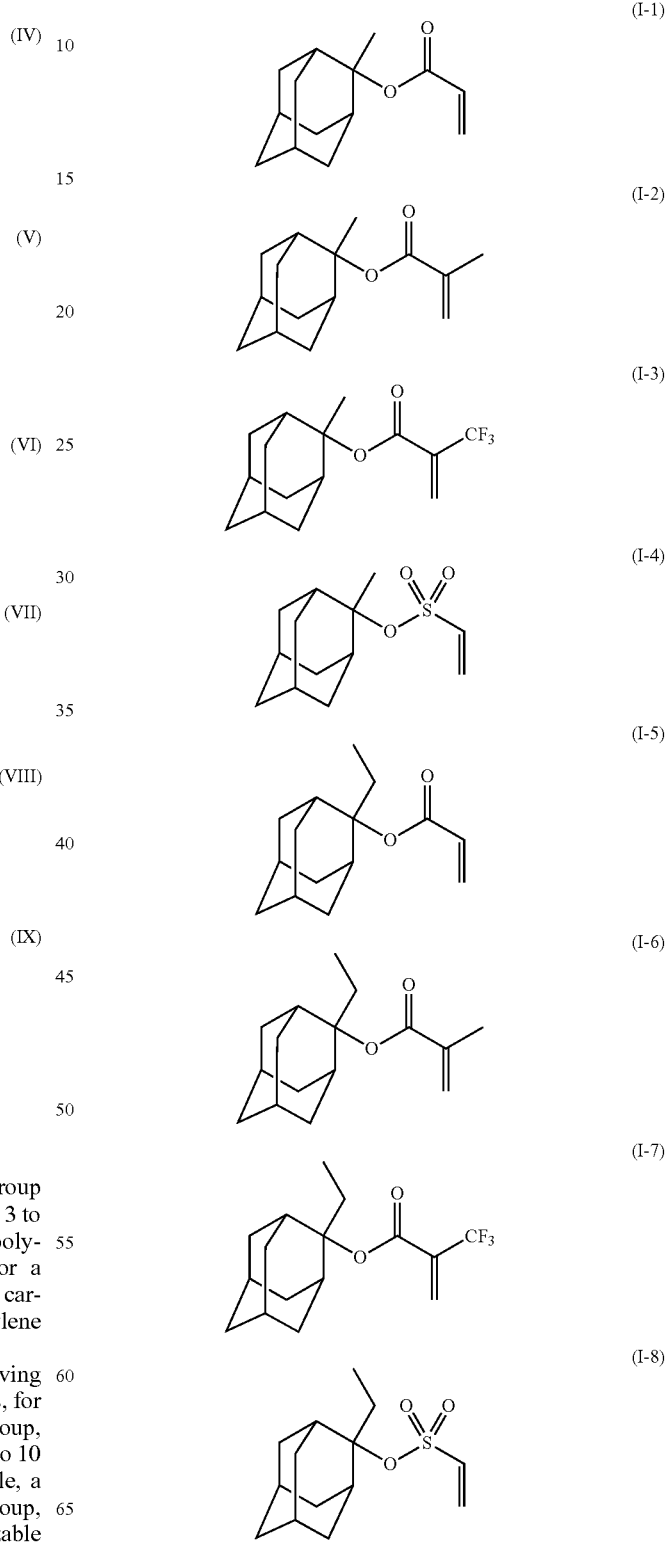

sented by $R^{91}$ includes, for example, an acryloyl group, a methacryloyl group, a vinyl group, a vinylsulfonyl group, and the like.

Specific examples of the above (I) are shown in the following. However, the present invention is not limited to these.

In the formulae (I) to (IX), $R^{90}$ represents an alkyl group having 1 to 3 carbon atoms or a cycloalkyl group having 3 to 10 carbon atoms; $R^{91}$ represents a group containing a polymerizable group; $R^{92}$ represents a hydrogen atom or a —COOR$^{93}$ (R$^{93}$ represents an alkyl group having 1 to 3 carbon atoms); $Y^1$ represents an oxygen atom or a methylene group; and d represents an integer of 1 to 5.

In the copolymerizable monomers, the alkyl group having 1 to 3 carbon atoms represented by $R^{90}$ and $R^{93}$ includes, for example, a methyl group, an ethyl group, a n-propyl group, and an isopropyl group. The cycloalkyl group having 3 to 10 carbon atoms represented by $R^{90}$ includes, for example, a cyclopentyl group, a cyclohexyl group, a cycloheptyl group, a cyclooctyl group, and the like. Further, the polymerizable group in the polymerizable group-containing group repre- (I-9)
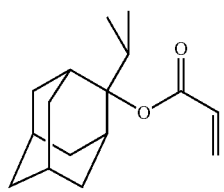
(I-10)
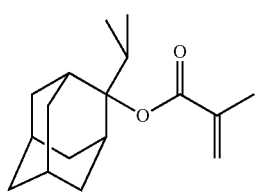
(I-11)
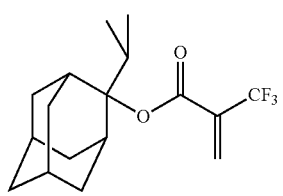
(I-12)
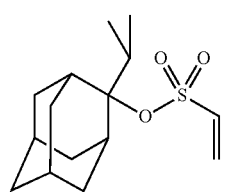
Specific examples of the above formula (II) are shown by the following chemical formulas but the present invention is not particularly limited to these.
(II-1)
(II-2)
(II-3)
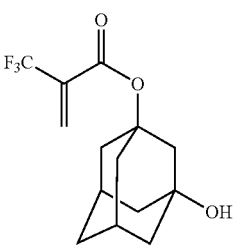
(II-4)
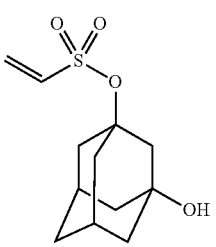
Specific examples of the above formula (III) are shown by the following chemical formulas but the present invention is not particularly limited to these.
(III-1)
(III-2)
(III-3)

(III-4)
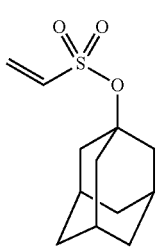
Specific examples of the above formula (IV) are shown by the following chemical formulas but the present invention is not particularly limited to these.
(IV-1)
(IV-2)
(IV-3)
(IV-4)
(IV-5)
(IV-6)
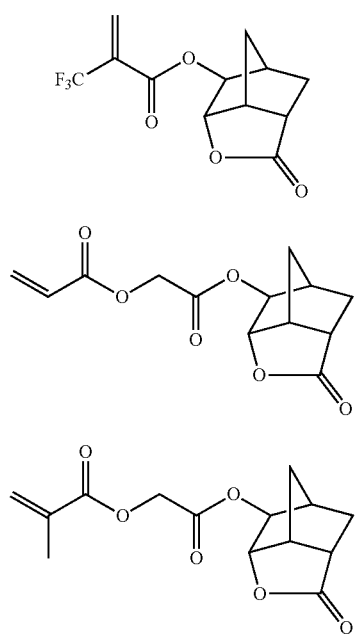
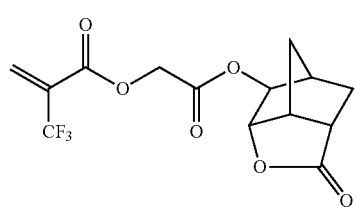
(IV-7)
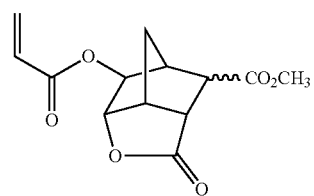
(IV-8)
(IV-9)
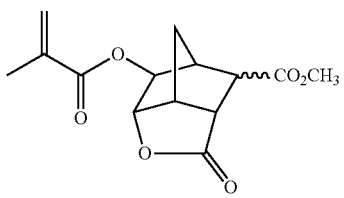
(IV-10)
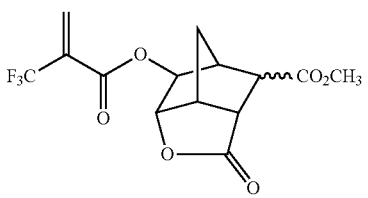
(IV-11)
(IV-12)
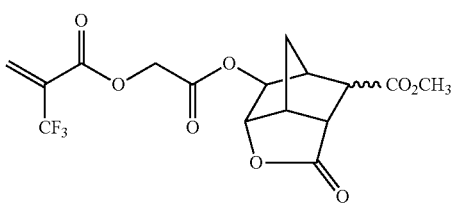
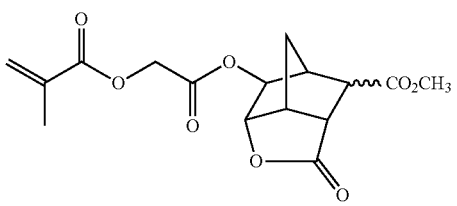
(IV-13)
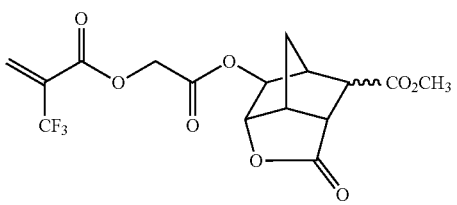
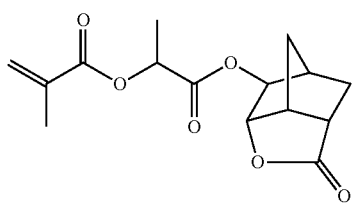

(IV-14)
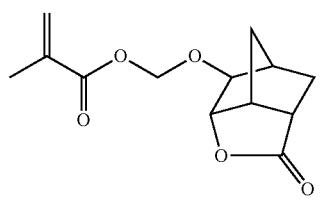
Specific examples of the above formula (V) are shown by the following chemical formulas but the present invention is not particularly limited to these.
(V-1)
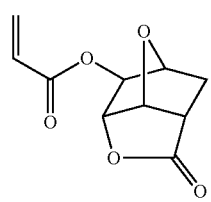
(V-2)
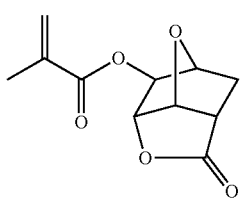
(V-3)
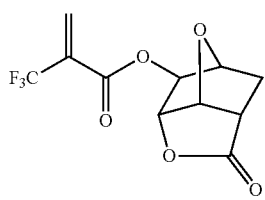
(V-4)
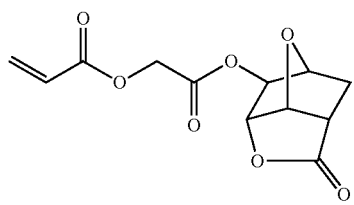
(V-5)
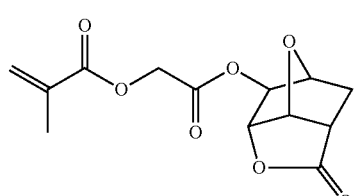
(V-6)
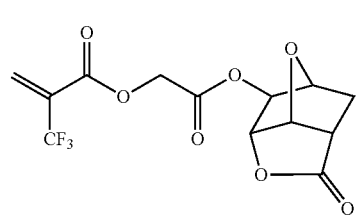
(V-7)
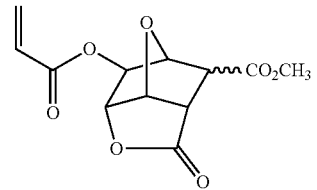
(V-8)
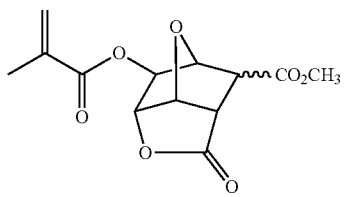
(V-9)
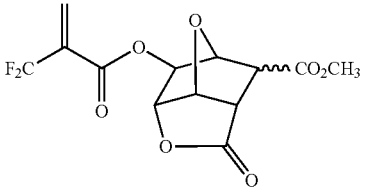
(V-10)
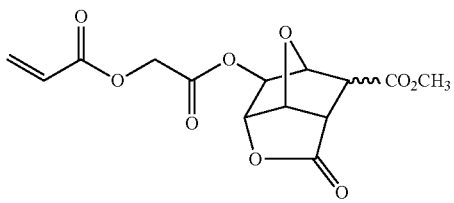
(V-11)
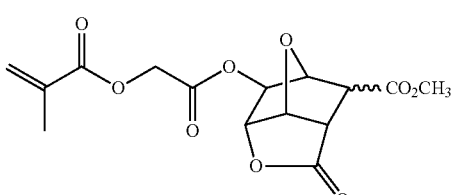
(V-12)
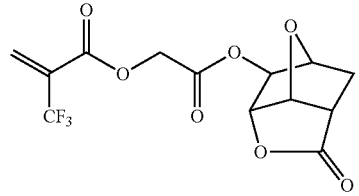
(V-13)
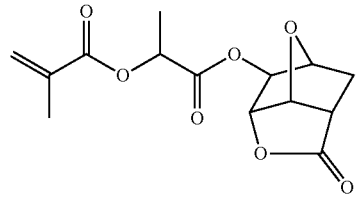

-continued (V-14)
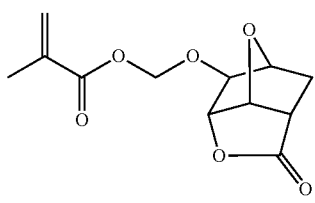

Specific examples of the above formula (VI) are shown by the following chemical formulas but the present invention is not particularly limited to these.

(VI-1)
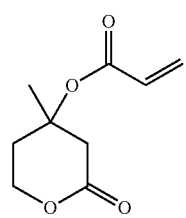

(VI-2)
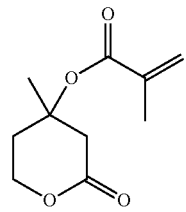

(VI-3)
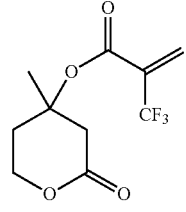

(VI-4)
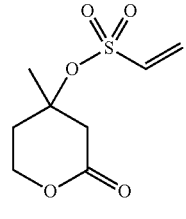

Specific examples of the above formula (VII) are shown by the following chemical formulas but the present invention is not particularly limited to these.

(VII-1)
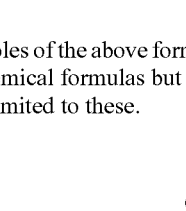

(VII-2)

(VII-3)

(VII-4)

(VII-5)

(VII-6)

(VII-7)

(VII-8)

(VII-9)

(VII-10)

(VII-11)

(VII-12)

(VII-13)

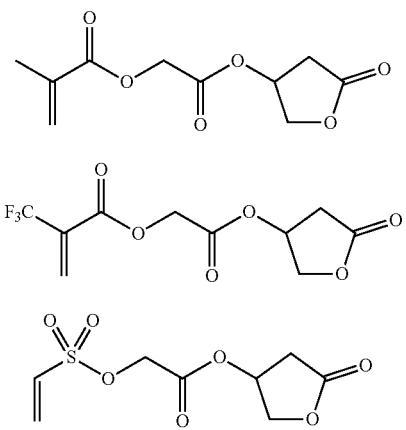
Specific examples of the above formula (VIII) are shown by the following chemical formulas but the present invention is not particularly limited to these.
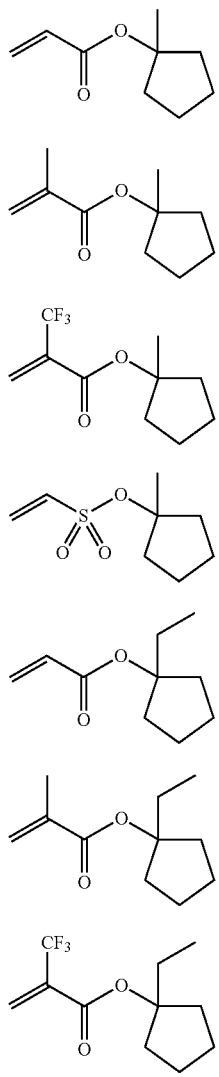

-continued
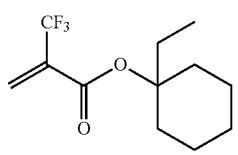
(VIII-19)
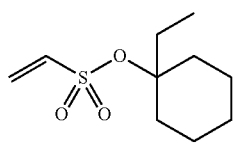
(VIII-20)
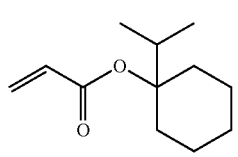
(VIII-21)
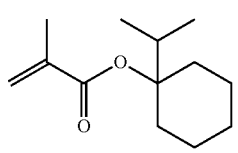
(VIII-22)
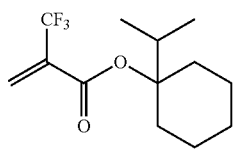
(VIII-23)
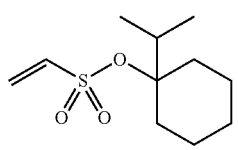
(VIII-24)
Specific examples of the above formula (IX) are shown by the following chemical formulas but the present invention is not particularly limited to these.
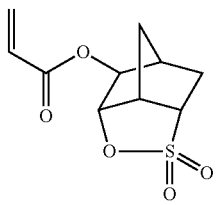
(IX-1)
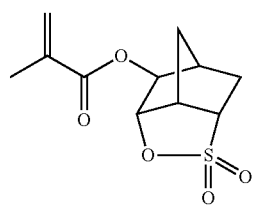
(IX-2)
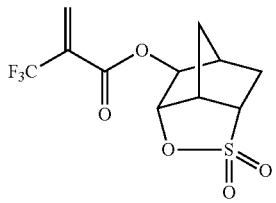
(IX-3)
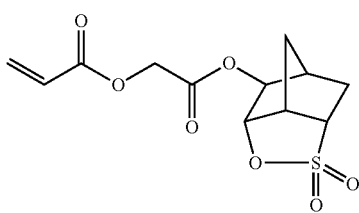
(IX-4)
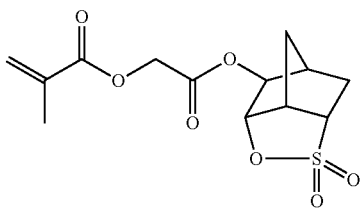
(IX-5)
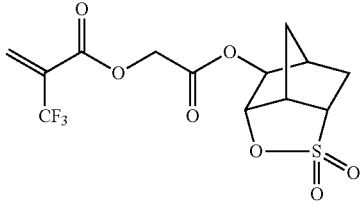
(IX-6)
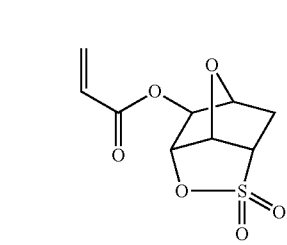
(IX-7)
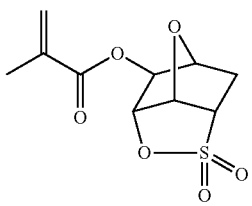
(IX-8)
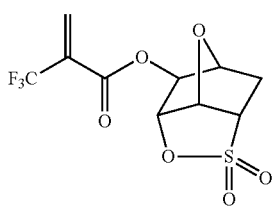
(IX-9)

(IX-10)
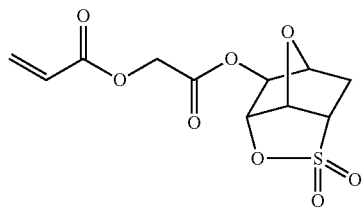

(IX-11)
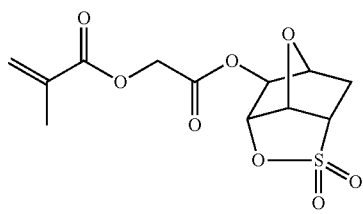

(IX-12)
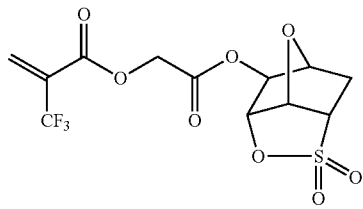

Among the above, from the viewpoint of obtaining an improvement effect of LWR and a photoresist pattern of high resolution, preferable are the copolymerizable monomers represented by the formula (I), (II), (IV), (V), and (VII), and more preferably combined use of the copolymerizable monomers represented by the formula (I) and the copolymerizable monomers represented by the formula (VII).

(Method for Producing the Polymer)

The polymer can be produced by radical polymerization according to a conventional process. Especially, as a process to synthesize a polymer having a narrow molecular weight distribution, there may be mentioned living radical polymerization and the like.

In a general polymerization process, if necessary, one or more acrylic acid ester derivatives (1) and, if necessary, one or more copolymerizable monomers mentioned above are polymerized in the presence of a radical polymerization initiator, a solvent, and, if necessary, a chain transfer agent.

There is no particular limitation for carrying out the radical polymerization is carried out and there may be employed a conventional method used in producing an acrylic resin such as a solution polymerization process, an emulsion polymerization process, a suspension polymerization process, a bulk polymerization process, and the like.

The radical polymerization initiator includes, for example, hydroperoxide compounds such as 1-butyl hydroperoxide, cumene hydroperoxide, and the like; dialkyl peroxide compounds such as di-t-butyl peroxide, t-butyl-α-cumyl peroxide, di-α-cumyl peroxide, and the like; diacyl peroxide compounds such as benzoyl peroxide, diisobutyryl peroxide, and the like; azo compounds such as 2,2'-azobisisobutyronitrile, dimethyl-2,2'-azobisisobutyrate, dimethyl azobisisobutyrate and the like; and the like.

The amount of the radical polymerization initiator used may be selected appropriately depending on the polymerization conditions such as the kind and amount of the acrylic acid ester derivative (1), the copolymerizable monomer, the chain transfer agent, the solvent, polymerization temperature, and the like. However, relative to 1 mole of the total polymerizable compounds [total amount of the acrylic acid ester derivative (1) and the copolymerizable monomer; hereinafter the same shall apply], it is usually preferably 0.005 to 0.4 mole and more preferably 0.01 to 0.3 mole.

The solvent is not particularly limited unless it interferes with the polymerization reaction and includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; esters such as ethyl lactate, methyl 3-methoxypropionate, methyl acetate, ethyl acetate, propyl acetate, and the like; ketones such as acetone, methyl ethyl ketone, methyl isopropyl ketone, methyl isobutyl ketone, methyl amyl ketone, cyclopentanone, cyclohexanone, and the like; ethers such as diethyl ether, diisopropyl ether, dibutyl ether, tetrahydrofuran, 1,4-dioxane, and the like; and the like.

The amount of the solvent used, relative to 1 part by mass of the total polymerizable compounds, is usually preferably 0.5 to 20 parts by mass and more preferably 1 to 10 parts by mass from the viewpoint of economic efficiency.

The chain transfer agent includes, for example, thiol compounds such as dodecanethiol, mercaptoethanol, mercaptopropanol, mercaptoacetic acid, mercaptopropionic acid, and the like. When the chain transfer agent is used, the amount thereof used, relative to 1 mole of the total polymerizable compounds, is usually preferably 0.005 to 0.2 mole and more preferably 0.01 to 0.15 mole.

The reaction temperature is usually preferably 40° C. to 150° C., and more preferably 40° C. to 120° C. from the viewpoint of stability of the polymer formed.

The polymerization reaction time varies depending on the polymerization conditions such as the kind and amount of the acrylic acid ester derivative (1), the copolymerizable monomer, the polymerization initiator, the chain transfer agent and the solvent; polymerization reaction temperature, and the like. However, it is usually preferably 30 minutes to 48 hours and more preferably 1 hour to 24 hours.

The polymerization reaction is preferably carried out under an atmosphere of an inert gas such as nitrogen, argon, and the like.

The thus obtained polymer may be isolated by a usual operation such as reprecipitation and the like. The isolated polymer may be dried under a vacuum condition.

The solvent used in the reprecipitation operation includes aliphatic hydrocarbons such as pentane, hexane, heptane and the like; alicyclic hydrocarbons such as cyclopentane cyclohexane and the like; aromatic hydrocarbons such as benzene, xylene, and the like; halogenated hydrocarbons such as dichloromethane, chloroform, chlorobenzene, dichlorobenzene, and the like; nitrated hydrocarbons such as nitromethane and the like; nitriles such as acetonitrile, benzonitrile, and the like; ethers such as diethyl ether, diisopropyl ether, tetrahydrofuran, 1,4-dioxane, and the like; ketones such as acetone, methyl ethyl ketone, and the like; carboxylic acids such as acetic acid and the like; esters such as ethyl acetate, butyl acetate, and the like; carbonates such as dimethyl carbonate, diethyl carbonate, ethylene carbonate, and the like; alcohols such as methanol, ethanol, propanol, isopropyl alcohol, butanol, and the like; and water. These may be used singly or in combination of two or more kinds.

The amount of the solvent used in the reprecipitation operation varies depending on the kind of polymer and the kind of solvent but, relative to 1 part by mass of the polymer, is usually preferably 0.5 to 100 parts by mass and, more preferably 1 to 50 parts by mass from the viewpoint of economic efficiency.

The weight-average molecular weight (Mw) of the polymer is not particularly limited, but it is preferably 500 to 50,000, more preferably 1,000 to 30,000, and even more preferably 5,000 to 15,000. Within this range, the polymer is highly useful as a component of a photoresist composition, which will be described later. Such a weight-average molecular weight is a standard polystyrene-equivalent value obtained by gel permeation chromatography (GPC) measurement.

Furthermore, the molecular weight distribution (Mw/Mn) of the polymer is not particularly limited, but it is preferably 1.0 to 3.0, and more preferably 1.0 to 2.0. Within this range, the polymer is highly useful as a component of a photoresist composition, which will be described later. Such a Mw and a number-average molecular weight (Mn) are standard polystyrene-equivalent values obtained by gel permeation chromatography (GPC) measurements.

(Photoresist Composition)

The photoresist composition of the present invention is prepared by mixing the polymer, a photoacid generator, and a solvent; and, if necessary, a basic compound, a surfactant, and other additives. Hereinafter, each component will be described.

(Photoacid Generator)

The photoacid generator heretofore known as photoacid generators usually used in a chemically amplified photoresist may be used without any limitation. The photoacid generators include, for example, onium salt-type photoacid generators such as iodonium salts, sulfonium salts, and the like; oxime sulfonate-type photoacid generators; bisalkyl- or bisarylsulfonyl diazomethane-type photoacid generators; nitrobenzylsulfonate-type photoacid generators; iminosulfonate-type photoacid generators; disulfone-type photoacid generators; and the like. These may be used singly or in combination of two or more kinds. Among these, preferable are the onium salt-type photoacid generators and further, from the viewpoint of strength of an acid generated, preferable are the following fluorine-containing onium salts containing fluorine-containing alkyl sulfonate ions as the anion.

Specific examples of the above-mentioned fluorine-containing onium salt include, diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate, or nonafluorobutanesulfonate; tri(4-methylphenyl)sulfonium trifluoromethanesulfonate, heptafluoropropanesulfonate, or nonafluorobutanesulfonate; dimethyl(4-hydroxylnaphthyl)sulfonium trifluoromethanesulfonate, heptafluoropropanesulfonate, or nonafluorobutanesulfonate; monophenyldimethylsulfonium trifluoromethanesulfonate, heptafluoropropanesulfonate, or nonafluorobutanesulfonate; diphenylmonomethylsulfonium trifluoromethanesulfonate, heptafluoropropanesulfonate, or nonafluorobutanesulfonate; (4-methylphenyl)diphenylsulfonium trifluoromethanesulfonate, heptafluoropropanesulfonate, or nonafluorobutanesulfonate; (4-methoxyphenyl)diphenylsulfonium trifluoromethanesulfonate, heptafluoropropanesulfonate, or nonafluorobutanesulfonate; tri(4-tert-butyl)phenylsulfonium trifluoromethanesulfonate, heptafluoropropanesulfonate, or nonafluorobutanesulfonate; and the like. These may be used singly or in combination of two or more kinds.

The amount of the photoacid generator blended relative to 100 parts by mass of the polymer is usually preferably 0.1 to 30 parts by mass and more preferably 0.5 to 10 parts by mass from the viewpoint of securing sensitivity and developing characteristics of the photoresist composition.

(Solvent)

The solvent mixed into the photoresist composition includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; esters such as ethyl lactate, methyl 3-methoxypropionate, methyl acetate, ethyl acetate, propyl acetate, and the like; ketones such as acetone, methyl ethyl ketone, methyl isopropyl ketone, methyl isobutyl ketone, methyl amyl ketone, cyclopentanone, cyclohexanone, and the like; ethers such as diethyl ether, diisopropyl ether, dibutyl ether, tetrahydrofuran, 1,4-dioxane, and the like; and the like. These may be used singly or in a combination of two or more kinds.

The amount of the solvent mixed, relative to 1 part by mass of the polymer, is usually preferably 1 to 50 parts by mass and more preferably 2 to 25 parts by mass.

(Basic Compound)

In order to control the diffusion rate of an acid in a photoresist film and thereby to improve resolution, a basic compound is added optionally into the photoresist composition in an amount which does not interfere with characteristics thereof. Such a basic compound includes, for example, amides such as formamide, N-methylformamide, N,N-dimethylformamide, acetamide, N-methylacetamide, N,N-dimethylacetamide, N-(1-adamantyl)acetamide, benzamide, N-acetyl ethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, diacetoneacrylamide, and the like; and amines such as pyridine, 2-methypyridine, 4-methylpyridine, nicotine, quinoline, acridine, imidazole, 4-methylimidazole, benzimidazole, pyrazine, pyrazole, pyrrolidine, N-t-butoxycarbonyl pyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine, and the like. These may be used singly or in combination of two or more kinds.

When a basic compound is added, the amount thereof blended varies depending on the kind of the basic compound used but, relative to 1 mole of the photoacid generator, is usually preferably 0.01 to 10 moles and more preferably 0.05 to 1 mole.

(Surfactant)

In order to improve coating properties, if desired, a surfactant may further be mixed into the photoresist composition in a range of the amount which does not interfere with the characteristics of the photoresist composition.

Such a surfactant includes, for example, polyoxyethylene lauryl ether, polyoxyethylene stearyl ether, polyoxyethylene oleyl ether, polyoxyethylene n-octylphenyl ether, and the like. These may be used singly or in a combination of two or more kind. When a surfactant is added, the amount thereof blended relative to 100 parts by mass of the polymer is usually preferably 2 parts by mass or less.

(Other Additives)

Furthermore, into the photoresist composition, there may be mixed as other additives a sensitizer, an anti-halation agent, a shape-improving agent, a storage stabilizer, an antifoaming agent, and the like in a range of the amount which does not interfere with the characteristics of the photoresist composition.

(Method for Forming Photoresist Pattern)

A predetermined photoresist pattern may be formed by performing a series of operations of coating a photoresist composition on a substrate, prebaking the photoresist film usually preferably at 70° C. to 160° C. for 1 to 10 minutes, irradiating (exposing) the photoresist film through a predetermined mask, forming a latent pattern by post-exposure baking of the photoresist film preferably at 70° C. to 160° C. for 1 to 5 minutes, and developing the photoresist film using a developer.

To expose the photoresist film, there may be used radiation of various wavelength ranges, for example, ultraviolet light, X-rays, and the like. For semiconductor photoresist, there are usually used g-line, i-line, and excimer lasers such as XeCl, KrF, KrCl, ArF, ArCl, and the like. Among these, it is preferable to use an ArF excimer laser from the viewpoint of microfabrication.

The exposure amount is preferably 0.1 to 1,000 mJ/cm² and more preferably 1 to 500 mJ/cm².

The developer includes basic aqueous solutions prepared by dissolving inorganic bases such as sodium hydroxide, potassium hydroxide, sodium carbonate, aqueous ammonia, and the like; alkylamines such as ethylamine, diethylamine, triethylamine, and the like; alcohol amines such as dimethylethanolamine, triethanolamine, and the like; quaternary ammonium salts such as tetramethylammonium hydroxide, tetraethylammonium hydroxide, and the like; and the like. Among these, it is preferable to use alkaline aqueous solutions prepared by dissolving quaternary ammonium salts such as tetramethylammonium hydroxide, tetraethylammonium hydroxide, and the like.

The concentration of the developer is usually preferably 0.1 to 20 mass % and more preferably 0.1 to 10 mass %.

EXAMPLES

Hereinafter, the present invention will be described specifically with reference to Examples, but the present invention is not limited by these Examples.

Reference Example 1

Synthesis of 5,6-epoxy-2-norbornanesulfonamide

To a four-necked flask having an inner volume of 500 ml and equipped with an electromagnetic stirring device, a nitrogen inlet tube, and a thermometer, there were charged 10.0 g (57.7 mmol) of 5-norbornene-2-sulfonamide, 15.1 g (180.0 mmol) of sodium bicarbonate, and 200 g of dichloromethane. After cooling the mixture to 5° C., 14.8 g (60.0 mmol) of 70% m-chloroperbenzoic acid was added thereto over a 20 minute period, and the mixture was stirred at 5° C. for 2 hours. To the reaction mixture was added 100 g of distilled water, and the mixture was separated into an organic layer and an aqueous layer. The organic layer was washed with 40 g of distilled water and concentrated under reduced pressure. By recrystallizing the residue obtained from ethyl acetate, there was obtained 6.89 g (36.4 mmol) of 5,6-epoxy-2-norbornanesulfonamide represented by the following formula (yield 63%):

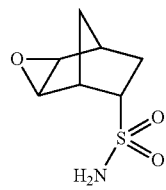

$^1$H NMR (400 MH$_z$, methanol-d$_4$, TMS, ppm) δ: 0.85-0.93 (m, 1H), 1.45-1.53 (m, 1H), 1.62-1.69 (m, 1H), 1.97-2.04 (m, 1H), 2.60-2.64 (m, 1H), 2.87-2.92 (m, 1H), 3.23-3.27 (m, 1H), 3.53-3.60 (m, 2H)

Example 1

Synthesis of 9-hydroxy-4-thia-5-azatricyclo [4.2.1.0$^{6,7}$]nonane-4,4-dioxide (Reaction (A))

To a four-necked flask having an inner volume of 5 L and equipped with an electromagnetic stirring device, a reflux condenser, a nitrogen inlet tube, and a thermometer, there were charged 230.0 g (1.22 mol) of 5,6-epoxy 2-norbornanesulfonamide obtained by the method of Reference Example 1 and 1860 g of tetrahydrofuran (THF), followed by the addition of 46.2 g (0.24 mol) of p-toluenesulfonic acid monohydrate, and the mixture was stirred at 50° C. for 7 hours. After cooling the reaction mixture to 10° C., 217 g of a 5% aqueous solution of sodium bicarbonate was added, and the reaction mixture was concentrated under reduced pressure. To the residue were added 307 g of distilled water and 608 g of ethyl acetate, and the mixture was separated into an organic layer and an aqueous layer. After washing with 100 g of distilled water, the organic layer was concentrated under reduced pressure. By recrystallizing the residue obtained from ethyl acetate, there was obtained 76.4 g (0.40 mol) of 9-hydroxy-4-thia-5-azatricyclo[4.2.1.0$^{6,7}$]nonane-4,4-dioxide represented by the following formula (yield: 33%):

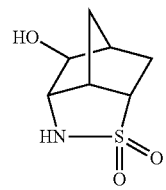

$^1$H-NMR (400 MH$_z$, methanol-d$_4$, TMS, ppm) δ: 1.63-1.66 (m, 1H), 1.80-1.84 (m, 1H), 2.00-2.05 (m, 1H), 2.08-2.11 (m, 1H), 2.29-2.30 (m, 1H), 3.22-3.26 (m, 2H), 3.30-3.31 (m, 1H), 3.31-3.37 (m, 1H), 3.56 (s, 1H).

Example 2

Synthesis of 9-hydroxy-4-thia-5-azatricyclo [4.2.1.0$^{6,7}$]nonane-4,4-dioxide (Reaction (B))

To a four-necked flask having an inner volume of 200 ml and equipped with an electromagnetic stirring device, a reflux condenser, a nitrogen inlet tube, and a thermometer, there were charged 4.0 g (20.9 mmol) of 5,6-epoxy-2-norbornanesulfonamide obtained by the method of Reference Example 1 and 100 g of t-butanol, followed by the addition of 8.2 g (73.2 mmol) of potassium t-butoxide, and the mixture was stirred at 50° C. for 8 hours. After cooling the reaction mixture to 10°

C., 10 g of distilled water and 8.9 g of concentrated hydrochloric acid were added thereto to adjust its pH to 7, and the reaction mixture was concentrated under reduced pressure. To the residue was added 100 g of ethyl acetate to separate the mixture into an organic layer and an aqueous layer, and the organic layer was concentrated under reduced pressure. The residue obtained was recrystallized from ethyl acetate to obtain 1.6 g (8.4 mmol) of 9-hydroxy-4-thia-5-azatricyclo[4.2.1.0$^{6.7}$]nonane-4,4-dioxide (yield: 40%).

Example 3

Synthesis of 9-methacryloyloxy-4-thia-5-azatricyclo[4.2.1.0$^{6.7}$]nonane-4,4-dioxide (Reaction (C))

To a four-necked flask having an inner volume of 200 ml and equipped with an electromagnetic stirring device, a reflux condenser, a nitrogen inlet tube, and a thermometer, there were charged 3.0 g (15.9 mmol) of 9-hydroxy-4-thia-5-azatricyclo[4.2.1.0$^{6.7}$]nonane-4,4-dioxide, 1.9 g (19.1 mmol) of triethylamine, and 30 g of THF. The mixture was cooled to 5° C., 1.8 g (17.5 mmol) of chloride methacrylate was added dropwise thereto over a 30-minute period, and the mixture was stirred at 5° C. for 1 hour. To the reaction mixture was added 30 g of distilled water, the mixture was separated into an organic layer and an aqueous layer, and the aqueous layer was extracted with 30 g of ethyl acetate. The organic layer obtained was washed with 15 g of distilled water and was concentrated under reduced pressure. The residue obtained was purified by silica gel column chromatography to obtain 1.2 g (4.7 mmol) of 9-methacryloyloxy-4-thia-5-azatricyclo[4.2.1.0$^{6.7}$]nonane-4,4-dioxide represented by the following formula (yield: 30%):

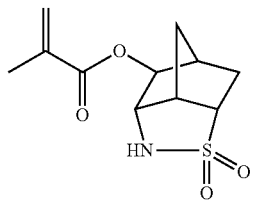 [SMILES: C=C(C)C(=O)OC1C2CC3C1NS(=O)(=O)C3C2]

$^1$H-NMR (400 MH$_Z$, CDCl$_3$, TMS, ppm) δ: 1.75 (1H, m), 1.94 (3H, s), 2.07-2.15 (3H, m), 2.58 (1H, m), 3.33 (1H, m), 3.39 (1H, m), 3.55 (1H, m), 4.44 (1H, s), 4.83 (1H, m), 5.62 (1H, m), 6.12 (1H, m).

Example 4

Synthesis of 9-chloromethoxy-4-thia-5-azatricyclo[4.2.1.0$^{6.7}$]nonane-4,4-dioxide (Reaction (D))

To a four-necked flask having an inner volume of 200 ml and equipped with an electromagnetic stirring device, a reflux condenser, a nitrogen inlet tube, and a thermometer, there were charged 3.0 g (15.9 mmol) of 9-hydroxy-4-thia-5-azatricyclo[4.2.1.0$^{6.7}$]nonane-4,4-dioxide, 100 g of dichloromethane, and 0.5 g of paraformaldehyde, and into the mixture was bubbled a hydrochloric acid gas at 20° C. for 1 hour. The reaction mixture was separated into an organic layer and an aqueous layer to obtain a dichloromethane solution of 98.2 g (11.1 mmol) of 9-chloromethoxy-4-thia-5-azatricyclo[4.2.1.0$^{6.7}$]nonane-4,4-dioxide represented by the following formula (yield: 70%):

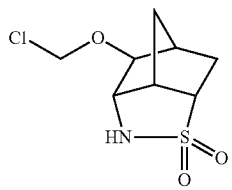 [SMILES: O=S1(=O)NC2C3CC(CC31)C2OCCl]

$^1$H-NMR (400 MH$_Z$, CDCl$_3$, TMS, ppm) δ: 1.71 (1H, m), 2.04-2.13 (3H, m), 2.55 (1H, m), 3.29 (1H, m), 3.38 (1H, m), 3.51 (1H, m), 4.47 (1H, s), 4.81 (1H, m), 5.55 (2H, m).

Example 5

Synthesis of 9-methacryloyloxymethoxy-4-thia-5-azatricyclo[4.2.1.0$^{6.7}$]nonane-4,4-dioxide (Reaction (E))

To a four-necked flask having an inner volume of 200 ml and equipped with an electromagnetic stirring device, a reflux condenser, a nitrogen inlet tube, and a thermometer, there were charged 98.2 g (11.1 mmol) of a dichloromethane solution of 9-chloromethoxy-4-thia-5-azatricyclo[4.2.1.0$^{6.7}$]nonane-4,4-dioxide obtained by the method of Example 4 and 1.1 g (13.3 mmol) of methacrylic acid. The mixture was cooled to 5° C., and thereto was added dropwise 2.2 g (22.0 mmol) of triethylamine over a 1-hour period. After the dropwise addition was complete, 30 g of distilled water was added to the reaction mixture, and the mixture was separated into an organic layer and an aqueous layer. After washing with 30 g of distilled water, the organic layer was concentrated under reduced pressure. The residue obtained was purified by silica gel column chromatography to obtain 2.4 g (8.3 mmol) of 9-methacryloyloxymethoxy-4-thia-5-azatricyclo[4.2.1.0$^{6.7}$]nonane-4,4-dioxide represented by the following formula (yield: 75%):

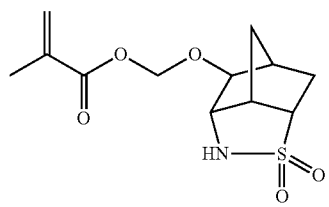 [SMILES: C=C(C)C(=O)OCOC1C2CC3C1NS(=O)(=O)C3C2]

$^1$H-NMR (400 MHz, CDCl$_3$, TMS, ppm) δ: 1.72 (1H, m), 1.94 (3H, s), 2.07-2.17 (3H, m), 2.55 (1H, m), 3.34 (1H, m), 3.37 (1H, m), 3.58 (1H, m), 4.42 (1H, s), 4.83 (1H, m), 5.41 (2H, m), 5.74 (1H, m), 6.22 (1H, m).

Example 6

Synthesis of 9-chloroacetoxy-4-thia-5-azatricyclo[4.2.1.0$^{6.7}$]nonane-4,4-dioxide (Reaction (F))

To a four-necked flask having an inner volume of 200 ml and equipped with an electromagnetic stirring device, a reflux condenser, a nitrogen inlet tube, and a thermometer, there were charged 3.0 g (15.9 mmol) of 9-hydroxy-4-thia-5-azatricyclo[4.2.1.0$^{6.7}$]nonane-4,4-dioxide, 50 g of THF, and 1.8 g (22.2 mmol) of pyridine, and the mixture was cooled to 5° C. Thereto was added dropwise 2.2 g (19.1 mmol) of chloroacetyl chloride over a 30-minute period, and the mixture was stirred at 5° C. for 30 minutes. To the reaction mixture was added 50 g of distilled water, the mixture was separated into an organic layer and an aqueous layer, and the aqueous layer was extracted with 50 g of ethyl acetate. The organic layer obtained was washed with 30 g of distilled water and was concentrated under reduced pressure. The residue obtained was recrystallized from ethyl acetate to obtain 1.7 g (6.3 mmol) of 9-chloroacetoxy-4-thia-5-azatricyclo[4.2.1.0$^{6.7}$]nonane-4,4-dioxide represented by the following formula (yield: 40%):

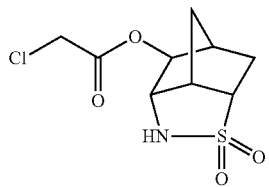 [SMILES: O=C(CCl)OC1C2CC3C1NS(=O)(=O)C3C2]

$^1$H-NMR (400 MH$_Z$, CDCl$_3$, TMS, ppm) δ: 1.72 (1H, m), 2.06-2.14 (3H, m), 2.57 (1H, m), 3.30 (1H, m), 3.36 (1H, m), 3.52 (1H, m), 4.44 (1H, s), 4.75 (2H, m), 4.84 (1H, m).

Example 7

Synthesis of 9-methacryloyloxyacetoxy-4-thia-5-azatricyclo[4.2.1.0$^{6.7}$]nonane-4,4-dioxide (Reaction (G))

To a four-necked flask having an inner volume of 200 ml and equipped with an electromagnetic stirring device, a reflux condenser, a nitrogen inlet tube, and a thermometer, there were charged 2.0 g (7.5 mmol) of 9-chloroacetoxy-4-thia-5-azatricyclo[4.2.1.0$^{6.7}$]nonane-4,4-dioxide obtained by the method of Example 6, 40 g of N,N-dimethylformamide (DMF), 0.8 g (6.0 mmol) of potassium carbonate, and 1.3 g (0.8 mmol) of potassium iodide, followed by the addition of 0.8 g (9.0 mmol) of methacrylic acid at 20° C., and the mixture was stirred at 20° C. for 4 hours. To the reaction mixture were added 30 g of distilled water and 40 g of ethyl acetate, and the mixture was separated into an organic layer and an aqueous layer. After washing with 10 g of distilled water three times, the organic layer was concentrated under reduced pressure. The residue obtained was purified by silica gel column chromatography to obtain 2.2 g (7.1 mmol) of 9-methacryloyloxyacetoxy-4-thia-5-azatricyclo[4.2.1.0$^{6.7}$]nonane-4,4-dioxide represented by the following formula (yield: 95%):

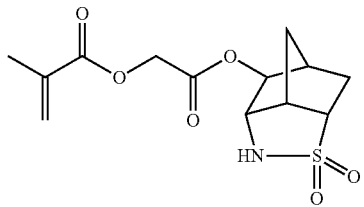 [SMILES: C=C(C)C(=O)OCC(=O)OC1C2CC3C1NS(=O)(=O)C3C2]

$^1$H-NMR (400 MH$_Z$, CDCl$_3$, TMS, ppm) δ: 1.72 (1H, m), 1.93 (3H, s), 2.07-2.15 (3H, m), 2.60 (1H, m), 3.34 (1H, m), 3.37 (1H, m), 3.55 (1H, m), 4.42 (1H, s), 4.60 (2H, s), 4.80 (1H, m), 5.64 (1H, m), 6.15 (1H, m).

Example 8

Synthesis of 9-(2-chloropropionyloxy)-4-thia-5-azatricyclo[4.2.1.0$^{6.7}$]nonane-4,4-dioxide (Reaction (F))

To a four-necked flask having an inner volume of 200 ml and equipped with an electromagnetic stirring device, a reflux condenser, a nitrogen inlet tube, and a thermometer, there were charged 3.0 g (15.9 mmol) of 9-hydroxy-4-thia-5-azatricyclo[4.2.1.0$^{6.7}$]nonane-4,4-dioxide, 50 g of THF and 1.8 g (22.2 mmol) of pyridine, and the mixture was cooled to 5° C. Thereto was added dropwise 2.4 g (19.1 mmol) of 2-chloropropionylchloride over a 30-minute period, and the mixture was stirred at 5° C. for 1 hour. To the reaction mixture was added 30 g of distilled water, the mixture was separated into an organic layer and an aqueous layer, and the aqueous layer was extracted with 50 g of ethyl acetate. After washing with 20 g of distilled water, the organic layer obtained was concentrated under reduced pressure. The residue obtained was recrystallized from ethyl acetate to obtain 1.7 g (6.0 mmol) of 9-(2-chloropropionyloxy)-4-thia-5-azatricyclo[4.2.1.0$^{6.7}$]nonane-4,4-dioxide represented by the following formula (yield: 38%):

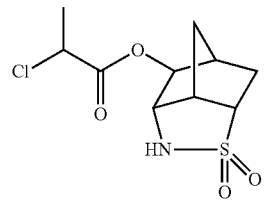 [SMILES: CC(Cl)C(=O)OC1C2CC3C1NS(=O)(=O)C3C2]

$^1$H-NMR (400 MH$_Z$, CDCl$_3$, TMS, ppm) δ: 1.30 (3H, m), 1.75 (1H, m), 2.07-2.14 (3H, m), 2.60 (1H, m), 3.34 (1H, m), 3.36 (1H, m), 3.55 (1H, m), 4.41 (1H, s), 4.60 (1H, m), 4.82 (1H, m).

Example 9

Synthesis of 9-(2-methacryloyloxypropionyloxy)-4-thia-5-azatricyclo[4.2.1.0$^{6.7}$]nonane-4,4-dioxide (Reaction (G))

To a four-necked flask having an inner volume of 200 ml and equipped with an electromagnetic stirring device, a reflux condenser, a nitrogen inlet tube, and a thermometer, there were charged 2.1 g (7.5 mmol) of 9-(2-chloropropionyloxy)-4-thia-5-azatricyclo[4.2.1.0$^{6.7}$]nonane-4,4-dioxide obtained by the method of Example 8, 40 g of DMF, 0.8 g (6.0 mmol) of potassium carbonate, and 1.3 g (0.8 mmol) of potassium iodide, followed by the addition of 0.8 g (9.0 mmol) of methacrylic acid at 20° C., and the mixture was stirred at 50° C. for 8 hours. To the reaction mixture were added 40 g of distilled water and 40 g of ethyl acetate, and the mixture was separated into an organic layer and an aqueous layer. After washing with 10 g of distilled water three times, the organic layer was concentrated under reduced pressure. The residue obtained was purified by silica gel column chromatography to obtain 2.3 g (6.9 mmol) of 9-(2-methacryloyloxypropionyloxy)-4-thia-5-azatricyclo[4.2.1.0$^{6.7}$]nonane-4,4-dioxide represented by the following formula (yield: 92%):

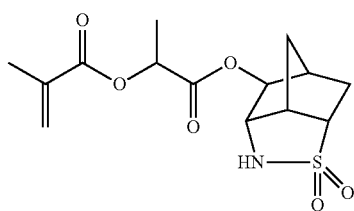 [SMILES: C=C(C)C(=O)OC(C)C(=O)OC1C2CC3C1NS(=O)(=O)C3C2]

$^1$H-NMR (400 MHz, CDCl$_3$, TMS, ppm) δ: 1.25 (3H, m), 1.76 (1H, m), 1.93 (3H, s), 2.05-2.13 (3H, m), 2.58 (1H, m), 3.39 (1H, m), 3.40 (1H, m), 3.58 (1H, m), 4.44 (1H, s), 4.65 (1H, m), 4.81 (1H, m), 5.65 (1H, m), 6.16 (1H, m).

Example 10

Synthesis of Polymer (a)

To a separable flask equipped with a thermometer, a reflux condenser, and a nitrogen inlet tube, there were charged 6.8 g (39.7 mmol) of the compound (VII-2), 9.8 g (41.7 mmol) of the compound (I-2), and 6.9 g (26.8 mmol) of 9-methacryloyloxy-4-thia-5-azatricyclo[4.2.1.0$^{6.7}$]nonane-4,4-dioxide obtained by the method of Example 3, and the mixture was dissolved in 45 g of THF. To this solution was added and dissolved 26.2 mmol of dimethyl azobisisobutyrate (V-601, produced by Wako Pure Chemical Industries, Ltd.). The resultant mixture was added dropwise to 25 g of THF, and the mixture was heated to 65° C., over a 6 hour period under a nitrogen atmosphere. After the dropwise addition was complete, the reaction solution was heated and stirred for 1 hour and, thereafter, cooled to room temperature. The polymerization reaction mixture obtained was added dropwise to a large volume of a mixed solvent of methanol/water to carry out an operation to precipitate a reaction product. The reaction product deposited was separated by filtration, washed, and dried to obtain 13.7 g of polymer (a) represented by the following formula.

The Mw of this polymer (a) was 10,500 and the Mw/Mn thereof was 1.61. Furthermore, a copolymer composition ratio thereof determined by $^{13}$C-NMR (600 MHz) was: p/q/r=34/41/25:

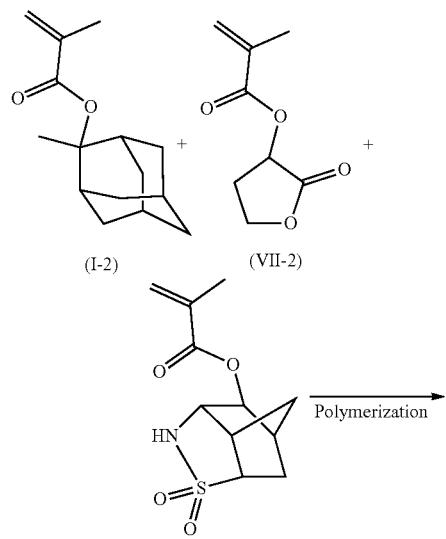

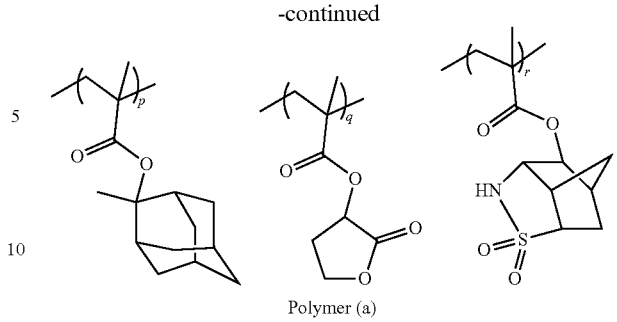

Polymer (a)

Example 11

Synthesis of Polymer (b)

Except that 6.8 g (39.7 mmol) of the compound (VII-2), 9.8 g (41.7 mmol) of the compound (I-2), and 7.7 g (26.8 mmol) of 9-methacryloyloxymethoxy-4-thia-5-azatricyclo[4.2.1.0$^{6.7}$]nonane-4,4-dioxide obtained by the method of Example 5 were used in Example 10, operations were carried out in the same manner as in Example 10 to obtain 12.7 g of polymer (b) represented by the following formula. The Mw of this polymer (b) was 11,500 and the Mw/Mn thereof was 1.60. Furthermore, the copolymer composition ratio thereof determined by $^{13}$C-NMR (600 MHz) was: p/q/r=33/42/25:

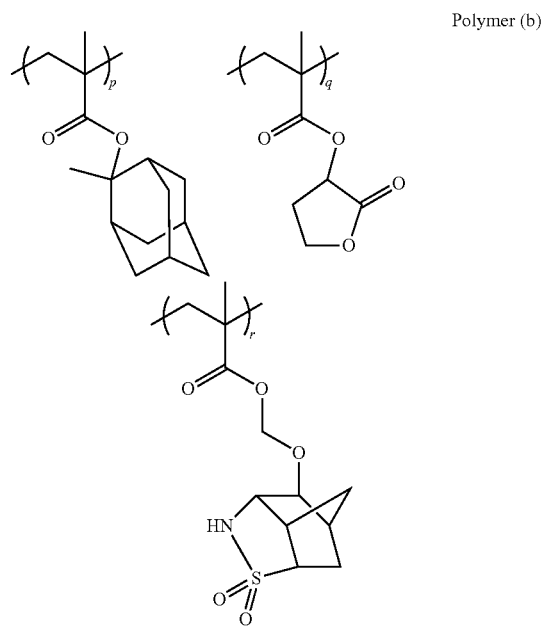

Polymer (b)

Example 12

Synthesis of Polymer (c)

Except that 6.8 g (39.7 mmol) of the compound (VII-2), 9.8 g (41.7 mmol) of the compound (I-2), and 8.4 g (26.8 mmol) of 9-methacryloyloxyacetoxy-4-thia-5-azatricyclo[4.2.1.0$^{6.7}$]nonane-4,4-dioxide obtained by the method of Example 7 were used in Example 10, operations were carried out in the same manner as in Example 10 to obtain 12.3 g of polymer (c) represented by the following formula. The Mw of this polymer (c) was 10,300 and the Mw/Mn thereof was 1.61. Furthermore, the copolymer composition ratio thereof determined by $^{13}$C-NMR (600 MHz) was: p/q/r=35/40/25:

Polymer (c)

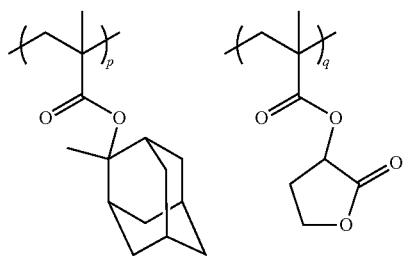

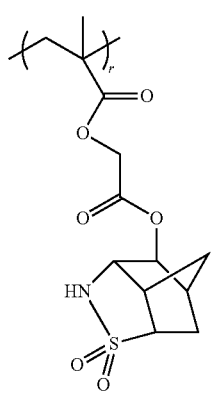

Example 13

Synthesis of Polymer (d)

Except that 6.8 g (39.7 mmol) of the compound (VII-2), 9.8 g (41.7 mmol) of the compound (I-2), and 8.8 g (26.8 mmol) of 9-(2-methacryloyloxypropionyloxy)-4-thia-5-azatricyclo[4.2.1.0$^{6,7}$]nonane-4,4-dioxide obtained by the method of Example 9 were used in Example 10, operations were carried out in the same manner as in Example 10 to obtain 14.2 g of polymer (d) represented by the following formula. The Mw of this polymer (d) was 11,700 and the Mw/Mn thereof was 1.55. Furthermore, the copolymer composition ratio thereof determined by $^{13}$C-NMR (600 MHz) was: p/q/r=34/41/25:

Polymer (d)

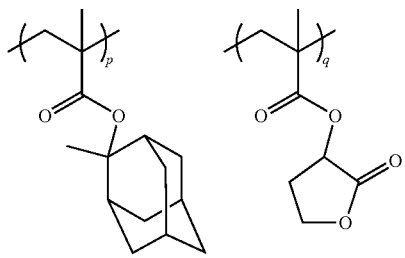

-continued

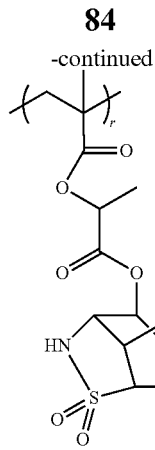

Reference Example 2

Synthesis of Polymer (e)

Except that 6.8 g (39.7 mmol) of compound (VII-2), 9.8 g (41.7 mmol) of the compound (I-2), and 5.9 g (26.8 mmol) of the compound (IV-2) were used in Example 10, operations were carried out in the same manner as in Example 10 to obtain 11.2 g of polymer (e) represented by the following formula.

The Mw of this polymer (e) was 9,700 and the Mw/Mn thereof was 1.75. Furthermore, the copolymer composition ratio thereof determined by $^{13}$C-NMR (600 MHz) was: p/q/r=33/42/25:

Polymer (e)

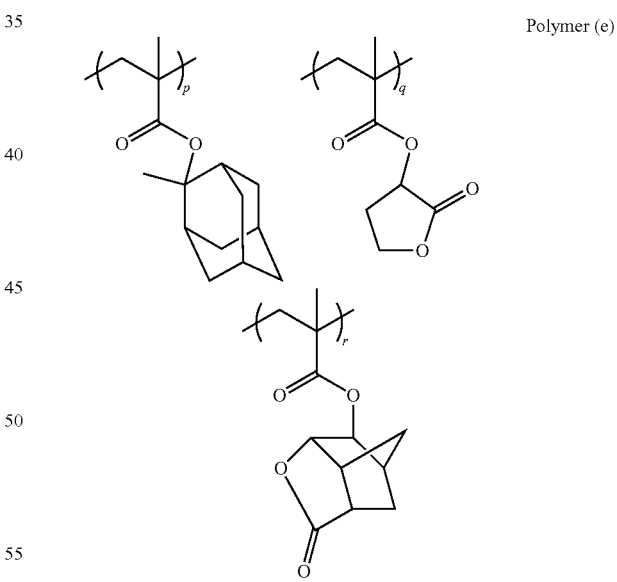

Reference Example 3

Synthesis of Polymer (f)

Except that 6.8 g (39.7 mmol) of the compound (VII-2), 9.8 g (41.7 mmol) of the compound (I-2), and 6.8 g (26.8 mmol) of the compound (IV-14) were used in Example 10, operations were carried out in the same manner as in Example 10 to obtain 13.2 g of polymer (f) represented by the following formula. The Mw of this polymer (e) was 9,900 and the Mw/Mn thereof was 1.71. Furthermore, the copolymer composition ratio thereof determined by $^{13}$C-NMR (600 MHz) was: p/q/r=33/42/25:

Polymer (f)

Reference Example 4

Synthesis of Polymer (g)

Except that 6.8 g (39.7 mmol) of the compound (VII-2), 9.8 g (41.7 mmol) of the compound (I-2), and 7.5 g (26.8 mmol) of the compound (IV-5) were used in Example 10, operations were carried out in the same manner as in Example 10 to obtain 11.5 g of polymer (g) represented by the following formula. The Mw of this polymer (g) was 11,000 and the Mw/Mn thereof was 1.61. Furthermore, the copolymer composition ratio thereof determined by $^{13}$C-NMR (600 MHz) was: p/q/r=33/43/24:

Polymer (g)

Reference Example 5

Synthesis of Polymer (h)

Except that 6.8 g (39.7 mmol) of the compound (VII-2), 9.8 g (41.7 mmol) of the compound (I-2), and 7.9 g (26.8 mmol) of the compound (IV-13) were used in Example 10, operations were carried out in the same manner as in Example 10 to obtain 13.1 g of polymer (h) represented by the following formula. The Mw of this polymer (h) was 10,200 and Mw/Mn thereof was 1.68. Furthermore, the copolymer composition ratio thereof determined by $^{13}$C-NMR (600 MHz) was: p/q/r=32/44/24:

Polymer (h)

Evaluation Examples 1-8

Eight kinds of photoresist compositions were prepared by mixing 100 mass parts of the polymer (a), (b), (c), (d), (e), (f), (g), or (h) obtained in Examples 10 to 13 and Reference Examples 2 to 5; 4.5 mass parts of "TPS-109" (product name, component: triphenylsulfonium nonafluoro-n-butanesulfonate, produced by Midori Kagaku Co., Ltd.) as a photoacid generator; and 1896 mass parts of a mixed solvent of propylene glycol monomethyl ether acetate/cyclohexanone (mass ratio=1:1) as a solvent.

These photoresist compositions were filtered respectively using a membrane filter of 0.2 μm pore diameter. Subsequently, on a silicon wafer of 10 cm diameter on which an antireflection film (a base film) of 100 nm thickness was formed by coating a 6 mass % solution of a cresol novolac resin ("PS-6937" produced by Gunei Chemical Industry Co., Ltd.) in propylene glycol monomethyl ether acetate by a spin coating method and by heating on a hot plate at 200° C. for 90 seconds, the photoresist compositions were coated respectively by a spin coating method and pre-baked on a hot plate at 130° C. for 90 seconds to form a resist film of 300 nm thickness. This resist film was subjected to two-beam interferometry exposure using an ArF excimer laser at the wavelength of 193 nm. Successively, after post-exposure baking at 130° C. for 90 seconds, the resist film was developed with a 2.38 mass % aqueous tetramethyl hydroxide solution for 60 seconds to form a 1:1 line and space pattern.

The developed wafer was cut, and a piece obtained was observed by a scanning electron microscope (SEM) to examine the shape of a pattern obtained at an exposure amount which resolved a 1:1 line and space pattern having a line width of 100 nm and to measure a variation in the line width (LWR).

To evaluate the LWR, the line width was measured using a monitoring apparatus at a plurality of positions and variance (3σ) of scattering of the detecting position was taken as an index. Further, the cross-sectional shape of the pattern was inspected using a scanning electron microscope (SEM) and a pattern with high rectangularity was evaluated as "good" and a pattern with low rectangularity was evaluated as "poor." The results are shown in Table 1.

TABLE 1

| | Exposure evaluation | | |
|---|---|---|---|
| | Polymer used | LWR(nm) | Pattern shape |
| Evaluation example 1 | 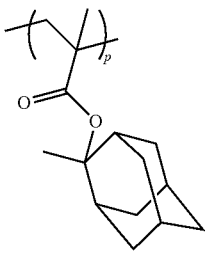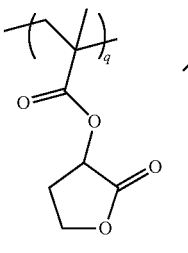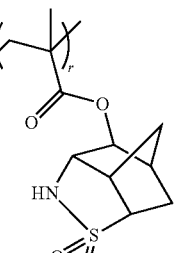 Polymer (a) | 5.9 | Good |
| Evaluation example 2 | 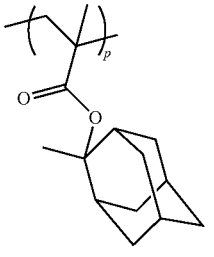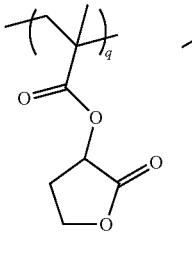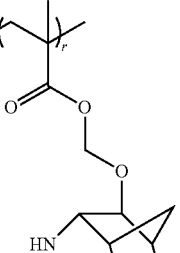 Polymer (b) | 6.0 | Good |

TABLE 1-continued
Exposure evaluation
| | Polymer used | LWR(nm) | Pattern shape |
|---|---|---|---|
| Evaluation example 3 | 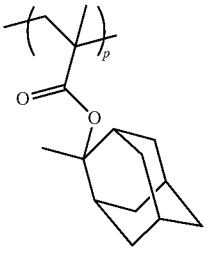 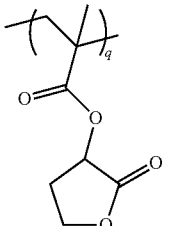 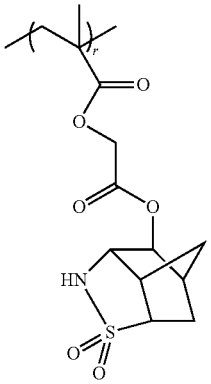  Polymer (c) | 6.1 | Good |
| Evaluation example 4 | 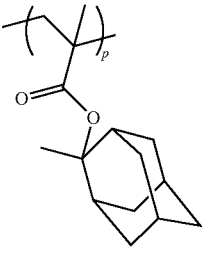 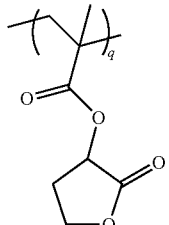 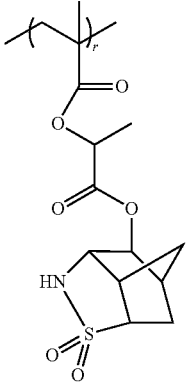  Polymer (d) | 5.8 | Good |
TABLE 2
Exposure evaluation
| | Polymer used | LWR(nm) | Pattern shape |
|---|---|---|---|
| Evaluation example 5 | 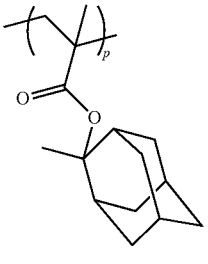 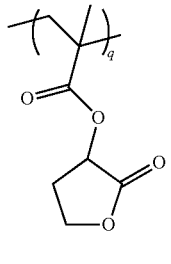 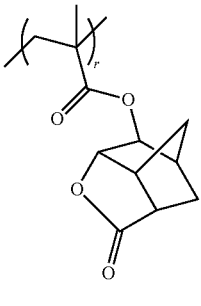  Polymer (e) | 8.5 | Good |

TABLE 2-continued
| | Exposure evaluation | | |
|---|---|---|---|
| | Polymer used | LWR(nm) | Pattern shape |
| Evaluation Example 6 | 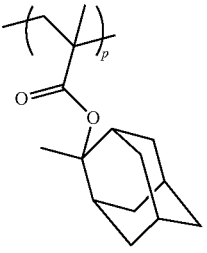<br>Polymer (f) | 9.0 | Good |
| Evaluation Example 7 | 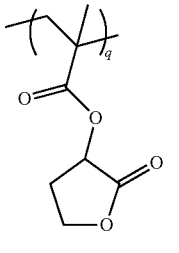<br>Polymer (g) | 9.2 | Good |
| Evaluation example 8 | 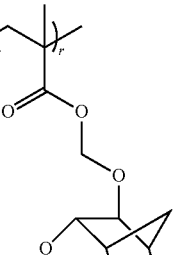<br>Polymer (g) | 9.3 | Good |

From Table 1, it is clear that the photoresist compositions containing the polymers (a) to (d), which contain constituent units based on the acrylic acid ester derivatives (1), can form photoresist patterns having a better shape and show improved LWR compared to the photoresist compositions which contain the polymers (e) to (h), which do not contain the acrylic acid ester derivative (1). That is, both formation of a high resolution photoresist pattern and reduction of the LWR were satisfied.

INDUSTRIAL APPLICABILITY

The acrylic acid ester derivative obtained by the present invention is useful as a raw material of a polymer, which contains the acrylic acid ester derivative as a constituent unit, and of a photoresist composition for a semiconductor, which contains the polymer as a component.

The invention claimed is:

1. An alcohol derivative represented by formula (2):

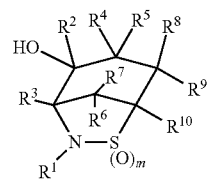

(2)

wherein $R^1$ represents a hydrogen atom, an alkyl group having 1 to 10 carbon atoms, or a cycloalkyl group having 3 to 10 carbon atoms; $R^2$, $R^3$, $R^5$, $R^6$, $R^8$, $R^9$, and $R^{10}$ each independently represent a hydrogen atom, an alkyl group having 1 to 6 carbon atoms, a cycloalkyl group having 3 to 6 carbon atoms, or an alkoxy group having 1 to 4 carbon atoms; $R^4$ and $R^7$ each independently represent a hydrogen atom, an alkyl group having 1 to 6 carbon atoms, a cycloalkyl group having 3 to 6 carbon atoms, or an alkoxy group having 1 to 4 carbon atoms, or the two bind together to represent an alkylene group having 1 to 3 carbon atoms, —O—, or —S—; and m represents 0, 1, or 2.

2. A method for producing the alcohol derivative represented by formula (2) of claim 1;

wherein an epoxy derivative represented by formula (8):

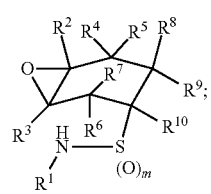

(8)

is cyclized in the presence of an acid or a base.

3. An ether derivative represented by formula (4):

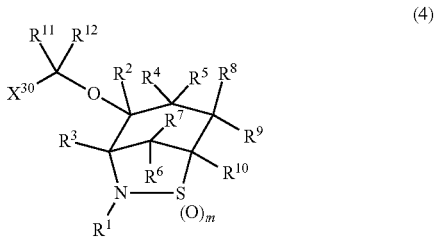

(4)

wherein $R^1$ represents a hydrogen atom, an alkyl group having 1 to 10 carbon atoms, or a cycloalkyl group having 3 to 10 carbon atoms; $R^2$, $R^3$, $R^5$, $R^6$, $R^8$, $R^9$, and $R^{10}$ each independently represent a hydrogen atom, an alkyl group having 1 to 6 carbon atoms, a cycloalkyl group having 3 to 6 carbon atoms, or an alkoxy group having 1 to 4 carbon atoms; $R^4$ and $R^7$ each independently represent a hydrogen atom, an alkyl group having 1 to 6 carbon atoms, a cycloalkyl group having 3 to 6 carbon atoms, or an alkoxy group having 1 to 4 carbon atoms, or the two bind together to represent an alkylene group having 1 to 3 carbon atoms, —O—, or —S—; $R^{11}$ and $R^{12}$ each independently represent a hydrogen atom, an alkyl group having 1 to 6 carbon atoms, or a cycloalkyl group having 3 to 6 carbon atoms; $X^{30}$ represents a chlorine atom, a bromine atom, or an iodine atom; and m represents 0, 1, or 2.

4. A method for producing the ether derivative represented by formula (4) of claim 3;

wherein an alcohol derivative represented by formula (2), a carbonyl compound represented by formula (3) and a halogen halide are reacted

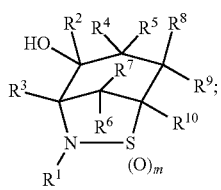

(2)

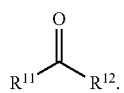

(3)

* * * * *